US010954310B2

(12) United States Patent
Macdonald et al.

(10) Patent No.: US 10,954,310 B2
(45) Date of Patent: Mar. 23, 2021

(54) MICE THAT MAKE $V_L$ BINDING PROTEINS

(71) Applicant: Regeneron Pharmaceuticals, Inc., Tarrytown, NY (US)

(72) Inventors: Lynn Macdonald, Harrison, NY (US); Sean Stevens, Del Mar, CA (US); Cagan Gurer, Chappaqua, NY (US); Karolina A. Meagher, Yorktown Heights, NY (US); Andrew J. Murphy, Croton-on-Hudson, NY (US)

(73) Assignee: Regeneran Pharmaceuticals, Inc., Tarrytown, NY (US)

( * ) Notice: Subject to any disclaimer, the term of this patent is extended or adjusted under 35 U.S.C. 154(b) by 0 days.

(21) Appl. No.: 15/497,075

(22) Filed: Apr. 25, 2017

(65) Prior Publication Data
US 2017/0223939 A1  Aug. 10, 2017

Related U.S. Application Data

(60) Continuation of application No. 14/135,510, filed on Dec. 19, 2013, now Pat. No. 9,686,970, which is a division of application No. 13/195,951, filed on Aug. 2, 2011, now Pat. No. 9,516,868.

(60) Provisional application No. 61/369,909, filed on Aug. 2, 2010.

(51) Int. Cl.
*A01K 67/027* (2006.01)
*C12N 5/10* (2006.01)
*C12N 5/20* (2006.01)
*C07K 16/46* (2006.01)
*C07K 16/00* (2006.01)
*C12N 15/85* (2006.01)
*C07K 16/08* (2006.01)

(52) U.S. Cl.
CPC ........ *C07K 16/468* (2013.01); *A01K 67/0275* (2013.01); *A01K 67/0278* (2013.01); *C07K 16/00* (2013.01); *C07K 16/082* (2013.01); *C07K 16/461* (2013.01); *C12N 15/8509* (2013.01); *A01K 2217/072* (2013.01); *A01K 2227/105* (2013.01); *A01K 2267/01* (2013.01); *C07K 2317/14* (2013.01); *C07K 2317/21* (2013.01); *C07K 2317/31* (2013.01); *C07K 2317/56* (2013.01); *C07K 2317/92* (2013.01); *C12N 2015/8518* (2013.01)

(58) Field of Classification Search
None
See application file for complete search history.

(56) References Cited

U.S. PATENT DOCUMENTS

| 4,977,081 | A | 12/1990 | Raybould et al. |
| 5,545,806 | A | 8/1996 | Lonberg et al. |
| 5,545,807 | A | 8/1996 | Surani et al. |
| 5,770,429 | A | 6/1998 | Lonberg et al. |
| 5,800,988 | A | 9/1998 | Casterman et al. |
| 5,840,526 | A | 11/1998 | Casterman et al. |
| 5,874,541 | A | 2/1999 | Casterman et al. |
| 5,939,598 | A | 8/1999 | Kucherlapti et al. |
| 5,942,435 | A | 8/1999 | Wheeler |
| 6,005,079 | A | 12/1999 | Casterman et al. |
| 6,015,695 | A | 1/2000 | Casterman et al. |
| 6,075,181 | A | 6/2000 | Kucherlapati et al. |
| 6,150,584 | A | 11/2000 | Kucherlapati et al. |
| 6,162,963 | A | 12/2000 | Kucherlapati et al. |
| 6,255,458 | B1 | 7/2001 | Lonberg et al. |
| 6,461,818 | B1 | 10/2002 | Bradley et al. |
| 6,586,251 | B2 | 7/2003 | Economides et al. |
| 6,596,541 | B2 | 7/2003 | Murphy et al. |
| 6,632,976 | B1 | 10/2003 | Tomizuka et al. |
| 6,657,103 | B1 | 12/2003 | Kucherlapati et al. |
| 6,673,986 | B1 | 1/2004 | Kucherlapati et al. |
| 6,765,087 | B1 | 7/2004 | Casterman et al. |
| 6,774,279 | B2 | 8/2004 | Dymecki |
| 6,998,514 | B2 | 2/2006 | Bruggemann |
| 7,064,244 | B2 | 6/2006 | Jakobovits et al. |
| 7,105,348 | B2 | 9/2006 | Murphy et al. |

(Continued)

FOREIGN PATENT DOCUMENTS

| CN | 1203922 A | 1/1999 |
| EP | 0583980 A1 | 8/1993 |

(Continued)

OTHER PUBLICATIONS

Goldman et al., 2004 (Med Sci Monit, vol. 10, No. 11, RA274-285.*
Vetterman et al Allelic exclusion of mmunoglobulin genes: models and mechanisms Immunological Reviews 2010; pp. 22-42.*
Giraldo et al Size matters: use of YACs, BACs and PACs in transgenic animalsTransgenic Research 10: 83-103, 2001.*
U.S. Appl. No. 16/015,159 accolate letter by the Office of Patent Quality Assurance (OPQA), Jan. 16, 2020, p. 1.*
Jensen, et al. (2007) One Step Generation of Fully Chimeric Antibodies Using Cγ1-and Cκ Mutant Mice, J. Immunother., 30(3):338-349.
Statement of Relatedness under MPEP 2001.06 with Respect to U.S. Appl. No. 15/497,075, dated Dec. 20, 2018.

(Continued)

Primary Examiner — Maria G Leavitt
(74) Attorney, Agent, or Firm — Rita S. Wu; Elysa Goldberg; FisherBroyles, LLP

(57) ABSTRACT

Genetically modified mice and methods for making an using them are provided, wherein the mice comprise a replacement of all or substantially all immunoglobulin heavy chain V gene segments, D gene segments, and J gene segments with at least one light chain V gene segment and at least one light chain J gene segment. Mice that make binding proteins that comprise a light chain variable domain operably linked to a heavy chain constant region are provided. Binding proteins that contain an immunoglobulin light chain variable domain, including a somatically hypermutated light chain variable domain, fused with a heavy chain constant region, are provided. Modified cells, embryos, and mice that encode sequences for making the binding proteins are provided.

6 Claims, 21 Drawing Sheets

Specification includes a Sequence Listing.

(56) References Cited

U.S. PATENT DOCUMENTS

| | | | |
|---|---|---|---|
| 7,183,076 B2 | 2/2007 | Arathoon et al. |
| 7,294,754 B2 | 11/2007 | Poueymirou et al. |
| 7,435,871 B2 | 10/2008 | Green et al. |
| 7,501,552 B2 | 3/2009 | Lonberg et al. |
| 7,582,298 B2 | 9/2009 | Stevens et al. |
| 7,910,798 B2 | 3/2011 | Tanamachi et al. |
| 7,919,257 B2 | 4/2011 | Hoogenboom et al. |
| 7,932,431 B2 | 4/2011 | Bruggemann |
| 8,158,419 B2 | 4/2012 | Lonberg et al. |
| 8,502,018 B2 | 8/2013 | Murphy et al. |
| 8,568,992 B2 | 10/2013 | Walker et al. |
| 8,586,713 B2 | 11/2013 | Davis et al. |
| 8,629,317 B2 | 1/2014 | Cogne et al. |
| 8,642,835 B2 | 2/2014 | Macdonald et al. |
| 8,697,940 B2 | 4/2014 | Macdonald et al. |
| 9,365,655 B2 * | 6/2016 | Craig .................. C07K 16/00 |
| 2002/0026036 A1 | 2/2002 | Shitara et al. |
| 2002/0088016 A1 | 7/2002 | Bruggemann |
| 2002/0106628 A1 | 8/2002 | Economides et al. |
| 2002/0106629 A1 * | 8/2002 | Murphy ............ A01K 67/0275 435/4 |
| 2003/0108925 A1 | 6/2003 | Dix et al. |
| 2003/0109021 A1 | 6/2003 | Wu et al. |
| 2003/0217373 A1 | 11/2003 | Green et al. |
| 2004/0018626 A1 | 1/2004 | Murphy et al. |
| 2004/0101920 A1 | 5/2004 | Radziejewski et al. |
| 2005/0060763 A1 | 3/2005 | Bruggeman et al. |
| 2005/0246782 A1 | 11/2005 | Etches et al. |
| 2006/0015949 A1 | 1/2006 | Lonberg et al. |
| 2006/0015957 A1 * | 1/2006 | Lonberg ............ A01K 67/0275 800/18 |
| 2006/0015958 A1 | 1/2006 | Kuroiwa et al. |
| 2006/0026696 A1 | 2/2006 | Buelow et al. |
| 2006/0083747 A1 | 4/2006 | Winter |
| 2006/0106203 A1 | 5/2006 | Winter |
| 2006/0199204 A1 | 9/2006 | Dix et al. |
| 2006/0257406 A1 | 11/2006 | Winter |
| 2006/0280734 A1 | 12/2006 | Winter |
| 2007/0209083 A1 * | 9/2007 | Thiam ............... C07K 14/70517 800/14 |
| 2007/0275466 A1 | 11/2007 | Economides et al. |
| 2007/0280945 A1 | 12/2007 | Stevens et al. |
| 2008/0267982 A1 | 10/2008 | Kiselev et al. |
| 2009/0258392 A1 | 10/2009 | Gallo et al. |
| 2009/0271880 A1 | 10/2009 | Grosveld et al. |
| 2010/0069614 A1 | 3/2010 | Houtzager et al. |
| 2010/0122358 A1 | 5/2010 | Bruggemann |
| 2010/0146647 A1 | 6/2010 | Logtenberg et al. |
| 2010/0196367 A1 | 8/2010 | Day |
| 2010/0254988 A1 | 10/2010 | Bossenmaier et al. |
| 2010/0254989 A1 | 10/2010 | Bossenmaier et al. |
| 2010/0298542 A1 | 11/2010 | Igawa et al. |
| 2010/0331527 A1 | 12/2010 | Davis et al. |
| 2011/0123527 A1 | 5/2011 | Shizuya et al. |
| 2011/0138489 A1 | 6/2011 | Tanamachi et al. |
| 2011/0145937 A1 | 6/2011 | Macdonald et al. |
| 2011/0195454 A1 | 8/2011 | McWhirter et al. |
| 2011/0236378 A1 | 9/2011 | Green et al. |
| 2011/0283376 A1 | 11/2011 | Murphy et al. |
| 2011/0314563 A1 | 12/2011 | Craig et al. |
| 2012/0021409 A1 | 1/2012 | McWhirter et al. |
| 2012/0047585 A1 | 2/2012 | Rohrer et al. |
| 2012/0070861 A1 | 3/2012 | Macdonald et al. |
| 2012/0073004 A1 | 3/2012 | Macdonald et al. |
| 2012/0096572 A1 | 4/2012 | Macdonald et al. |
| 2012/0167237 A1 | 6/2012 | Bradley et al. |
| 2012/0192300 A1 | 7/2012 | Babb et al. |
| 2012/0204278 A1 | 8/2012 | Bradley et al. |
| 2012/0272344 A1 | 10/2012 | Tanamachi et al. |
| 2013/0045492 A1 | 2/2013 | Babb et al. |
| 2013/0096287 A1 | 4/2013 | Macdonald et al. |
| 2013/0145484 A1 | 6/2013 | Logtenberg et al. |
| 2013/0185821 A1 | 7/2013 | Babb et al. |
| 2013/0198879 A1 | 8/2013 | McWhirter et al. |
| 2013/0212719 A1 | 8/2013 | Macdonald et al. |
| 2013/0243759 A1 | 9/2013 | Friedrich et al. |
| 2013/0243773 A1 | 9/2013 | Van Berkel et al. |
| 2013/0263292 A1 | 10/2013 | Liang et al. |
| 2013/0263293 A1 | 10/2013 | Bradley et al. |
| 2013/0302836 A1 | 11/2013 | McWhirter et al. |
| 2013/0318643 A1 | 11/2013 | Bradley et al. |
| 2013/0323235 A1 | 12/2013 | Craig et al. |
| 2014/0213773 A1 | 7/2014 | Macdonald et al. |
| 2014/0243504 A1 | 8/2014 | Davis et al. |
| 2014/0283150 A1 | 9/2014 | Bradley et al. |
| 2014/0310828 A1 | 10/2014 | Lee et al. |
| 2015/0133641 A1 | 5/2015 | Germaschewski et al. |
| 2015/0201589 A1 | 7/2015 | Macdonald et al. |
| 2015/0210776 A1 | 7/2015 | Macdonald et al. |
| 2015/0250152 A1 | 9/2015 | Jakobovits et al. |
| 2015/0266976 A1 | 9/2015 | Babb et al. |
| 2015/0289489 A1 | 10/2015 | Macdonald et al. |
| 2017/0094955 A1 | 4/2017 | Macdonald et al. |
| 2018/0244804 A1 | 8/2018 | Macdonald et al. |
| 2018/0273641 A1 | 9/2018 | Babb et al. |

FOREIGN PATENT DOCUMENTS

| | | |
|---|---|---|
| EP | 0491057 B1 | 12/1998 |
| EP | 2050764 A1 | 4/2009 |
| EP | 1589107 A1 | 12/2009 |
| KR | 1020050042792 A | 5/2005 |
| WO | 1991/000906 A1 | 1/1991 |
| WO | 1994/012215 A1 | 9/1994 |
| WO | 1994/025585 A1 | 11/1994 |
| WO | 1996/034103 A1 | 10/1996 |
| WO | 1997/016537 A1 | 5/1997 |
| WO | 1990/004036 A1 | 4/1998 |
| WO | 1998/024893 A2 | 6/1998 |
| WO | 2000/026373 A1 | 5/2000 |
| WO | 2000/073323 A2 | 12/2000 |
| WO | 2001/053353 A2 | 7/2001 |
| WO | 2002/012437 A2 | 2/2002 |
| WO | 2002/046237 A2 | 6/2002 |
| WO | 2002/066630 A1 | 8/2002 |
| WO | 2002/085944 A2 | 10/2002 |
| WO | 2002/085945 A2 | 10/2002 |
| WO | 2003/002609 A2 | 1/2003 |
| WO | 2003/047336 A1 | 6/2003 |
| WO | 2004/049794 A2 | 6/2004 |
| WO | 2004/058820 A2 | 7/2004 |
| WO | 2004/058822 A2 | 7/2004 |
| WO | 2005/007696 A2 | 1/2005 |
| WO | 2005/019463 A1 | 3/2005 |
| WO | 2005/028510 A2 | 3/2005 |
| WO | 2005/038001 A2 | 4/2005 |
| WO | 2006/008548 A2 | 1/2006 |
| WO | 2006/047367 A2 | 5/2006 |
| WO | 2007/096779 A2 | 8/2007 |
| WO | 2007/117410 A2 | 10/2007 |
| WO | 2008/027986 A2 | 3/2008 |
| WO | 2008/054606 A2 | 5/2008 |
| WO | 2008/076379 A2 | 6/2008 |
| WO | 2008/151081 A1 | 12/2008 |
| WO | 2009/013620 A2 | 1/2009 |
| WO | 2009/018386 A1 | 2/2009 |
| WO | 2009/026660 A1 | 3/2009 |
| WO | 2009/097006 A2 | 8/2009 |
| WO | 2009/143472 A2 | 11/2009 |
| WO | 2009/157771 A2 | 12/2009 |
| WO | 2010/039900 A2 | 4/2010 |
| WO | 2011/004192 A1 | 1/2011 |
| WO | 2011/072204 A1 | 6/2011 |
| WO | 2011/158009 A1 | 12/2011 |
| WO | 2011/163311 A1 | 12/2011 |
| WO | 2011/163314 A1 | 12/2011 |
| WO | 2012/018764 A1 | 2/2012 |
| WO | 2012/063048 A1 | 5/2012 |
| WO | 2012/116927 A1 | 9/2012 |
| WO | 2012/166926 A1 | 9/2012 |
| WO | 2012/141798 A1 | 10/2012 |
| WO | 2013/022782 A1 | 2/2013 |
| WO | 2013/041844 A2 | 3/2013 |
| WO | 2013/041845 A2 | 3/2013 |

(56) References Cited

FOREIGN PATENT DOCUMENTS

| | | |
|---|---|---|
| WO | 2013/041846 A2 | 3/2013 |
| WO | 2013/045916 A1 | 4/2013 |
| WO | 2013/061078 A1 | 5/2013 |
| WO | 2013/061098 A2 | 5/2013 |
| WO | 2013/079953 A1 | 6/2013 |
| WO | 2013/096142 A1 | 6/2013 |
| WO | 2013/116609 A1 | 8/2013 |
| WO | 2015/143406 A2 | 9/2015 |
| WO | 2015/143414 A2 | 9/2015 |

OTHER PUBLICATIONS

Austin et al. (2004) "The Knockout Mouse Project," Nature Genetics, 36(9):921-924.
Chang et al. (1985) "Novel Arrangement of Immunoglobulin Variable Domains X-Ray Crystallographic Analysis of the Lambda-Chain Dimer Bence-Jones Protein LOC," Biochemistry, American Chemical Society, 24(18):4890-4897.
Melton (2002) Chapter 8: Gene-Targeting Strategies, Methods in Molecular Biology, Transgenesis Techniques, 2nd Edition, Principles and Protocols, 180:19 pages.
Murphy, A., VelocImmune: Immunoglobulin Variable Region Humanized Mice, Recombinant Antibodies for Immunotherapy, Ed. Little, M., New York, NY: Cambridge University Press, Chapter 8, pp. 100-107 (2009).
Roebroek et al. (2003) "Chapter 10: Knockin Approaches," Methods in Molecular Biology, Transgenic Mouse Methods and Protocols, 209:16 pages.
Schwartz and Cantor (1984) "Separation of Yeast Chromosome-Sized DNAs by Pulsed Field Gradient Gel Electrophoresis," Cell, 37:67-75.
Sorrell and Kolb (2004) "Chapter XI: Targeted Modification of Mammalian Genomes," Focus on Genome Research, 6 pages.
Storb et al. (1986) "Transgenic Mice with µ and κ Genes Encoding Antiphosphorycholine Antibodies," J. Exp. Med., 164:627-664.
Zhang et al. (1998) "A new logic for DNA engineering using recombination in *Escherichia coli*," Nature Genetics, 20:123-138.
Statement of Relatedness under MPEP 2001.06 with Respect to U.S. Appl. No. 15/497,075, dated Aug. 24, 2018.
Cao, et al. (2009) Isolation and Culture of Primary Bovine Embryonic Stem Cell Colonies by a Novel Method, Journal of Experimental Zoology, 311A:368-376.
Houdebine et al. "Methods to Generate Transgenic Animals," Genetic Engineering in Livestock, New Applications and Interdisciplinary Perspectives, Engelhard M, et al., 2009, XVI, 146, pp. 31-47.
Statement of Relatedness under MPEP 2001.06 with Respect to U.S. Appl. No. 15/497,075, dated Jan. 2, 2019.
Adams et al. (2005) "A genome-wide, end-sequenced 129Sv BAC library resource for targeting vector construction," Genomics, 86(6):753-758.
Adderson et al. (1991) "Restricted Ig H Chain V Gene Usage in the Human Antibody Response to Haemophilus influenzae Type b Capsular Polysaccharide," The Journal of Immunology, 147:1667-1674.
Adderson et al. (1993) "Restricted Immunoglobulin VH Usage and VDJ Combinations in the Human Response to Haemophilus influenzae Type b Capsular Polysaccharide," J. Clin. Invest., 91:2734-2743.
Almagro et al. (2004) "Identification of differences in the specificity-determining residues of antibodies that recognize antigens of different size: implications for the rational design of antibody repertoires," Journal of Molecular Recognition, 17(2):132-143.
Altschul et al. (1990) "Basic local alignment search tool," J. Mol. Biol., 215(3): 403-410.
Altschul et al. Methods in Enzymology.
Altschul et al. (1997) "Gapped BLAST and PSI-BLAST: a new generation of protein database search programs," Nucleic Acids Res. 25:3389-3402.
Amit and Itskovitz-Eldor (2009) "Embryonic Stem Cells: Isolation, Characterization and Culture," Adv. Biochem. Eng. Biotechnol, 114:173-184.
Andris-Widhopf et al. (2000) "Methods for the generation of chicken monoclonal antibody fragments by phage display," J. Immunol. Methods 242:159-181.
Astellas Negotiates $295M License Extension to Regeneron's VelocImmune mAb Platform, Genetic Engineering & Biotechnology News, Jul. 28, 2010, 2 pages.
Auerbach et al. (2000) "Establishment and Chimera Analysis of 129/SvEv- and C57BL/6-Derived Mouse Embryonic Stem Cell Lines," BioTechniques, 29(5):1024-1028, 1030, 1032.
Author Not Known (2007) "Breeding Strategies for Maintaining Colonies of Laboratory Mice," A Jackson Laboratory Resource Manual, pp. 1-29.
Azzazy and Highsmith (2002) "Phage display technology: clinical applications and recent innovations," Clin. Biochem. 35:425-445.
Baird and Myszka (2001) "Current and emerging commercial optical biosensors," J. Molecular Recognition, 14:261-268.
Bando et al. (2004) "Characterization of VH gene expressed in PBL from children with atopic diseases: detection of homologous VH1-69 derived transcripts from three unrelated patients," Immunology Letters, 94:99-106.
Bankovich et al. (2007) "Structural Insight into Pre-B Cell Receptor Function," Science, 316(5822):291-294.
Baseggio et al. (2010) "CD5 expression identifies a subset of splenic marginal zone lymphomas with higher lymphocytosis: a clinicopathological, cytogenetic and molecular study of 24 cases," Haematologica, 95(4):604-612.
Bates et al. (2007) "Chromosomal position of a VH gene segment determines its activation and inactivation as a substrate for V(D)J recombination," Journal of Experimental Medicine, 204(13):3247-3256.
Berberian et al. (1991) "A VH Clonal Deficit in Human Immunodeficiency VirUS Positive Individuals Reflects a B-Cell Maturational Arrest," Blood, 78(1):175-179.
Blankenstein et al. (1987) "Immunoglobulin $V_H$ region genes of the mouse are oranized in overlapping clusters*," Eur. J. Immunol., 17:1351-1357.
Brevini et al. (2010) "No shortcuts to pig embryonic stem cells," Theriogenology 74(4):544-550.
Brezinschek et al. (1995) "Analysis of the Heavy Chain Repertoire of Human Peripheral B Cells Using Single-Cell Polymerase Chain Reaction," Journal of Immunology, 155:190-202.
Brodeur et al. (1984) "The immunoglobulin heavy chain variable region (Igh-V) locus in the mouse I. One hundred IgH-V genes comprise seven families of homologous genes*," Eur. J. Immunol., 14:922-930.
Brouwers et al. (2015) "Unexpected Phenotypes in Mouse Models Carrying the Human Growth Hormone Minigene to Enhance Transgene Expression," Journal of Steroids & Hormonal Science, 6(2):1-2.
Bruchez et al. (1998) "Semiconductor Nanocrystals as Fluorescent Biological Labels," Science 281: 2013-2016.
Brüggemann et al. (1989) "A repertoire of monoclonal antibodies with human heavy chains from transgenic mice," Proceedings of the National of Academy of Science USA, 86:6709-6713.
Brüggemann and Neuberger (1996) "Strategies for expressing human antibody repertoires in transgenic mice," Review Immunology Today, 192(17):391-397.
Brüggemann (2001) "Human Antibody Expression in Transgenic Mice," Archivum Immunologiae et Therapiae Experimentalis, 49:203-208.
Brüggemann (2004) "Human Monoclonal Antibodies from Translocus Mice," Molecular Biology of B Cells, Eds. Honjo, T. and Neuberger, M.S., New York, NY: Academic Press, pp. 547-561.
Burton (1995) "Phage display," Immunotechnology 1:87-94.
Butler, (1998) "Immunoglobulin diversity, B-cell and antibody repertoire development in large farm animals," Rev. Sco. Tech. Off. Int. Epiz., 17(1):43-70.
Carbonari et al. (2005) "Hepatitis C Virus Drives the Unconstrained Monoclonal Expansion of VH1-69-Expressing Memory B Cells in Type II Cryoglobulinemia: A Model of Infection-Driven Lymphomagenesis," The Journal of Immunology, 174:6532-6539.

(56) References Cited

OTHER PUBLICATIONS

Cavelier et al. (1997) "B lineage-restricted rearrangement of a human Ig kappa transgene," Eur J. Immunol. 27(7):1626-1631.
Chan et al. (2001) "VH1-69 gene is preferentially used by hepatitis C virUS associated B cell lymphomas and by normal B cells responding to the E2 viral antigen," Blood, 97(4):1023-1026.
Chang et al. (1984) "Immunologic memory to phosphocholine. IV. Hybridomas representative of Group I (T15-like) and Group II (non-T15-like) antibodies utilize distinct VH genes," J. Immunol., 132(3):1550-1555.
Charles et al. (2011) "A flow cytometry-based strategy to identify and express IgM from VH1-69+ clonal peripheral B cells," Journal of Immunological Methods, 363:210-220.
Cheval et al. (2012) Of Mice and Men: Divergence of Gene Expression Patterns in Kidney, PLoS One, 7(10):e46876 (12 pages).
Cho, Chunghee, (2012) "Testicular and epididymal ADAMs: experssion and function during fertilization," Nature Reviews Urology, 9:550-560.
Choi et al. (2004) "Characterization and comparative genomic analysis of intronless Adams with testicular gene expression," Genomics, 83(4):636-646.
Choi et al. (2011) "Expression of the metabotropic glutamate receptor 5 (mGluR5) induces melanoma in transgenic mice," PNAS, 108(37):15219-15224.
Choi et al. (2013) "Identification and characterizaion of promoter and regulatory regions for mouse Adam2 gene expression," Molecular Biology Reports, 40:787-796.
Clark and Whitelaw, (2003) "A future for transgenic livestock, National Reviews Genetics," 4(10):825-833.
Cocea et al. (1999) "A targeted deletion of a region upstream from the Jkppa cluster impairs kappa chain rearrangement in cis in mice and in the 103/bcl2 cell line," J. Exp. Med., 189(9):1443-1450.
Combriato et al. (2002) "Regulation of Human Igl Light Chain Gene Expression," The Journal of Immunology, 168:1259-1266.
Davidkova et al. (1997) "Selective Usage of VH Genes in Adult Human B Lymphocyte Repertoires," Scand. J. Immunol., 45:62-73.
Deegan (1976) "Bence Jones Proteins: Nature, Metabolism, Detection and Significance," Annals of Clinical and Laboratory Science, 6(1):38-46.
De Genssst et al. (2006) Antibody repertoire development in camelids. Dev. Comp. Immunol, 30:187-198.
Dennis (2002) "Welfare issues of genetically modified animals," ILAR Journal, 43(2):100-109.
Edmundson et al. (1993) "Priniciples and Pitfalls in Designing Site-Directed Peptide Ligands," Proteins: Structure, Function, and Genetics, Wiley-Liss, Inc., 16:246-267.
Edwards et al. (2008) "The ADAM metalloproteinases, Molecular Aspects of Medicine," 29(5):258-289.
Enever et al. (2009) "Next generation immunotherapeutics—honing the magic bullet. Current Opinion in Biotechnology," 20:405-411.
Featherstone, K et al. (2010) "The mouse immunoglobulin heavy chain V-D intergenic sequence contains insulators that may regulate ordered V(D)J recombination," J. Biol. Chem., 285(13): 9327-9338.
Festing et al. (1999) "Revised nomenclature for strain 129 mice," Mamm. Genome 10:836.
Gallo et al. (2000) "The human immunoglobulin loci introduced into mice: V (D) and J gene segment usage similar to that of adult humans," Eur. J. Immunol., 30(2):534-540.
Gama Sosa et al. (2010)" Animal transgenesis: an overview," Brain Structure & Function, 214(2-3):91-109.
Gavilondo and Larrick (2002) BioTechniques 29:128-145.
Gavish et al. (1977) "Comparison of the fine specificity of anti-dinitrophenyl-combining site composed of either VL dimer or VL and VH of protein 315," Biochemistry, 16(14):3154-3159.
GenBank accession No. NT_114985, p. 1, first referenced Dec. 1, 2005, last updated Feb. 9, 2015.
Giallourakis et al. (2010) "Elements between the IgH variable (V) and diversity (D) clusters influence antisense transcription and lineage-specific V(D)K recombination," PNAS, 107(51):22207-22212.

Goni et al. (1985) "Sequence similarities and cross-idiotypic specificity of L chains among human monoclonal IgMk with anti-gamma-globulin activity," J. Immunol, 135(6):4073-9.
Gonnet et al. (1992) Exhaustive Matching of the Entire Protein Sequence Database, Science 256:1443-45.
Gorman et al. (1996) "The Ig(kappa) enhancer influences the ratio of Ig(kappa) versus Ig(lambda) B lymphocytes," Immunity, 5(3):241-252.
Grawunder et al. (1995) "Induction of sterile transcription from the kappa L chain gene locus in V(D)J recombinase-deficient progenitor B cells," International Immunology, 7(12):1915-1925.
Green, L.et al. (1994) "Antigen-specific human monoclonal antibodies from mice engineered with human Ig heavy and light chain YACs," Nature Genetics, 7(1):13-21.
Gunther et al. (2007) "SuperHapten: a comprehensive database for small immunogenic compounds," Nucleic Acid Research, 35:D906-D910.
Haines and Brodeur (1998) Accessibility changes across the mouse Igh-V locus during B cell development, Eur. J. Immunol., 28:4228-4235.
Han et al. (2009) "Comprehensive analysis of reproductive ADAMs: relationship of ADAM4 and ADAM6; with an ADAM complex required for fertilization in mice," Biology of Reproduction, 80(5):1001-1008.
Harding and Lonberg (1995) "Class switching in human immunoglobulin transgenic Mice," Ann. N Y Acad. Sci., 764:536-546.
Helms and Wetzel (1995) "Destabilizing loop swaps in the CDRs of an immunoglobulin $V_L$ domain," Protein Science, 4:2073-2081.
Hendricks et al. (2010) "Organization of the variable region of the immunoglobulin heavy-chain gene locus of the rat," Immunogenetics, 62(7):479-486.
Hirabayashi et al. (1995) "Kinetic analysis of the interactions of recombinant human VpreB and Ig V domains," J. Immunol., 155:1218-1228.
Hoiruchi and Blobel (2005) Studies from Adam Knockout Mice, in Hooper and Lendeckel, The ADAM Family of proteases, Netherlands 2005, Springer (37 pages).
Hoogenboom (1997) "Designing and optimizing library selection strategies for generating high-affinity antibodies," TIB Tech. 15:62-70.
Hoogenboom and Chames (2000) "Antibodies isolated from an animal (e.g., a mouse) that is transgenic for human immunoglobulin genes," Immunology Today 21:371-378.
House mouse (MUS musculus) IGH locus on chromosome 12 (12F2) strain C57BL/6 pp. 1-5; dowloaded Aug. 26, 2016.
Huang et al. (1993) "A Majority of Ig H Chain cDNA of Normal Human Adult Blood Lymphocytes Resembles cDNA for Fegal Ig and Natural Autoantibodies," The Journal of Immunology, 151(10):5290-5300.
Hussack et al. (2012) "A VL single-domain antibody library shows a high-propensity to yield non-aggregating binders," Protein Engineering, Design & Selection, 25(6):313-318.
Ill et al. (1997) "Design and construction of a hybrid immunoglobulin domain with properties of both heavy and light chain variable regions," Protein Engineering, 10(8):949-957.
Janssens et al. (2006) "Generation of heavy-chain-only antibodies in mice," Proc. Nat'l. Acad. Sci., 103(41):15130-15135.
Johnson et al. (1997) "Ig VH1 Genes Expressed in B Cell Chronic Lymphocytic Leukemia Exhibit Distinctive Molecular Features," The Journal of Immunology, 158:235-246.
Johnston et al. (2006) "Complete Sequence Assembly and Characterization of the C57BL/6 Mouse Ig Heavy Chain V Region1," J. Immunol., 176:4221-4234.
Kaartinen et al. (1988) "Combinatorial association of V genes: One VH gene codes for three non-cross-reactive monoclonal antibodies each specific for a different antigen (phOXAZOLONE, NP or GAT)," Mol. Immunol., 25(9):859-865.
Kabat and Wu, (1991) "Identical V region amino acid sequences and segments of sequences in antibodies of different specificities. Relative contributions of VH and VL genes, minigenes, and complementarity-determining regions to binding of antibody-combining sites," J. Immunol., 147(5):1709-1719.

(56) References Cited

OTHER PUBLICATIONS

Kantor et al. (1997) "An Unbiased Analysis of VH-D-JH Sequences from B-la, B-1b, and Conventional B Cells," The Journal of Immunology, 158: 1175-1186.
Kaushik et al. (2002) "Novel insight into antibody diversification from cattle," Veterinary Immunology and Immunopathology, 87(3-4):347-350.
Kellermann and Green (2002) "Antibody discovery: the use of transgenic mice to generate human monoclonal antibodies for therapeutics ," Current Opinion in Biotechnology 13:593-597.
Kim et al. (2006) "Expression and relationship of male reproductive ADAMs in mouse," Biology of Reproduction, 74(4):744-750.
Kingzette et al.(1998) "Trans-chromosomal recombination within the Ig heavy chain switch region in B lymphocytes," PNSA, 95(20):11840-11845.
Klebig, (1995) "Ectopic Expression of the Agouti Gene in Transgenic Mice Causes Obesity," Features fo Type II Diabetes, and Yellow Fur, PNAS 92:4728-4732.
Kobayashi and Oyama (2011) "Antibody engineering toward high-sensitivity high-throughput immunosensing of small molecules," The Royal Society of Chemistry, Analyst, 136:642-651 (DOI: 10.1039/c0an00603c).
Kong et al. (2009) "Transgene expression is associated with copy number and cytomegalovirus promoter methylation in transgenic pigs," PLoS One 4(8):1-10.
Kunert et al. (2004) "Characterization of Molecular Features, Antigen-Binding, and in Vitro Properties of IgG and IgM Variants of 4E10, an Anti-HIV Type 1 Neutralizing Monoclonal Antibody," Aids ReSearch and Human Retroviruses, 20(7):755-762.
Kuroiwa et al. (2002) "Cloned transchromosomic calves producing human immunoglobulin," Nat. Biotechnol., 20(9):889-894.
Kuroiwa et al. (2004) "Sequential targeting of the genes encoding immunoglobulin-μ and prion protein in cattle," Nature Genetics, 36:775-780.
Lavial and Pain, (2010) "Chicken embryonic stem cells as a non-mammalian embryonic stem cell model" Develop. Groth Diff., 52(1):101-114.
Leclercq et al. (1989) "A novel germ-like JK transcript starting immediately upstream of JK1," Nucleic Acids Research, 17(17):6809-6819.
Lee et al. (2014) "Complete humanization of the mouse immunoglobulin loci enables efficient therapeutic antibody discovery," Nature Biotechnology, 32(4):356.
Lefranc, (2001) "Nomeclature of the human immunoglobulin lambda (IGL) genes," Experimental and Clinical Immunogenetics, S. Karger Basel C.H., 18(4):242-254.
Lefranc, (2000) "Nomoclature of the Human Immunoglobulin Genes Current Protocols in Immunology," Supplement 40:1.1P.1-A.1P.37.
Lefranc, (2004) Molecular Biology of B Cells. London: Elsevier Academic Press, Ed. Honjo, Chapter 4 pp. 37-59.
Leitzgen et al. (1997) "Assembly of Immunoglobulin Light Chains as a Prerequisite for Secretion," Journal Biological Chemistry., 272(5):3117-3123.
Lin et al. (1990) "Research of Immune Globulin in Mice," Guangzhou Medical Journal, 1:49-50 and English translation.
Little et al. (2000) "Of mice and men: hybridoma and recombinant antibodies.," Immunology Today 21:364-370.
Liu et al. (2014) "Primary Genetic Investigation of a Hyperlipidemia Model: Molecular Characteristics and Variants of the Apolipoprotein E Gene in Mongolian Gerbil," Biomed. Research International, (9 pages).
Lonberg, (2005) "Human antibodies from transgenic animals, Nature Biotechnology," 23(9):1117-1125.
Lovell-Badge (2007) "Many ways to pluripotency," Nature Biotechnology, 25:1114-1116.
MacDonald et al. (2006) "Velocigene Technology Extended to Humanization of Several Megabases of complex Gene Loci," First International MUGEN Conference of Animal Models for Human Immunological Disease, Sep. 10-13, 2006—Athens, Greece, Abstract 21 and Poster, 2 pages original (pp. 3-11 are p. 2 of the original, enlarged).
MacDonald et al. (2014) "Precise and in situ genetic humanization of 6 Mb of mouse immunoglobulin genes," PNAS, 111(14):5147-5152.
Mageed et al. (2001) "Rearrangement of the human heavy chain variable region gene V3-23 in transgenic mice generates antibodies reactive with a range of antigens on the basis of VhCDR3 and residues intrinsic to the heavy chain variable region," Clin Exp Immunol, 123:1-8.
Mahmoud et al. (2011) "Limiting CDR-H3 Diversity Abrogates the Antibody Response to the Bacterial Polysaccharide α 1 →3 Dextran," The Journal of Immunology, 187: 879-886.
Mahmoudi et al. "V region gene analysis of human IgM hybridoma monoclonal anti-Sm antibodies," Lupus, 6:578-589, 1997.
Manis et al. (2002) "Mechanism and control of class-switch recombination," TRENDS in Immunology, 23(1):31-39.
Marasca et al. (2001) "Immunoglobulin Gene Mutations and Frequent Use of VH1-69 and VH4-34 Segments in Hepatitis C VirUS Positive and Hepatitis C VirUS Negative Nodal Marginal Zone B-Cell Lymphoma," American Journal of Pathology, 159(1): 253-261.
Martin and Van Ness, (1989) "Identification of a Germ Line Transcript from the Unrearranged Kappa Gene in Human B Cells," Molecular and Cellular Biology, 9(10):4560-4562.
Martin and Van Ness, (1990) "Initiation and Processing ofTwo Kappa Immunoglobulin Germ Line Transcripts in Mouse B cells," Molecular and Cellular Biology, 10(5):1950-1958.
McGoldrick et al. (2013) "Rodent models of amyotrophic lateral sclerosis," Biochimica et Biophysica Acta, 1832:1421-1436.
Mei et al. (1991) "Vasoactive intestinal peptide hydrolysis by antibody light chains," J. Biol. Chem., 266(24):15571-4.
Miklos et al. (2000) "Salivary gland mucosa-associated lymphoid tissue lymphoma immunoglobulin VH genes show frequent use of V1-69 with distinctive CDR3 features," Blood, 95:3878-3884.
Miller et al. (2003) "Design, Constructio, and in Vitro Analyses of Multivalent Antibodies," J. Immunol., 170:4854-4861.
Mills et al. (1997) "Enhancer complexes located downstream of both human immunoglobulin Calpha genes, Journal of Experimental Medicine,"186(6):845-858.
Mirzabekov et al. (1996) Nucleic Acids Res 24(15): 2998-3004.
Montaño and Morrison, (2002) "Influence of the Isotype of the Light Chain on the Properties of IgG," Journal of Immunology, 168:224-231.
Moran, (2013) "Mouse platforms jostle for slice of humanized antibody market," Nature Biotechnology, 31(4):267-268.
Morrison et al. (1998) "Variable region domain exchange influences the functional properties of igG," J. Immunol., 160:2802-2808.
Mortari et al. (1993) "Human Cord Blood Antibody Repertoire," The Journal of Immunology, 150(4):1348-1357.
Muñoz et al. (2008) "Conventional pluripotency markers are unspecific for bovine embryonic-derived cell-lines," Theriogenology, 69(9):1159-1164.
Muller et al. (1993) "B-Cell Abnormalities in AIDS: Stable and Clonally-Restricted Antibody Response in HIV-1 Infection," Scand. J. Immunol., 38:327-334.
Murphy and Silha (2000) "Unexpected and unexplained phenotypes in transgenic models," Growth Hormone & IGF Research, 10:233-235.
Murphy (2012) Kenneth, Janeway's Immunobiology 8th Edition. New York: Garland Science, Printed in USA., Chapter 5, Sections 5-1 to 5-4, pp. 157-162.
Myszka (1999) "Improving biosensor analysis," J. Mol. Recogn. 12:279-284.
Nagle, Regeneron helps make Sanofi VelocImmune to its "weak pipeline". <http://www.outsourcing-pharma.com> Published Dec. 3, 2007.
News in Brief Article. Big Pharma views for mice, Nature Biotechnology Jun. 2007;25(6):613.
Nicholson et al. (1999) "Antibody Repertoires of four-and Five-Feature Translocus Mice Carrying Human Immunoglobulin Heavy

(56) References Cited

OTHER PUBLICATIONS

Chain and kappa and lambda light chain Yeast Artificial Chromosomes," Journal of Immunology, 163(12):6898-6906.
Niemann et al. (2005) "Transgenic farm animals: present and future, Review of Science Technology," 24(1):285-298.
Nishimura et al. (2004) "Possible Function of the ADAM1a/ADAM2 Fertilin Complex in the Appearance of ADAM 3 on the Sperm Surface," The Journal of Biological Chemistry, 279(33):34957-34962.
Nitschke et al. (2001) "Deletion of the DQ52 element with the Ig heavy chain locus leads to a selective reduction in VDJ recombination and altered D gene usage," J. Immunol., 166:2540-52.
Novotny et al. (1985) "Structural Invariants of Antigen Binding: Comparison of Immunoglobulin VL-VH and VL-VL Domain Dimers," Proc. Nat. Acad. Sci., 82:4592-4596.
Oberdoerffer et al. (2003) "Unidirectional Cre-mediated genetic inversion in mice using the mutant loxP pair lox66/lox71," Nucleic Acids Research, 31(22)(e140):1-7.
Oddo et al. (2003) "Triple-Transgenic Model of Alzheimer's Disease with Plaques and Tangles: Intracellular A and Synaptic Dysfunction," Neuron, 39:409-421.
Paris and Stout, (2010) "Equine embryos and embryonic stem cells: defining reliable markers of pluripotency," Theriogenology, 74(4):516-524.
Parng et al. (1996) "Gene conversion contributes to the Ig light chain diversity in cattle," The Journal of Immunology, 157(12):5478-5486.
Pasqualini and Arap (2004) "Hybridoma-free generation of monoclonal antibodies," Proceedings of the National Academy of Sciences USA, 101(1):257-259.
Pereira et al. (1998) "Cardiolipin binding a light chain from lupus-prone mice," Biochemistry, 37:1430-7.
Perez et al. (2010) "Primary cutaneous B-cell lymphoma is associated with somatically hypermutated immunoglobulin variable genes and frequent use of VH1-69 and VH4-59 segments," British Journal of Dermatology, 162:611-618.
Petitte et al. (2004) "Avian pluripotent stem cells," Mech. of Develop., 121(9):1159-1168.
Pettersson et al. (1990) "A second B cell-specific enhancer 3' of the immunoglobulin heavy-chain locus," Nature, 344(6262):165-168.
Popov et al. (1999) "A Human Immunoglobulin lambda locus is Similarly Well Expressed in Mice and Humans," J. Exp. Med., 189(10):1611-1619.
Pos et al. (2008) "VH1-69 germline encoded antibodies directed towards ADAMTSI3 in patients with acquired thrombotic thrombocytopenic purpura," Journal of Thrombosis & Haemostasis, 7:421-428.
Poueymirou et al (2007) "F0 generation mice fully derived from gene-targeted embryonic stem cells allowing immediate phenotypic analyses," Nat Biotechnol 25, 91-99.
Qi et al. (2005) "A new transgenic rat model of hepatic steatosis and the metabolic syndrome," Hypertension, 45(5):1004-1011.
Ramírez-Solis et al. (1995) "Chromosome engineering in mice," Nature, 378(6558):720-724.
Ramsden et al. (1994) "Conservation of sequence in recombination signal sequence spacers," Nucleic Acids Res., 22(10):1785-1796.
Ravetch et al. (1981) "Structure of the human immunoglobulin mu locus: characterization of embryonic and rearranged J and D genes," Cell, 27:583-591.
Ray (1991) "Ectopic expression of a c-kitW42 minigene in transgenic mice: recapitulation of W phenotypes and evidence for c-kit function in melanoblast progenitors," Genes Dev., 5(12A): 2265-2273.
Reineke (2004) "Antibody Epitope Mapping Using Arrays of Synthetic Peptides," Methods Mol Biol 248:443-463.
Ren e al. (2004) "Silencing of the immunoglobulin heavy chain locus by removal of all eight constant-region genes in a 200-kb region," Genomics, 84:686-695.
Rich et al. (2000) "Advances in surface plasmon resonance biosensor analysis," Curr. Opin. Biotechnol. 11:54-61.
Ristevski (2005) "Making better transgenic models: conditional, temporal, and spatial approaches," Molecular Biotechnology, 29(2):153-163.
Rocca-Serra et al. (1983) "Two monoclonal antibodies against different antigens using the VH germ-line gene," Nature 304:353-5.
Rodriguez et al. (2000) "High-efficiency deleter mice show that FLPe is an alternative to Cre-loxP," Nature Genetics, 25:139-140.
Rojas et al. (2002) "Phage antibody fragments library combining a single human light chain variable region with immune mouse heavy chain variable regions," Biotechnol., 94(3):287-298.
Rudikoff et al. (1982) "Single amino acid substitution altering antigen-binding specificity," PNAS 79:1979-1983.
Sapparapu et al. (2009) "Antigen-specific proteolysis by hybrid antibodies containing promiscuous proteolytic light chains paired with an antigen-binding heavy chain," J. Biol. Chem., 284(36):24622-24633.
Sasso et al. (1993) "A Fetally Expressed Immunoglobulin $V_H1$ Gene Belongs to a Complex Set of Alleles," Journal of Clinical Investigation, 91:2358-2367.
Sasso et al. (1996) "Expression of the Immunoglobulin VH Gene 51p1 Is Proportional to Its Germline Gene Copy Number" Journal of Clinical Investigation, 97(9):2074-2080.
Sasso et al., (1990) "Prevalence and Polymorphism of Human $V_h3$ Genes," Journal of Immunology, 145(8):2751-2757.
Schelonka et al. (2005) "A Single Dry Gene Segment Creates Its Own Unique CDR-H3 Repertoire and Is Sufficient for B cell Development and Immune Functions," Journal of Immunology, 175:6624-6632.
Schlissel and Baltimore (1989) "Activation of Immunoglobulin Kappa Gene Rearrangement Correlates with Induction of Germline Kappa Gene Transcription," Cell, 58:1001-1007.
Schultz et al. (2012) "Humanized mice for immune system investigation: progress, promise and challenges," Nature Reviews Immunology, 12:786-798.
Schulze et al. (2006) "Derivation, Maintenance, and Characterization of Rat Embryonic Stem Cells in Vitro," Methods in Molecular Biology, 329:45-58.
Scott (2007) "Mice with a human touch," Nature Biotechnology, 25(10):1075-7.
Seals and Courtneidge (2003) "The ADAMs family of metalloproteases: multidomain; proteins with multiple functions," Genes and Development, 17(1):7-30.
Sen and Baltimore (1986) "Multiple nuclear factors interact with the immunoglobulin enhancer sequences," Cell, 46(5):705-716.
Sepulveda et al. (2003) "Binders Based on Dimerised Immunoglobulin VH Domains," J. Mol. Biol., 333:355-365.
Shmerling et al. (2005) "Strong and ubiquitous expression of transgenes targeted into the β-actin locus by Cre/lox cassette replacement," Genesis, 42(5):229-235.
Shi et al. (2006) J. Immunol. Methods 314:9-20.
Schiffer et al. (1973) "Structure of a λ-Type Bence-Jones Protein at 3.5-Å," Biochemistry, 12:4620-4631.
Sibilia et al. (1997) "Structural Analysis of Human Antibodies to Proteinase 3 from Patients with Wegener Granulomatosis," Journal of Immunology, 159:712-719.
Sigmund (2000) "Viewpoint: Are Studies in Genetically Altered Mice Out of Control?" Arterioscler. Thomb. Vasc. Biol., 20(6):1425-1429.
Simon and Rajewsky (1990) "Antibody domain mutants demonstrate autonomy of the antigen binding site," EMBO Journal., 9(4):1051-1056.
Smith, (2002) "Gene transfer in higher animals: theoretical considerations and key concepts," Journal of Biotechnology, 99(1):1-22.
Solomon et al. (1998) "Light chain-associated amyloid deposits comprised of a novel κ constant domain," PNAS, 95:9547-9551.
Song et al. (2000) "Light chain of natural antibody plays a dominant role in protein antigen binding," Biochem. Biophys. Res. Comm., 268:390-394.
Souroujon et al. (1989) "Polymorphisms in Human H Chain V Region Genes From the VHIII Gene Family," Journal of Immunology, 143(2):706-711.

(56) References Cited

OTHER PUBLICATIONS

Stamatopoulos et al. (1997) "Follicular lymphoma immunoglobulin κ light chains are affected by the antigen selection process, but to a lesser degree than their partner heavy chains," British J. Haematology, 96:132-146.

Stevens et al. (2006) "Velocimmune: Humanization of Immunoglobulin Loc Using Velocigene Technology," First International MUGEN Conference of Animal Models for Human Immunological Disease, Sep. 10-13, 2016—Athens, Greece, Abstract 4 and Poster, 2 pages original (pp. 3-11 are p. 2 of the original, enlarged).

Sui et al. (2009) "Structural and functional bases for broad-spectrum neutralization of avian and human influenza A viruses," Nature Structural & Molecular Biology, 16(3):265-273.

Sun et al. (1994) "Antigen recognition by an antibody light chain," J. Biol. Chem., 269(1):734-738.

Suzuki et al. (1995) "Representation of Rearranged $V_H$ Gene Segments in the Human Adult Antibody Repertoire," Journal of Immunology, 154:3902-3911.

Swarthout et al. (2011) "Zinc Finger Nucleases: A new era for transgeenic animals," Annals of Neurosciences, 18(1):25-28.

Szent-Gyorgy et al. (2013) "Malachite Green Mediates Homodimerization of Antibody $V_L$ Domains to Form a Fluorescent Ternary Complex with Singular Symmetric Interfaces," J. Mol. Biol., 425:4595-4613.

Taki et al. (1993) "Targeted Insertion of a Variable Region Gene into the Immunoglobuliin Heavy Chain Locus," Science, 262:1268-1271.

Taylor (1992) "A transgenic mouse that expresses a diversity of human sequence heavy and light chain immunoglobulins," Nucl. Acids Res. 20:6287-6295).

Timetable for Mouse ES Cells course at Wellcome Trust Sanger Institute Oct. 26, 2009-Nov. 8, 2009 (black and white), 5 pages original (pp. 6-13 are pp. 1-5 of the original, enlarged).

Timetable for Mouse ES Cells course at Wellcome Trust Sanger Institute Oct. 26, 2009-Nov. 8, 2009 (greyscale), 5 pages original (pp. 6-13 are pp. 1-5 of the original, enlarged).

Tomer (2000) "Characterization of a discontinuous epitope of the human immunodeficiency virus ~HIV! core protein p24 by epitope excision and differential chemical modification followed by mass spectrometric peptide mapping analysis," Protein Science: 9:487-496 (first named author is Hochleitner).

Tonegawa (1983) "Somatic generation of antibody diversity," Nature, 302(5909):575-581.

Torres and Kuhn (1997) Laboratory Protocols for Conditional Gene Targeting, 37-40.

Tsybovsky et al. (2004) "Folding and stabiilty of chimeric immunofusion VL-barstar," Biochem (Moscow), 69(9):939-948.

Tuaillon et al. (1993) "Human immunoglobulin heavy-chain minilocus recombination in transgenic mice: Gene-segment use in μ, and γ transcripts," PNAS, 90:2734-2743.

Tuaillon (2000) "Repertoire analysis in human immunoglobulin heavy chain minilocus transgenic, [mu]MT/ [mu]MT mice," Molecular Immunology, 37(5):221-231.

Valenzuela et al (2003) "High-throughput engineering of the mouse genome coupled with high-resolution expression analysis," Nat. Biotechnol. 21:652-659.

Van Den Beucken et al. (2001) "Building novel binding ligands to B7.1 and B7.2 based on human antibody single variable light chain domains," J. Mol. Immunol., 310:591-601.

Van Ness et al. (1981) "Transcription of the unrearranged mouse C kappa locus: sequence of the initiation region and comparison of activity with a rearranged V kappa-C kappa gene," Cell, 27:593-602.

Verkoczy et al. (2010) "Autoreactivity in an HIV-1 broadly reactive neutralizing antibody variable region heavy chain induces immunologic tolerance," Proc. Natl. Acad. Sci. U.S.A., 107(1): 181-186.

Wagner et al. (1994) "Antibodies generated from human immunoglobulin miniloci in transgenic mice," Nucleic Acids Research, 22(8):1389-1393.

Wagner et al. (1994) "The diversity of antigen-specific monoclonal antibodies form transgenic mice bearing human immunoglobulin gene miniloci," Eur. J. Immunol., 24:2673-2681.

Wallace et al. (2007) "Manipulating the mouse genome to engineer precise functional syntenic replacements with human sequence," Cell, 128(1):197-209.

Wang and Palese (2009) "Universal epitopes of influenza virus hemagglutinins?," Nature Structural & Molecular Biology, 16(3):233-234.

Warren and Nie (1998) Science 281: 2016-2018.

Watson and Crick (2002) Molekulyarnaya biotekhnologiya. Printsipy i primeneniye, Moscow Mir., 45-47 and English translation.

Williams et al. (1996) "Sequence Evolution of the Human Germline V lambda Repertoire," J. Mol. Biol., 264(2):220-232.

Xu et al. (2000) "Diversity in the CDR3 Region of VHIs Sufficient for Most Antibody Specificities," Immunity, 13:37-45.

Yamada et al. (1991) "Preferential Utilization of Specific Immunoglobulin Heavy Chain Diversity and Joining Segments in Adult Human Peripheral Blood B Lymphocytes," Journal of Experimental Medicine, 173:395-407.

Yantha et al. (2010) "Unexpected Acceleration of Type 1 Diabetes by Transgenic Expression of B7-H1 in NOD Mouse Peri-Islet Glia," Diabetes, 59:2588-2596.

Yu et al. (2008) "Interaction between Bevacizumab and Murine Vegf-A: a Reassessment," Investigative Ophthalmology & Visual Science, 49(2):522-527.

Zheng et al. (2000) "Engineering mouse chromosomes with Cre-IoxP: range, efficiency, and somatic applications," Molecular and Cellular Biology, 20(2):648-655.

Zou et al. (1994) Cre-IoxP-mediated gene replacement: a mouse strain producing humanized antibodies, Current Biology, 4:1099-1103.

Zou et al. (2007) "Heavy chain-only antibodies are spontaneously produced in light chain-deficient mice," J. Exp. Med. 204(13):3271-3283.

Zhou et al., (2009) "Developing tTA transgenic rats for inducible and reversible gene expression," International Journal of Biological Sciences, 5:171-181.

Communication in Cases for which No Other Form is Applicable for PCT/US2012/026416, 9 pages (Jun. 7, 2013).

Communication in Cases for Which No Other Form Is Applicable for PCT/US2012/069981 , 18 pages (Jul. 3, 2013).

Declaration Under C.F.R. § 1.132 Dr. Andrew Murphy Dated Jul. 16, 2014.

Declaration Under C.F.R. § 1.132 Dr. Jürgen Roes Dated Jul. 19, 2014.

Declaration Under C.F.R. § 1.131 Inventors: Lynn Macdonald, Cagan Gurer, Karolina Hosiawa, Sean Stevens, and Andrew Murphy Dated Dec. 1, 2015.

EP Examination Report with respect to EP 11741730.3 dated Jan. 23, 2015.

European Search Report with respect to EP12192727, dated Mar. 7, 2013.

European Search Report with respect to EP12195716, dated Jan. 29, 2013.

Extended European Search Report with respect to EP14154918.8, dated Aug. 27, 2014.

Extended European Search Report with respect to EP14176593.3, dated Nov. 19, 2014.

Extended European Search Report with respect to EP15173007.4, dated Oct. 5, 2015.

Final Office Action with Respect to U.S. Appl. No. 13/756,889, dated Nov. 6, 2015.

Non-Final Office Action with Respect to U.S. Appl. No. 13/756,889, dated Dec. 1, 2016.

International Search Report & Written Opinion with respect to PCT/US2011/041366, dated Sep. 22, 2011.

International Search Report & Written Opinion with respect to PCT/US2011/041370, dated Sep. 22, 2011.

International Search Report & Written Opinion with respect to PCT/US2012/026416, dated Jun. 25, 2012.

International Search Report & Written Opinion with respect to PCT/US2012/069981, dated Mar. 20, 2013.

(56) References Cited

OTHER PUBLICATIONS

International Search Report & Written Opinion with respect to PCT/US2013/024295, dated Apr. 24, 2013.
International Search Report & Written Opinion with respect to PCT/US2011/046196, dated Oct. 17, 2011.
International Search Report & Written Opinion with respect to PCT/US2015/021884, dated Oct. 13, 2015.
International Search Report & Written Opinion with respect to PCT/US2012/060487, dated Feb. 1, 2013.
Summons to Attend Oral Proceedings with respect to EP 11741730.3 mailed Sep. 28, 2015.
Invitation to Pay Additional Fees and, Where Applicable, Protest Fee for PCT/US2015/021892, mailed Aug. 10, 2015.
International Search Report & Written Opinion with respect to PCT/US2015/021892, dated Nov. 4, 2015.
Statement of Relatedness under MPEP 2001.06 with Respect to U.S. Appl. No. 15/497,075, dated Dec. 14, 2017.
Huang et al. (1994) "Comparison of Crystal Structures of Two Homologous Proteins: Structural Origin of Altered Domain Interactions in Immunoglobulin Light-Chain Dimers," Biochemistry, 33:14848-14857.
Murphy Slide Deck, Slide Presentation dated Nov. 3, 2009, "BAC-based Modifications of the Mouse Genome: The Big and the Backward," slides 1-57.
Science Magazine Careers http://www.sciencemag.org/careers/2007/03/mastering-your-phd-making-most-conference, last accessed Nov. 15, 2016.
Female Science Professor https://science-professor.blogspot.com/2009/04/photo-shooters.html; posted Apr. 17, 2009; last accessed May 26, 2017.
J.M. Korhonen, https://jmkorhonen.net/2012/06/25/is-it-ok-to-record-conference-presentations-reconsidering-fair-use-and-electronic-note-taking; posted Jun. 25, 2012; last accessed May 26, 2017.
Statement of Relatedness under MPEP 2001.06 with Respect to U.S. Appl. No. 15/497,075, dated Aug. 13, 2018.
Almagro and Fransson (2008) "Humanization of antibodies," Frontiers in Bioscience, 13:1619-1633.
Bispecific monoclonal antibody, From Wikipedia, the free encyclopedia, pp. 1-5; downloaded on Mar. 19, 2019, https://en.wikipedia.org/wiki/Bispecific monoclonal antibody.
Roussel et al. (1999) "The structure of an entire noncovalent immunoglobulin kappa light-chain dimer (Bence-Jones protein) reveals a weak and unusual constant domains association," Eur. J. Biochem., 260:192-199.
Tian et al. (2016) "Induction of HIV Neutralizing Antibody Lineages in Mice with Diverse Precursor Repertoires," Cell, 166:1471-1484.
Statement of Relatedness under MPEP 2001.06 with Respect to U.S. Appl. No. 15/497,075 dated Sep. 27, 2019.
Statement of Relatedness under MPEP 2001.06 with Respect to U.S. Appl. No. 15/497,075, dated Jun. 30, 2020.
Mendez et al. (1997) "Functional transplant of megabase human immunoglobulin loci recapitulates human antibody response in mice," Nature, 15:146-156.
Statement of Relatedness under MPEP 2001.06 with Respect to U.S. Appl. No. 15/497,043, dated Oct. 22, 2020.

\* cited by examiner

Rearranged Human Vκ-Jκ | Mouse IgG1

```
2E  TGTCAACAGGCTAACAGTTCCCGTACACTTTTGGCCAGGGGACCAAGCTGGAGATCAAAC..CCAAAACGACACCCCCATCTGTCTATCCA
2H  TGCATGCAAGCTCTACAAAtttcGTGACGTTCGGCCAAGGGACCAAGGTGGAAATCAAAC..CCAAAACGACACCCCCATCTGTCTATCCA
3D  TGTCAGCAGCGTAGCcccgtt...TCACTTTCGGCGGAGGGACCAAGGTGGAGATCAAAC..CCAAAACGACACCCCCATCTGTCTATCCA
5D  TGTCTACAACATGATAATT......GGACGTTCGGCCAAGGGACCAAGGTGGAAATCAAAC..CCAAAACGACACCCCCATCTGTCTATCCA
```

Rearranged Human Vκ-Jκ | Mouse IgG2A/2C

```
1E  TGCCAACAGTATAATACCC......TCACTTTCGGCGGAGGGACCAAGGTGGAGATCAAAC..CCAAAACAACAGCCCCATCGGTCGTCTATC
2H  TGTCAACAGCTTAATAGTTACCCTtTCACTTTCGGCGGAGGGACCAAGGTGGAGATCAAAC..CCAAAACAACAGCCCCATCGGTCGTCTATC
1G  TGTCAAAGTATAACAGTGCCCCTCaCACTTTTCGGCGGAGGGACCAAGGTGGAGATCAAAC..CCAAAACAACAGCCCCATCGGTCGTCTATC
1C  TGTCAGCAGTATGGTAGCTCA...CTCACTTTCGGCGGAGGGACCAAGGTGGAGATCAAAC..CCAAAACAACAGCCCCATCGGTCGTCTATC
3A  TGTCAGCAATATTATAGTACTCCGATCACCTTCGGCCAAGGGACCAAGGTGGAGATCAAAC..CCAAAACAACAGCCCCATCGGTCGTCTATC
4B  TGTCTACAACATGATAATTTCCCGTACACTTTTGGCCAGGGGACCAAGCTGGAGATTAAAC..CCAAAACAACAGCCCCATCGGTCGTCTATC
5A  TGTCTACAACATGATAATTTCCCGTACACTTTTGGCCAGGGGACCAAGCTGGAGATCAAAC..CCAAAACAACAGCCCCATCGGTCGTCTATC
```

Rearranged Human Vκ-Jκ | Mouse IgG3

```
1A  TGCCAGCAATATTATAGTACCCTCCCACCTTCGGCCAAGGGACCACGACTGGAGATCAAAC..CTACAACAACAGCCCCATCTGTCTATC
4C  TGTCAGCAATATTATAGTACTgggccCACTTTTGGCCAAGGGACCAAGCTGGAGATCAAAC..CTACAACAACAGCCCCATCTGTCTATC
```

FIG. 9

MICE THAT MAKE $V_L$ BINDING PROTEINS

CROSS-REFERENCE TO RELATED APPLICATIONS

This application is a continuation of U.S. Non-Provisional Application Ser. No. 14/135,510 filed 19 Dec. 2013, now U.S. Pat. No. 9,686,970 issued 27 Jun. 2017, which application is a divisional of U.S. Non-Provisional Application Ser. No. 13/195,951 filed 02 Aug. 2011, now U.S. Pat. No. 9,516,868 issued 13 Dec. 2016, which application claims the benefit under 35 USC §119(e) of U.S. Provisional Application Serial No. 61/369,909, filed 02 Aug. 2010, each of which applications is hereby incorporated by reference.

SEQUENCE LISTING

A Sequence Listing in the form of a text file entitled, "2017-04-24-1200DIV3-US-SEQ-LIST-ST25.txt," created on Apr. 24, 2017, (size 8 Kb) is incorporated herein by reference in its entirety.

FIELD OF INVENTION

Immunoglobulin-like binding proteins comprising an immunoglobulin heavy chain constant region fused with an immunoglobulin light chain variable domain are provided, as well as binding proteins having an immunoglobulin light chain variable domain fused to a light chain constant domain and an immunoglobulin light chain variable domain fused to a heavy chain constant domain. Cells expressing such binding proteins, mice that make them, and related methods and compositions are also provided.

BACKGROUND

Antibodies typically comprise a tetrameric structure having two identical heavy chains that each comprise a heavy chain constant region ($C_H$) fused with a heavy chain variable domain ($V_H$) associated with a light chain constant region ($C_L$) fused with a light chain variable domain ($V_L$). For a typical human IgG, an antibody molecule is approximately about 150 kDa to about 170 kDa in size (e.g., for IgG3, which comprises a longer hinge region), depending on the subclass of IgG (e.g., IgG1, IgG3, IgG4) and (varying) length of the variable region.

In a typical antibody, $V_H$ and $V_L$ domains associate to form a binding site that binds a target antigen. Characteristics of the antibody with respect to affinity and specificity therefore can depend in large part on characteristics of the $V_H$ and $V_L$ domains. In typical antibodies in humans and in mice, $V_H$ domains couple with either λ or κ $V_L$ domains. It is also known, however, that $V_L$ domains can be made that specifically bind a target antigen in the absence of a cognate $V_H$ domain (e.g., a $V_H$ domain that naturally expresses in the context of an antibody and is associated with the particular $V_L$ domain), and that $V_H$ domains can be isolated that specifically bind a target antigen in the absence of a cognate $V_L$ domain. Thus, useful diversity in immunoglobulin-based binding proteins is generally conferred by recombination leading to a particular $V_H$ or $V_L$ (and somatic hypermutation, to the extent that it occurs), as well as by combination of a cognate $V_H$/$V_L$ pair. It would be useful to develop compositions and methods to exploit other sources of diversity.

There is a need in the art for binding proteins based on immunoglobulin structures, including immunoglobulin variable regions such as light chain variable regions, and including binding proteins that exhibit enhanced diversity over traditional antibodies. There is also a need for further methods and animals for making useful binding proteins, including binding proteins that comprise diverse light chain immunoglobulin variable region sequences. Also in need are useful formats for immunoglobulin-based binding proteins that provide an enhanced diversity of binding proteins from which to choose, and enhanced diversity of immunoglobulin variable domains, including compositions and methods for generating somatically mutated and clonally selected immunoglobulin variable domains for use, e.g., in making human therapeutics.

SUMMARY

In one aspect, binding proteins are described that comprise immunoglobulin variable domains that are derived from light chain (i.e., kappa (κ) and/or lambda (λ)) immunoglobulin variable domains, but not from full-length heavy chain immunoglobulin variable domains. Methods and compositions for making binding proteins, including genetically modified mice, are also provided.

In one aspect, nucleic acids constructs, cells, embryos, mice, and methods are provided for making proteins that comprise one or more κ and/or λ light chain variable region immunoglobulin sequences and an immunoglobulin heavy chain constant region sequence, including proteins that comprise a human κ or λ light chain variable domain and a human or mouse heavy chain constant region sequence.

In one aspect, a mouse is provided, comprising an immunoglobulin heavy chain locus comprising a replacement of one or more immunoglobulin heavy chain variable region ($V_H$) gene segments, heavy chain diversity ($D_H$) gene segments, and heavy chain joining ($J_H$) gene segments at an endogenous mouse immunoglobulin heavy chain locus with one or more light chain variable region ($V_L$) gene segments and one or more light chain joining region ($J_L$) gene segments.

In one aspect, a mouse is provided, comprising an immunoglobulin heavy chain locus that comprises a replacement of all or substantially all $V_H$, $D_H$, and $J_H$ gene segments with one or more $V_L$ gene segments and one or more $J_L$ gene segments to form a $V_L$ gene segment sequence at an endogenous heavy chain locus ($VL_H$ locus), wherein the $VL_H$ locus is capable of recombining with an endogenous mouse $C_H$ gene to form a rearranged gene that is derived from a $V_L$ gene segment, a $J_L$ gene segment, and an endogenous mouse $C_H$ gene.

In one embodiment, the $V_L$ segments are human $V_L$. In one embodiment, the $J_L$ segments are human $J_L$. In a specific embodiment, the $V_L$ and $J_L$ segments are human $V_L$ and human $J_L$ segments.

In one embodiment, all or substantially all $V_H$, $D_H$, and $J_H$ gene segments are replaced with at least six human Vκ gene segments and at least one Jκ gene segment. In one embodiment, all or substantially all $V_H$, $D_H$, and $J_H$ gene segments are replaced with at least 16 human Vκ gene segments (human Vκ) and at least one Jκ gene segment. In one embodiment, all or substantially all $V_H$, $D_H$, and $J_H$ gene segments are replaced with at least 30 human Vκ gene segments and at least one Jκ gene segment. In one embodiment, all or substantially all $V_H$, $D_H$, and $J_H$ gene segments are replaced with at least 40 human Vκ gene segments and at least one Jκ gene segment. In one embodiment, the at least one Jκ gene segment comprises two, three, four, or five human Jκ gene segments.

In one embodiment, the $V_L$ segments are human Vκ segments. In one embodiment, the human Vκ segments comprise 4-1, 5-2, 7-3, 2-4, 1-5, and 1-6. In one embodiment, the κ $V_L$ comprise 3-7, 1-8, 1-9, 2-10, 3-11, 1-12, 1-13, 2-14, 3-15, 1-16. In one embodiment, the human Vκ segments comprise 1-17, 2-18, 2-19, 3-20, 6-21, 1-22, 1-23, 2-24, 3-25, 2-26, 1-27, 2-28, 2-29, and 2-30. In one embodiment, the human Vκ segments comprise 3-31, 1-32, 1-33, 3-34, 1-35, 2-36, 1-37, 2-38, 1-39, and 2-40.

In one embodiment, the $V_L$ segments are human Vκ segments and comprise 4-1, 5-2, 7-3, 2-4, 1-5, 1-6, 3-7, 1-8, 1-9, 2-10, 3-11, 1-12, 1-13, 2-14, 3-15, and 1-16. In one embodiment, the Vκ segments further comprise 1-17, 2-18, 2-19, 3-20, 6-21, 1-22, 1-23, 2-24, 3-25, 2-26, 1-27, 2-28, 2-29, and 2-30. In one embodiment, the Vκ segments further comprise 3-31, 1-32, 1-33, 3-34, 1-35, 2-36, 1-37, 2-38, 1-39, and 2-40.

In one embodiment, the $V_L$ segments are human Vλ segments and comprise a fragment of cluster A of the human λ light chain locus. In a specific embodiment, the fragment of cluster A of the human λ light chain locus extends from hVλ3-27 through hVλ3-1.

In one embodiment, the $V_L$ segments comprise a fragment of cluster B of the human λ light chain locus. In a specific embodiment, the fragment of cluster B of the human λ light chain locus extends from hVλ5-52 through hVλ1-40.

In one embodiment, the $V_L$ segments comprise a human λ light chain variable region sequence that comprises a genomic fragment of cluster A and a genomic fragment of cluster B. In a one embodiment, the human λ light chain variable region sequence comprises at least one gene segment of cluster A and at least one gene segment of cluster B.

In one embodiment, the $V_L$ segments comprise at least one gene segment of cluster B and at least one gene segment of cluster C.

In one embodiment, the $V_L$ segments comprise hVλ 3-1, 4-3, 2-8, 3-9, 3-10, 2-11, and 3-12. In a specific embodiment, the $V_L$ segments comprise a contiguous sequence of the human λ light chain locus that spans from Vλ3-12 to Vλ3-1. In one embodiment, the contiguous sequence comprises at least 2, 3, 4, 5, 6, 7, 8, 9, 10, 11 or 12 hVλs. In a specific embodiment, the hVλs include 3-1, 4-3, 2-8, 3-9, 3-10, 2-11, and 3-12. In a specific embodiment, the hVλs comprises a contiguous sequence of the human λ locus that spans from Vλ3-12 to Vλ3-1.

In one embodiment, the hVλs comprises 13 to 28 or more hVλs. In a specific embodiment, the hVλs include 2-14, 3-16, 2-18, 3-19, 3-21, 3-22, 2-23, 3-25, and 3-27. In a specific embodiment, the hVλs comprise a contiguous sequence of the human λ locus that spans from Vλ3-27 to Vλ3-1.

In one embodiment, the $V_L$ segments comprise 29 to 40 hVλs. In a specific embodiment, the $V_L$ segments comprise a contiguous sequence of the human λ locus that spans from Vλ3-29 to Vλ3-1, and a contiguous sequence of the human λ locus that spans from Vλ5-52 to Vλ1-40. In a specific embodiment, all or substantially all sequence between hVλ1-40 and hVλ3-29 in the genetically modified mouse consists essentially of a human λ sequence of approximately 959 bp found in nature (e.g., in the human population) downstream of the hVλ1-40 gene segment (downstream of the 3' untranslated portion), a restriction enzyme site (e.g., PI-SceI), followed by a human λ sequence of approximately 3,431 bp upstream of the hVλ3-29 gene segment found in nature.

In one embodiment, the Jκ is human and is selected from the group consisting of Jκ1, Jκ2, Jκ3, Jκ4, Jκ5, and a combination thereof. In a specific embodiment, the Jκ comprises Jκ1 through Jκ5.

In one embodiment, the $V_L$ segments are human Vλ segments, and the Jκ gene segment comprises an RSS having a 12-mer spacer, wherein the RSS is juxtaposed at the upstream end of the Jκ gene segment. In one embodiment, the $V_L$ gene segments are human Vλ and the $VL_H$ locus comprises two or more Jκ gene segments, each comprising an RSS having a 12-mer spacer wherein the RSS is juxtaposed at the upstream end of each Jκ gene segment.

In a specific embodiment, the $V_L$ segments comprise contiguous human κ gene segments spanning the human κ locus from Vκ4-1 through Vκ2-40, and the $J_L$ segments comprise contiguous gene segments spanning the human κ locus from Jκ1 through Jκ5.

In one embodiment, where the $V_L$ segments are Vλ segments and no $D_H$ segment is present between the $V_L$ segments and J segments, the $V_L$ segments are flanked downstream (i.e., juxtaposed on the downstream side) with 23-mer RSS, and Jκ segments if present or Jλ segments if present are flanked upstream (i.e., juxtaposed on the upstream side) with 12-mer RSS.

In one embodiment, where the V gene segments are Vκ gene segments and no $D_H$ gene segment is present between the V gene segments and J gene segments, the Vκ gene segments are each juxtaposed on the downstream side with a 12-mer RSS, and Jκ segments if present or Jλ segments if present are each juxtaposed on the upstream side with a 23-mer RSS.

In one embodiment, the mouse comprises a rearranged gene that is derived from a $V_L$ gene segment, a $J_L$ gene segment, and an endogenous mouse $C_H$ gene. In one embodiment, the rearranged gene is somatically mutated. In one embodiment, the rearranged gene comprises 1, 2, 3, 4, 5, 6, 7, 8, 9, 10 or more N additions. In one embodiment, the N additions and/or the somatic mutations observed in the rearranged gene derived from the $V_L$ segment and the $J_L$ segment are 1.5-fold, 2-fold, 2.5-fold, 3-fold, 3.5-fold, 4-fold, 4.5-fold, or at least 5-fold more than the number of N additions and/or somatic mutations observed in a rearranged light chain variable domain (derived from the same $V_L$ gene segment and the same $J_L$ gene segment) that is rearranged at an endogenous light chain locus. In one embodiment, the rearranged gene is in a B cell that specifically binds an antigen of interest, wherein the B cell binds the antigen of interest with a $K_D$ in the low nanomolar range or lower (e.g., a $K_D$ of 10 nanomolar or lower). In a specific embodiment, the $V_L$ segment, the $J_L$ segment, or both, are human gene segments. In a specific embodiment, the $V_L$ and $J_L$ segments are human κ gene segments. In one embodiment, the mouse $C_H$ gene is selected from IgM, IgD, IgG, IgA and IgE. In a specific embodiment, the mouse IgG is selected from IgG1, IgG2A, IgG2B, IgG2C and IgG3. In another specific embodiment, the mouse IgG is IgG1.

In one embodiment, the mouse comprises a B cell, wherein the B cell makes from a locus on a chromosome of the B cell a binding protein consisting essentially of four polypeptide chains, wherein the four polypeptide chains consist essentially of (a) two identical polypeptides that comprise an endogenous mouse $C_H$ region fused with a $V_L$; and, (b) two identical polypeptides that comprise an endogenous mouse $C_L$ region fused with a $V_L$ region that is cognate with respect to the $V_L$ region that is fused with the mouse $C_H$ region, and, in one embodiment, is a human (e.g., a human κ) $V_L$ region. In one embodiment, the $V_L$ region fused to the endogenous mouse $C_H$ region is a human $V_L$ region. In a specific embodiment, the human $V_L$ region fused with the mouse $C_H$ region is a Vκ region. In a specific embodiment, the human $V_L$ region fused with the mouse $C_H$ region is identical to a V region encoded by a rearranged human germline light chain nucleotide sequence. In a specific embodiment, the human $V_L$ region fused to the mouse $C_H$ region comprises two, three, four, five, six, or more somatic hypermutations. In one embodiment, the human $V_L$ region fused to the mouse $C_H$ region is encoded by a rearranged gene that comprises 1, 2, 3, 4, 5, 6, 7, 8, 9, or 10 or more N additions.

In one embodiment, at least 50% of all IgG molecules made by the mouse comprise a polypeptide that comprises an IgG isotype $C_H$ region and a $V_L$ region, wherein the length of said polypeptide is no longer than 535, 530, 525, 520, or 515 amino acids. In one embodiment, at least 75% of all IgG molecules comprise the polypeptide recited in this paragraph. In one embodiment, at least 80%, 85%, 90%, or 95% of all IgG molecules comprise the polypeptide recited in this paragraph. In a specific embodiment, all IgG molecules made by the mouse comprise a polypeptide that is no longer than the length of the polypeptide recited in this paragraph.

In one embodiment, the mouse makes a binding protein comprising a first polypeptide that comprises an endogenous mouse $C_H$ region fused with a variable domain encoded by a rearranged human V gene segment and a J gene segment but not a $D_H$ gene segment, and a second polypeptide that comprises an endogenous mouse $C_L$ region fused with a V domain encoded by a rearranged human V gene segment and a J gene segment but not a $D_H$ gene segment, and the binding protein specifically binds an antigen with an affinity in the micromolar, nanomolar, or picomolar range. In one embodiment, the J segment is a human J segment (e.g., a human κ gene segment). In one embodiment, the human V segment is a human Vκ segment. In one embodiment, the variable domain that is fused with the endogenous mouse $C_H$ region comprises a greater number of somatic hypermutations than the variable region that is fused with the endogenous mouse $C_L$ region; in a specific embodiment, the variable region fused with the endogenous mouse $C_H$ region comprises about 1.5, 2-, 3-, 4-, or 5-fold or more somatic hypermutations than the V region fused to the endogenous mouse $C_L$ region; in a specific embodiment, the V region fused with the mouse $C_H$ region comprises at least 6, 7, 8, 9, 10, 11, 12, 13, 14, or 15 or more somatic hypermutations than the V region fused with the mouse $C_L$ region. In one embodiment, the V region fused with the mouse $C_H$ region is encoded by a rearranged gene that comprises 1, 2, 3, 4, 5, 6, 7, 8, 9, or 10 or more N additions.

In one embodiment, the mouse expresses a binding protein comprising a first light chain variable domain ($V_L1$) fused with an immunoglobulin heavy chain constant region sequence and a second light chain variable domain ($V_L2$) fused with an immunoglobulin light chain constant region, wherein $V_L1$ comprises a number of somatic hypermutations that is about 1.5- to about 5-fold higher or more than the number of somatic hypermutations present in $V_L2$. In one embodiment, the number of somatic hypermutations in $V_L1$ is about 2- to about 4-fold higher than in $V_L2$. In one embodiment, the number of somatic hypermutations in $V_L1$ is about 2- to about 3-fold higher than in $V_L2$. In one embodiment, $V_L1$ is encoded by a sequence that comprises 1, 2, 3, 4, 5, 6, 7, 8, 9, or 10 or more N additions.

In one aspect, a genetically modified mouse is provided that expresses an immunoglobulin that consists essentially of the following polypeptides: a first two identical polypeptides that each consists essentially of a $C_H$ region fused with a variable domain that is derived from gene segments that consist essentially of a $V_L$ gene segment and a $J_L$ gene segment, and a second two identical polypeptides that each consists essentially of a $C_L$ region fused with a variable domain that is derived from gene segments that consist essentially of a $V_L$ segment and a $J_L$ segment.

In a specific embodiment, the two identical polypeptides that have the $C_H$ region have a mouse $C_H$ region.

In a specific embodiment, the two identical polypeptides that have the $C_L$ region have a mouse $C_L$ region.

In one embodiment, the variable domain fused with the $C_L$ region is a variable domain that is cognate with the variable domain fused to the $C_H$ region.

In one embodiment, the variable domain that is fused with the endogenous mouse $C_H$ region comprises a greater number of somatic hypermutations than the variable domain that is fused with the endogenous mouse $C_L$ region; in a specific embodiment, the variable domain fused with the endogenous mouse $C_H$ region comprises about 1.5-fold, 2-fold, 2.5-fold, 3-fold, 3.5-fold, 4-fold, 4.5-fold, or 5-fold or more somatic hypermutations than the variable domain fused to the endogenous mouse $C_L$ region. In one embodiment, the variable domain fused with the endogenous mouse $C_L$ region is encoded by a gene that comprises 1, 2, 3, 4, 5, 6, 7, 8, 9, 10 or more N additions.

In one embodiment, one or more of the V segments and the J segments are human gene segments. In a specific embodiment, both the V segments and the J segments are human κ gene segments. In another specific embodiment, both of the V segments and the J segments are human λ gene segments. In one embodiment, the V segments and the J segments are independently selected from human κ and human λ gene segments. In a specific embodiment, the V segments are Vκ segments and the J segments are Jλ segments. In another specific embodiment, the V segments are Vλ segments and the J segments are Jκ segments.

In one embodiment, one or more of the variable domains fused with the $C_L$ region and the variable domains fused with the $C_H$ region are human variable domains. In a specific embodiment, the human variable domains are human Vκ domains. In another specific embodiment, the human variable domains are Vλ domains. In one embodiment, the human domains are independently selected from human Vκ and human Vκ domains. In a specific embodiment, the human variable domain fused with the $C_L$ region is a human Vλ domain and the human variable domain fused with the $C_H$ region is a human Vκ domain. In another embodiment, the human variable domain fused with the $C_L$ region is a human Vκ domain and the human variable domain fused with the $C_H$ is a human Vλ domain.

In one embodiment, the $V_L$ gene segment of the first two identical polypeptides is selected from a human Vκ segment and a human Vκ segment. In one embodiment, the $V_L$ segment of the second two identical polypeptides is selected from a human Vλ segment and a human Vκ segment. In a specific embodiment, the $V_L$ segment of the first two identical polypeptides is a human Vκ segment and the $V_L$ segment of the second two identical polypeptides is selected from a human Vκ segment and a human Vλ segment. In a specific embodiment, the $V_L$ segment of the first two identical polypeptides is a human Vλ segment and the $V_L$ segment of the second two identical polypeptides is selected from a human Vλ segment and a human Vκ segment. In a specific embodiment, the human $V_L$ segment of the first two identical polypeptides is a human Vκ segment, and the human $V_L$ segment of the second two identical polypeptides is a human Vκ segment.

In one embodiment, the IgG of the mouse comprises a binding protein made in response to an antigen, wherein the binding protein comprises a polypeptide that consists essentially of a variable domain and a $C_H$ region, wherein the variable domain is encoded by a nucleotide sequence that consists essentially of a rearranged $V_L$ segment and a rearranged J segment, and wherein the binding protein specifically binds an epitope of the antigen with a $K_D$ in the micromolar, nanomolar, or picomolar range.

In one aspect, a mouse is provided, wherein all or substantially all of the IgG made by the mouse in response to an antigen comprises a heavy chain that comprises a variable domain, wherein the variable domain is encoded by a rearranged gene derived from gene segments that consist essentially of a V gene segment and a J gene segment. In one embodiment, the rearranged gene comprises 1, 2, 3, 4, 5, 6, 7, 8, 9, or 10 or more N additions.

In one embodiment, the V segment is a V segment of a light chain. In one embodiment, the light chain is selected from a κ light chain and a λ light chain. In a specific embodiment, the light chain is a κ light chain. In a specific embodiment, the V segment is a human V segment. In a specific embodiment, the V segment is a human Vκ segment and the J segment is a human Jκ segment.

In one embodiment, the J segment is a J segment of a light chain. In one embodiment, the light chain is selected from a κ light chain and a λ light chain. In a specific embodiment, the light chain is a κ light chain. In a specific embodiment, the J segment is a human J segment. In another embodiment, the J segment is a J segment of a heavy chain (i.e., a $J_H$). In a specific embodiment, the heavy chain is of mouse origin. In another specific embodiment, the heavy chain is of human origin.

In one embodiment, the variable domain of the heavy chain that is made from no more than a V segment and a J segment is a somatically mutated variable domain.

In one embodiment, the variable domain of the heavy chain that is made from no more than a V segment and a J segment is fused to a mouse $C_H$ region.

In a specific embodiment, all or substantially all of the IgG made by the mouse in response to an antigen comprises a variable domain that is derived from no more than one human V segment and no more than one human J segment, and the variable domain is fused to a mouse IgG constant region, and the IgG further comprises a light chain that comprises a human $V_L$ domain fused with a mouse $C_L$ region. In a specific embodiment, the $V_L$ domain fused with the mouse $C_L$ region is derived from a human Vκ segment and a human Jκ segment. In a specific embodiment, the $V_L$ domain fused with the mouse $C_L$ region is derived from a human Vλ segment and a human Jλ segment.

In one aspect, a mouse is provided that makes an IgG comprising a first CDR3 on a polypeptide comprising a $C_H$ region and a second CDR3 on a polypeptide comprising a $C_L$ region, wherein both the first CDR3 and the second CDR3 are each independently derived from no more than two gene segments, wherein the two gene segments consist essentially of a $V_L$ gene segment and a $J_L$ gene segment. In one embodiment, the CDR3 on the polypeptide comprising the $C_H$ region comprises a sequence that is derived from a CDR3 nucleotide sequence that comprises 1, 2, 3, 4, 5, 6, 7, 8, 9, or 10 or more N additions.

In one embodiment, the $V_L$ segment and the $J_L$ segment are human gene segments. In one embodiment, the $V_L$ segment and the $J_L$ segment are κ gene segments. In one embodiment, the $V_L$ segment and the $J_L$ segment are λ gene segments.

In one aspect, a mouse is provided that makes an IgG comprising a first CDR3 on a first polypeptide comprising a $C_H$ region and a second CDR3 on a second polypeptide comprising a $C_L$ region, wherein both the first CDR3 and the second CDR3 each comprise a sequence of amino acids wherein more than 75% of the amino acids are derived from a V gene segment. In one embodiment, the CDR3 on the polypeptide comprising the $C_H$ region comprises a sequence that is derived from a CDR3 nucleotide sequence that comprises 1, 2, 3, 4, 5, 6, 7, 8, 9, or 10 or more N additions.

In one embodiment, more than 80%, more than 90%, or more than 95% of the amino acids of the first CDR3, and more than 80%, more than 90%, or more than 95% of the amino acids of the second CDR3, are derived from a light chain V segment.

In one embodiment, no more than two amino acids of the first CDR3 are derived from a gene segment other than a light chain V segment. In one embodiment, no more than two amino acids of the second CDR3 are derived from a gene segment other than a light chain V segment. In a specific embodiment, no more than two amino acids of the first CDR3 and no more than two amino acids of the second CDR3 are derived from a gene segment other than a light chain V segment. In one embodiment, no CDR3 of the IgG comprises an amino acid sequence derived from a D gene segment. In one embodiment, the CDR3 of the first polypeptide does not comprise a sequence derived from a D segment.

In one embodiment, the V segment is a human V gene segment. In a specific embodiment, the V segment is a human Vκ gene segment.

In one embodiment, the first and/or the second CDR3 have at least one, two, three, four, five, or six somatic hypermutations. In one embodiment, the first CDR3 is encoded by a nucleic acid sequence that comprises 1, 2, 3, 4, 5, 6, 7, 8, 9, or 10 or more N additions.

In one embodiment, the first CDR3 consists essentially of amino acids derived from a human light chain V gene segment and a human light chain J gene segment, and the second CDR3 consists essentially of amino acids derived from a human light chain V gene segment and a human light chain J gene segment. In one embodiment, the first CDR3 is derived from a nucleic acid sequence that comprises 1, 2, 3, 4, 5, 6, 7, 8, 9, or 10 or more N additions. In one embodiment, the first CDR3 is derived from no more than two gene segments, wherein the no more than two gene segments are a human Vκ gene segment and a human Jκ gene segment; and the second CDR3 is derived from no more than two gene segments, wherein the no more than two gene segments are a human Vκ gene segment and a J gene segment selected from a human Jκ segment, a human Jλ segment, and a human $J_H$ segment. In one embodiment, the first CDR3 is derived from no more than two gene segments, wherein the no more than two gene segments are a human Vλ segment and a J segment selected from a human Jκ segment, a human Jλ segment, and a human $J_H$ segment.

In one aspect, a mouse is provided that makes an IgG that does not contain an amino acid sequence derived from a $D_H$ gene segment, wherein the IgG comprises a first polypeptide having a first $V_L$ domain fused with a mouse $C_L$ region and a second polypeptide having a second $V_L$ domain fused with a mouse $C_H$ region, wherein the first $V_L$ domain and the second $V_L$ domain are not identical. In one embodiment, the first and second $V_L$ domains are derived from different V segments. In another embodiment, the first and second $V_L$ domains are derived from different J segments. In one embodiment, the first and second $V_L$ domains are derived from identical V and J segments, wherein the second $V_L$ domain comprises a higher number of somatic hypermutations as compared to the first $V_L$ domain.

In one embodiment, the first and the second $V_L$ domains are independently selected from human and mouse $V_L$ domains. In one embodiment, the first and second $V_L$ domains are independently selected from Vκ and Vλ domains. In a specific embodiment, the first $V_L$ domain is selected from a Vκ domain and a Vλ domain, and the second $V_L$ domain is a Vκ domain. In another specific embodiment, the Vκ domain is a human Vκ domain.

In one aspect, a mouse is provided, wherein all or substantially all of the IgG made by the mouse consists essentially of a light chain having a first human $V_L$ domain fused with a mouse $C_L$ domain, and a heavy chain having a second human $V_L$ domain fused with a mouse $C_H$ domain.

In one embodiment, the human $V_L$ domain fused with the mouse $C_H$ domain is a human Vκ domain.

In one embodiment, the first and the second human $V_L$ domains are not identical.

In one aspect, a mouse is provided, wherein at least 10%, 20%, 30%, 40%, 50%, 60%, 70%, 80%, 90%, 95%, or about 100% of the immunoglobulin G made by the mouse consists essentially of a dimer of (a) a first polypeptide that consists essentially of an immunoglobulin $V_L$ domain and an immunoglobulin $C_L$ region; and, (b) a second polypeptide of no more than 535 amino acids in length, wherein the second polypeptide consists essentially of a $C_H$ region and a V domain that lacks a sequence derived from a $D_H$ gene segment.

In one embodiment, the second polypeptide is about 435-535 amino acids in length. In a specific embodiment, the second polypeptide is about 435-530 amino acids in length. In a specific embodiment, the second polypeptide is about 435-525 amino acids in length. In a specific embodiment, the second polypeptide is about 435-520 amino acids in length. In a specific embodiment, the second polypeptide is about 435-515 amino acids in length.

In one embodiment, in about 90% or more of the IgG made by the mouse the second polypeptide is no more than about 535 amino acids in length.

In one embodiment, in about 50% or more of the IgG made by the mouse the second polypeptide is no more than about 535 amino acids in length. In one embodiment, in about 50% or more of the immunoglobulin G made by the mouse the second polypeptide is no more than about 530, 525, 520, 515, 510, 505, 500, 495, 490, 485, 480, 475, 470, 465, 460, 455, or 450 amino acids in length. In one embodiment, about 60%, 70%, 80%, 90%, or 95% or more of the IgG made by the mouse is of the recited length. In a specific embodiment, all or substantially all of the IgG made by the mouse is of the recited length.

In one embodiment, the V domain of the second polypeptide is a $V_L$ domain. In a specific embodiment, the V domain of the second polypeptide is selected from a Vκ and a Vλ domain. In a specific embodiment, the V domain of the second polypeptide is a human Vκ or Vλ domain.

In one aspect, a mouse is provided that expresses from a nucleotide sequence in its germline a polypeptide that comprises a light chain variable sequence (e.g., a V and/or J sequence), a $D_H$ sequence, and a heavy chain constant region.

In one embodiment, the mouse expresses the polypeptide from an endogenous mouse heavy chain locus that comprises a replacement of all or substantially all functional endogenous mouse heavy chain variable locus gene segments with a plurality of human gene segments at the endogenous mouse heavy chain locus.

In one embodiment, the polypeptide comprises a $V_L$ sequence derived from a Vλ or a Vκ gene segment, the polypeptide comprises a CDR3 derived from a $D_H$ gene segment, and the polypeptide comprises a sequence derived from a $J_H$ or Jλ or Jκ gene segment.

In one embodiment, the mouse comprises an endogenous mouse heavy chain immunoglobulin locus comprising a replacement of all functional $V_H$ gene segments with one or more human light chain Vλ gene segments wherein the one or more human Vλ segments each have juxtaposed on the downstream side a 23-mer spaced recombination signal sequence (RSS), wherein the Vλ segments are operably linked to a human or mouse $D_H$ segment that has juxtaposed upstream and downstream a 12-mer spaced RSS; the $D_H$ gene segment is operably linked with a J segment juxtaposed upstream with a 23-mer spaced RSS that is suitable for recombining with the 12-mer spaced RSS juxtaposing the $D_H$ gene segment; wherein the V, $D_H$, and J segments are operably linked to a nucleic acid sequence encoding a heavy chain constant region.

In one embodiment, the mouse comprises an endogenous mouse heavy chain immunoglobulin locus comprising a replacement of all functional $V_H$ gene segments with one or more human Vκ gene segments each juxtaposed on the downstream side with a 12-mer spaced recombination signal sequence (RSS), wherein the V segments are operably linked to a human or mouse $D_H$ segment that is juxtaposed both upstream and downstream with a 23-mer spaced RSS; the $D_H$ segment is operably linked with a J segment juxtaposed on the upstream side with a 12-mer spaced RSS that is suitable for recombining with the 23-mer spaced RSS juxtaposing the $D_H$ segment; wherein the V, $D_H$, and gene segments are operably linked to a nucleic acid sequence encoding a heavy chain constant region.

In one embodiment, the heavy chain constant region is an endogenous mouse heavy chain constant region. In one embodiment, the nucleic acid sequence encodes a sequence selected from a $C_H1$, a hinge, a $C_H2$, a $C_H3$, and a combination thereof. In one embodiment, one or more of the $C_H1$, hinge, $C_H2$, and $C_H3$ are human.

In one embodiment, the mouse comprises an endogenous mouse heavy chain immunoglobulin locus comprising a replacement of all functional $V_H$ gene segments with a plurality of human Vλ or Vκ gene segments each juxtaposed downstream with 23-mer spaced RSS, a plurality of human $D_H$ segments juxtaposed both upstream and downstream by a 12-mer spaced RSS, a plurality of human J segments ($J_H$ or Jλ or Jκ) juxtaposed both upstream and downstream with a 23-mer spaced RSS, wherein the locus comprises an endogenous mouse constant region sequence selected from $C_H1$, hinge, $C_H2$, $C_H3$, and a combination thereof. In a specific embodiment, the mouse comprises all or substantially all functional human Vλ or Vκ segments, all or substantially all functional human $D_H$ segments, and all or substantially all $J_H$ or Jλ or Jκ segments.

In one embodiment, the mouse expresses an antigen-binding protein comprising (a) a polypeptide that comprises a human light chain sequence linked to a heavy chain constant sequence comprising a mouse sequence; and (b) a polypeptide that comprises a human light chain variable region linked to a human or mouse light chain constant sequence. In a specific embodiment, the light chain sequence is a human light chain sequence, and upon exposure to a protease that is capable of cleaving an antibody into an Fc and a Fab, a fully human Fab is formed that comprises at least four light chain CDRs, wherein the at least four light chain CDRs are selected from λ sequences, κ sequences, and a combination thereof. In one embodiment, the Fab comprises at least five light chain CDRs. In one embodiment, the Fab comprises six light chain CDRs. In one embodiment, at least one CDR of the Fab comprises a sequence derived from a Vλ segment or a Vκ segment, and the at least one CDR further comprises a sequence derived from a D segment. In one embodiment, the at least one CDR is a CDR3 and the CDR is derived from a human Vκ segment, a human D segment, and a human Jκ segment.

In one embodiment, the polypeptide of comprises a variable region derived from a human Vλ or Vκ gene segment, a human $D_H$ gene segment, and a human $J_H$ or Jλ or Jκ gene segment. In a specific embodiment, the heavy chain constant sequence is derived from a human $C_H1$ and a mouse $C_H2$ and a mouse $C_H3$ sequence.

In one aspect, a mouse is provided that comprises in its germline an unrearranged human Vκ or Vλ gene segment operably linked to a human J gene segment and a heavy chain constant region sequence, wherein the mouse expresses a $V_L$ binding protein that comprises a human Vκ domain fused with a heavy chain constant region, and wherein the mice exhibit a population of splenic B cells that express $V_L$ binding proteins in CD19$^+$ B cells, including transitional B cells (CD19$^+$IgM$^{hi}$IgD$^{int}$), and mature B cells (CD19$^+$IgM$^{int}$IgD$^{hi}$).

In one aspect, a mouse is provided that comprises in its germline an unrearranged human Vκ or Vλ gene segment operably linked to a human J gene segment and a heavy chain constant region sequence, wherein the mouse expresses on a B cell an immunoglobulin that comprises a light chain variable domain fused with a heavy chain constant region, wherein the lymphocyte population in bone marrow of the mice exhibit a pro/pre B cell population that is about the same in number as in a pro/pre B cell population of a wild-type mouse (lymphocytes in bone marrow).

In one embodiment, the mice comprise at least 6 unrearranged hVκ gene segments and one or more unrearranged hJκ gene segments, and the mice comprise a lymphocyte-gated and IgM$^+$ spleen cell population expressing a $V_L$ binding protein, wherein the population is at least 75% as large as a lymphocyte-gated and IgM$^+$ spleen cell population of a wild-type mouse.

In one embodiment, the mice exhibit a mature B cell-gated (CD19$^+$) splenocyte population of IgD$^+$ cells and IgM$^+$ cells that total about 90%; in one embodiment, the mature B cell-gated (CD19$^+$) splenocyte population of IgD$^+$ cells and IgM$^+$ cells of the modified mouse is about the same (e.g., within 10%, or within 5%) as the total of IgD$^+$ cells and IgM$^+$ cells of a wild-type mouse that are mature B cell-gated (CD19$^+$) splenocytes.

In one aspect, a mouse is provided that expresses an immunoglobulin protein from a modified endogenous heavy chain locus in its germline, wherein the modified endogenous heavy chain locus lacks a functional mouse heavy chain V gene segment and the locus comprises unrearranged light chain V gene segments and unrearranged J gene segments, wherein the unrearranged light chain V gene segments and unrearranged J gene segments are operably linked with a heavy chain constant region sequence; wherein the immunoglobulin protein consists essentially of a first polypeptide and a second polypeptide, wherein the first polypeptide comprises an immunoglobulin light chain sequence and an immunoglobulin heavy chain constant sequence, and the second polypeptide comprises an immunoglobulin light chain variable domain and a light chain constant region.

In one aspect, a mouse is provided that expresses an immunoglobulin protein, wherein the immunoglobulin protein lacks a heavy chain immunoglobulin variable domain, and the immunoglobulin protein comprises a first variable domain derived from a light chain gene, and a second variable domain derived from a light chain gene, wherein the first variable domain and the second variable domain are cognate with respect to one another, wherein the first and the second light chain variable domains are not identical, and wherein the first and the second light chain variable domains associate and when associated specifically bind an antigen of interest.

In one aspect, a mouse is provided that makes from unrearranged gene segments in its germline an immunoglobulin protein comprising variable regions that are wholly derived from gene segments that consist essentially of unrearranged human gene segments, wherein the immunoglobulin protein comprises an immunoglobulin light chain constant sequence and an immunoglobulin heavy chain constant sequence selected from the group consisting of a $C_H1$, a hinge, a $C_H2$, a $C_H3$, and a combination thereof.

In one aspect, a mouse is provided that makes from unrearranged gene segments in its germline an immunoglobulin protein comprising variable regions, wherein all CDR3s of all variable regions are generated entirely from light chain V and J gene segments, and optionally one or more somatic hypermutations, e.g., one or more N additions.

In one aspect, a mouse is provided that makes a somatically mutated immunoglobulin protein derived from unrearranged human immunoglobulin light chain variable region gene segments in the germline of the mouse, wherein the immunoglobulin protein lacks a CDR that comprises a sequence derived from a D gene segment, wherein the immunoglobulin protein comprises a first CDR3 on a light chain variable domain fused with a light chain constant region, comprises a second CDR3 on a light chain variable domain fused with a heavy chain constant region, and wherein the second CDR3 is derived from a rearranged light chain variable region sequence that comprises 1, 2, 3, 4, 5, 6, 7, 8, 9, or 10 or more N additions.

In one aspect, a mouse as described herein is provided, wherein the mouse comprises a functionally silenced light chain locus selected from a λ locus, a κ locus, and a combination thereof. In one embodiment, the mouse comprises a deletion of a λ and/or a κ locus, in whole or in part, such that the λ and/or κ locus is nonfunctional.

In one aspect, a mouse embryo is provided, comprising a cell that comprises a modified immunoglobulin locus as described herein. In one embodiment, the mouse is a chimera and at least 10%, 20%, 30%, 40%, 50%, 60%, 70%, 80%, 90%, or 95% of the cells of the embryo comprise a modified immunoglobulin locus as described herein. In one embodiment, at least 96%. 97%, 98%, 99%, or 99.8% of the cells of the embryo comprise a modified immunoglobulin locus as described herein. In one embodiment, the embryo comprises a host cell and a cell derived from a donor ES cell, wherein the cell derived from the donor ES cell comprises a modified immunoglobulin locus as described herein. In one embodiment, the embryo is a 2-, 4-, 8, 16-, 32, or 64-cell stage host embryo, or a blastocyst, and further comprises a donor ES cell comprising a modified immunoglobulin locus as described herein.

In one aspect, a mouse or a cell made using a nucleic acid construct as described herein is provided.

In one aspect, a mouse made using a cell as described herein is provided. In one embodiment, the cell is a mouse ES cell.

In one aspect, use of a mouse as described herein to make a nucleic acid sequence encoding a first human light chain immunoglobulin variable sequence ($V_L1$) that is cognate with a second human light chain immunoglobulin variable sequence ($V_L2$), wherein the $V_L1$ fused with a human immunoglobulin light chain constant region (polypeptide 1) expresses with $V_L2$ fused with a human immunoglobulin heavy chain constant region (polypeptide 2), as a dimer of polypeptide1/polypeptide 2, to form a $V_L1$-$V_L2$ antibody.

In one aspect, use of a mouse as described herein to make a nucleic acid sequence encoding a human immunoglobulin light chain variable sequence that is fused with a human immunoglobulin heavy chain sequence, wherein the nucleic acid sequence encodes a human $V_L$-$C_H$ polypeptide, wherein the human $V_L$-$C_H$ polypeptide expresses as a dimer, and wherein the dimer expresses in the absence of an immunoglobulin light chain (e.g., in the absence of a human λ or human κ light chain). In one embodiment, the $V_L$-$C_H$ dimer specifically binds an antigen of interest in the absence of a λlight chain and in the absence of a κlight chain.

In one aspect, use of a mouse as described herein to make a nucleic acid sequence encoding all or a portion of an immunoglobulin variable domain. In one embodiment, the immunoglobulin variable domain is a human Vλ or human Vκ domain.

In one aspect, use of a mouse as described herein to make a fully human Fab (comprising a first human $V_L$ fused with a human light chain constant region, and a second human $V_L$ fused with a human heavy chain constant region sequence) or a fully human F(ab)$_2$ is provided.

In one aspect, use of a mouse as described herein to make an immortalized cell line is provided. In one embodiment, the immortalized cell line comprises a nucleic acid sequence encoding a human Vλ or Vκ domain operably linked to a nucleic acid sequence that comprises a mouse constant region nucleic acid sequence.

In one aspect, use of a mouse as described herein to make a hybridoma or quadroma is provided.

In one aspect, a cell is provided, comprising a modified immunoglobulin locus as described herein. In one embodiment, the cell is selected from a totipotent cell, a pluripotent cell, an induced pluripotent stem cell (iPS), and an ES cell. In a specific embodiment, the cell is a mouse cell, e.g., a mouse ES cell. In one embodiment, the cell is homozygous for the modified immunoglobulin locus.

In one aspect, a cell is provided, comprising a nucleic acid sequence encoding a first polypeptide that comprises a first somatically mutated human Vκ or Vλ sequence fused to a human heavy chain constant region sequence.

In one embodiment, the cell further comprises a second polypeptide chain that comprises a second somatically mutated human Vκ or Vλ sequence fused to a human light chain constant region sequence.

In one embodiment, the human Vκ or Vλ sequence of the first polypeptide is cognate with the human Vκ or Vλ sequence of the second polypeptide.

In one embodiment, the Vκ or Vλ of the first polypeptide and the human Vκ or Vλ of the second polypeptide when associated specifically bind an antigen of interest. In a specific embodiment, the first polypeptide comprises a variable domain consisting essentially of a human Vκ, and the second polypeptide comprises a variable domain consisting of a human Vκ that is cognate with the human Vκ of the first polypeptide, and the human constant region sequence is an IgG sequence.

In one embodiment, the cell is selected from a CHO cell, a COS cell, a 293 cell, a HeLa cell, and a human retinal cell expressing a viral nucleic acid sequence (e.g., a PERC.6™ cell.

In one aspect, a somatic mouse cell is provided, comprising a chromosome that comprises a genetic modification as described herein.

In one aspect, a mouse germ cell is provided, comprising a nucleic acid sequence that comprises a genetic modification as described herein.

In one aspect, a pluripotent, induced pluripotent, or totipotent cell derived from a mouse as described herein is provided. In a specific embodiment, the cell is a mouse embryonic stem (ES) cell.

In one aspect, use of a cell as described herein for the manufacture of a mouse, a cell, or a therapeutic protein (e.g., an antibody or other antigen-binding protein) is provided.

In one aspect, a nucleic acid construct is provided that comprises a human $D_H$ gene segment juxtaposed upstream and downstream with a 23-mer spaced RSS. In a specific embodiment, the nucleic acid construct comprises a homology arm that is homologous to a human genomic sequence comprising human Vκ gene segments. In one embodiment, the targeting construct comprises all or substantially all human $D_H$ gene segments each juxtaposed upstream and downstream with a 23-mer spaced RSS.

In one aspect, a nucleic acid construct is provided that comprises a human Jκ gene segment juxtaposed upstream with a 12-mer spaced RSS. In a specific embodiment, the nucleic acid construct comprises a first homology arm that contains homology to a human genomic $D_H$ gene sequence that is juxtaposed upstream and downstream with a 23-mer spaced RSS. In one embodiment, the nucleic acid construct comprises a second homology arm that contains homology to a human genomic J gene sequence or that contains homology to a mouse heavy chain constant region sequence or that contains homology to a J-C intergenic sequence upstream of a mouse constant region heavy chain sequence.

In one aspect, a nucleic acid construct is provided that comprises a human Vλ segment juxtaposed downstream with a 23-mer spaced RSS, a human $D_H$ segment juxtaposed upstream and downstream with a 12-mer spaced RSS, and a human J segment selected from a Jκ segment juxtaposed upstream with a 23-mer spaced RSS, a human Jλ segment juxtaposed upstream with a 23-mer spaced RSS, and a human $J_H$ segment juxtaposed upstream with a 23-mer spaced RSS. In one embodiment, the construct comprises a homology arm that contains homology to a mouse constant region sequence, a J-C intergenic mouse sequence, and/or a human Vλ sequence.

In one embodiment, the nucleic acid construct comprises a human λ light chain variable region sequence that comprises a fragment of cluster A of the human λ light chain locus. In a specific embodiment, the fragment of cluster A of the human λ light chain locus extends from hVλ3-27 through hVλ3-1.

In one embodiment, the nucleic acid construct comprises a human λ light chain variable region sequence that comprises a fragment of cluster B of the human λ light chain locus. In a specific embodiment, the fragment of cluster B of the human λ light chain locus extends from hVλ5-52 through hVλ1-40.

In one embodiment, nucleic acid construct comprises a human λ light chain variable region sequence that comprises a genomic fragment of cluster A and a genomic fragment of cluster B. In a one embodiment, the human λ light chain variable region sequence comprises at least one gene segment of cluster A and at least one gene segment of cluster B.

In one embodiment, the human λ light chain variable region sequence comprises at least one gene segment of cluster B and at least one gene segment of cluster C.

In one aspect, a nucleic acid construct is provided, comprising a human $D_H$ segment juxtaposed upstream and downstream with a 23-mer spaced RSS normally found in nature flanking either a Jκ, a $J_H$, a Vλ, or a $V_H$ segment. In one embodiment, the nucleic acid construct comprises a first homology arm homologous to a human V-J intergenic region or homologous to a human genomic sequence comprising a human V gene segment. In one embodiment, the nucleic acid construct comprises a second homology arm homologous to a human or mouse heavy chain constant region sequence. In a specific embodiment, the human or mouse heavy chain constant region sequence is selected from a $C_H1$, hinge, $C_H2$, $C_H3$, and a combination thereof. In one embodiment, the nucleic acid construct comprises a human J gene segment flanked upstream with a 12-mer RSS. In one embodiment, the nucleic acid construct comprises a second homology arm that contains homology to a J gene segment flanked upstream with a 12-mer RSS. In one embodiment, the J gene segment is selected from a human Jκ, a human Jλ, and a human $J_H$.

In one aspect, a nucleic acid construct is provided that comprises a human $D_H$ segment juxtaposed upstream and downstream with a 23-mer spaced RSS, and a site-specific recombinase recognition sequence, e.g., a sequence recognized by a site-specific recombinase such as a Cre, a Flp, or a Dre protein.

In one aspect, a nucleic acid construct is provided that comprises a human Vλ or a human Vκ segment, a $D_H$ segment juxtaposed upstream and downstream with a 12-mer or a 23-mer spaced RSS, and a human J segment with a 12-mer or a 23-mer spaced RSS, wherein the 12-mer or 23-mer spaced RSS is positioned immediately 5' to the human J segment (i.e., with respect to the direction of transcription). In one embodiment, the construct comprises a human Vλ juxtaposed with a 3' 23-mer spaced RSS, a human $D_H$ segment juxtaposed upstream and downstream with a 12-mer spaced RSS, and a human Jκ segment juxtaposed with a 5' 23-mer spaced RSS. In one embodiment, the construct comprises a human Vκ juxtaposed with a 3' 12-mer spaced RSS, a human $D_H$ segment juxtaposed upstream and downstream with a 23-mer spaced RSS, and a human Jλ segment juxtaposed with a 5' 12-mer spaced RSS.

In one aspect, a targeting vector is provided, comprising (a) a first targeting arm and a second targeting arm, wherein the first and second targeting arms are independently selected from human and mouse targeting arms, wherein the targeting arms direct the vector to an endogenous or modified immunoglobulin V region gene locus; and, (b) a contiguous sequence of human $V_L$ gene segments or a contiguous sequence of human $V_L$ gene segments and at least one human Jκ gene segment, wherein the contiguous sequence is selected from the group consisting of (i) hVκ4-1 through hVκ1-6 and Jκ1, (ii) hVκ4-1 through hVκ1-6 and Jκ1 through Jκ2, (iii) hVκ4-1 through hVκ1-6 and Jκ1 through Jκ3, (iv) hVκ4-1 through hVκ1-6 and Jκ1 through Jκ4, (v) hVκ4-1 through hVκ1-6 and Jκ1 through Jκ5, (vi) hVκ3-7 through hVκ1-16, (vii) hVκ1-17 through hVκ2-30, (viii) hVκ3-31 through hVκ2-40, and (ix) a combination thereof.

In one embodiment, the targeting arms that direct the vector to an endogenous or modified immunoglobulin locus are identical or substantially identical to a sequence at the endogenous or modified immunoglobulin locus.

In one aspect, use of a nucleic acid construct as described herein for the manufacture of a mouse, a cell, or a therapeutic protein (e.g., an antibody or other antigen-binding protein) is provided.

In one aspect, use of a nucleic acid sequence from a mouse as described herein to make a cell line for the manufacture of a human therapeutic is provided. In one embodiment, the human therapeutic is a binding protein comprising a human light chain variable sequence (e.g., derived from a human Vλ or human Vκ segment) fused with a human heavy chain constant sequence. In one embodiment, the human therapeutic comprises a first polypeptide that is a human λ or κ immunoglobulin light chain, and a second polypeptide that comprises a human Vλ or human Vκ variable sequence fused with a human heavy chain constant sequence.

In one aspect, an expression system is provided, comprising a mammalian cell transfected with a DNA construct that encodes a polypeptide that comprises a somatically mutated human $V_L$ domain fused with a human $C_H$ domain.

In one embodiment, the expression system further comprises a nucleotide sequence that encodes an immunoglobulin $V_L$ domain fused with a human $C_L$ domain, wherein the $V_L$ domain fused with the human $C_L$ domain is a cognate light chain with the $V_L$ domain fused with the human $C_H$ domain.

In one embodiment, the mammalian cell is selected from a CHO cell, a COS cell, a Vero cell, a 293 cell, and a retinal cell that expresses a viral gene (e.g., a PER.C6™ cell).

In one aspect, a method for making a binding protein is provided, comprising obtaining a nucleotide sequence encoding a $V_L$ domain from a gene encoding a $V_L$ region fused to a $C_H$ region from a cell of a mouse as described herein, and cloning the nucleotide sequence encoding the $V_L$ region sequence in frame with a gene encoding a human $C_H$ region to form a human binding protein sequence, expressing the human binding protein sequence in a suitable cell.

In one embodiment, the mouse has been immunized with an antigen of interest, and the $V_L$ region fused to the $C_H$ region specifically binds (e.g., with a $K_D$ in the micromolar, nanomolar, or picomolar range) an epitope of the antigen of interest. In one embodiment, nucleotide sequence encoding the $V_L$ region fused to the $C_H$ region is somatically mutated in the mouse.

In one embodiment, the suitable cell is selected from a B cell, a hybridoma, a quadroma, a CHO cell, a COS cell, a 293 cell, a HeLa cell, and a human retinal cell expressing a viral nucleic acid sequence (e.g., a PERC.6™ cell).

In one embodiment, the $C_H$ region comprises a human IgG isotype. In a specific embodiment, the human IgG is selected from an IgG1, IgG2, and IgG4. In another specific embodiment, the human IgG is IgG1. In another specific embodiment, the human IgG is IgG4. In another specific embodiment, the human IgG4 is a modified IgG4. In one embodiment, the modified IgG4 comprises a substitution in the hinge region. In a specific embodiment, the modified IgG4 comprises a substitution at amino acid residue 228 relative to a wild-type human IgG4, numbered according to the EU numbering index of Kabat. In a specific embodiment, the substitution at amino acid residue 228 is a S228P substitution, numbered according to the EU numbering index of Kabat.

In one embodiment, the cell further comprises a nucleotide sequence encoding a $V_L$ domain from a light chain that is cognate to the $V_L$ domain fused to the $C_H$ region, and the method further comprises expressing the nucleotide sequence encoding the cognate $V_L$ domain fused to a human Cκ or Cλ domain.

In one aspect, a method for making a genetically modified mouse is provided, comprising replacing at an endogenous mouse heavy chain locus one or more immunoglobulin heavy chain gene segments of a mouse with one or more human immunoglobulin light chain gene segments. In one embodiment, the replacement is of all or substantially all functional mouse immunoglobulin heavy chain segments (i.e., $V_H$, $D_H$, and $J_H$ segments) with one or more functional human light chain segments (i.e., $V_L$ and $J_L$ segments). In one embodiment, the replacement is of all or substantially all functional mouse heavy chain $V_H$, $D_H$, and $J_H$ segments with all or substantially all human Vλ or Vκ segments and at least one Jλ or Jκ segment. In a specific embodiment, the replacement includes all or substantially all functional human Jλ or Jκ segments.

In one aspect, a method is provided for making a mouse that expresses a polypeptide that comprises a sequence derived from a human immunoglobulin Vλ or Vκ and/or Jλ or Jκ segment fused with a mouse heavy chain constant region, comprising replacing endogenous mouse heavy chain immunoglobulin variable segments ($V_H$, $D_H$, and $J_H$) with at least one human Vλ or Vκ segment and at least one human Jλ or Jκ segment, wherein the replacement is in a pluripotent, induced pluripotent, or totipotent mouse cell to form a genetically modified mouse progenitor cell; the genetically modified mouse progenitor cell is introduced into a mouse host; and, the mouse host comprising the genetically modified progenitor cell is gestated to form a mouse comprising a genome derived from the genetically modified mouse progenitor cell. In one embodiment, the host is an embryo. In a specific embodiment, the host is selected from a mouse pre-morula (e.g., 8- or 4-cell stage), a tetraploid embryo, an aggregate of embryonic cells, or a blastocyst.

In one aspect, a method is provided for making a genetically modified mouse as described herein, comprising introducing by nuclear transfer a nucleic acid containing a modification as described herein into a cell, and maintaining the cell under suitable conditions (e.g., including culturing the cell and gestating an embryo comprising the cell in a surrogate mother) to develop into a mouse as described herein.

In one aspect, a method for making a modified mouse is provided, comprising modifying as described herein a mouse ES cell or pluripotent or totipotent or induced pluripotent mouse cell to include one or more unrearranged immunoglobulin light chain variable gene segments operably linked to an immunoglobulin heavy chain constant sequence, culturing the ES cell, introducing the cultured ES cell into a host embryo to form a chimeric embryo, and introducing the chimeric embryo into a suitable host mouse to develop into a modified mouse. In one embodiment, the one or more unrearranged immunoglobulin light chain variable region gene segments are human λ or human κ gene segments. In one embodiment, the one or more unrearranged immunoglobulin light chain variable region gene segments comprise human Vλ or human Vκ segments and one or more Jλ, Jκ, or $J_H$ segments. In one embodiment, the heavy chain constant gene sequence is a human sequence selected from $C_H1$, hinge, $C_H2$, $C_H3$, and a combination thereof. In one embodiment, the one or more unrearranged immunoglobulin light chain variable gene segments replace all or substantially all functional endogenous mouse heavy chain variable region gene segments at the endogenous mouse heavy chain locus, and the heavy chain constant sequence is a mouse sequence comprising a $C_H1$, a hinge, a $C_H2$, and a $C_H3$.

In one aspect, an immunoglobulin variable region (VR) (e.g., comprising a human $V_L$ sequence fused with a human $J_L$, or $J_H$, or $D_H$ and $J_H$, or $D_H$ and $J_L$) made in a mouse as described herein is provided. In a specific embodiment, the immunoglobulin VR is derived from a germline human gene segment selected from a Vκ segment and a Vλ segment, wherein the VR is encoded by a rearranged sequence from the mouse wherein the rearranged sequence is somatically hypermutated. In one embodiment, the rearranged sequence comprises 1 to 5 somatic hypermutations. In one embodiment, the rearranged sequence comprises at least 6, 7, 8, 9, or 10 somatic hypermutations. In one embodiment, the rearranged sequence comprises more than 10 somatic hypermutations. In one embodiment, the rearranged sequence is fused with one or more human or mouse heavy chain constant region sequences (e.g., selected from a human or mouse $C_H1$, hinge, $C_H2$, $C_H3$, and a combination thereof).

In one aspect, an immunoglobulin variable domain amino acid sequence of a binding protein made in a mouse as described herein is provided. In one embodiment, the VR is fused with one or more human or mouse heavy chain constant region sequences (e.g., selected from a human or mouse $C_H1$, hinge, $C_H2$, $C_H3$, and a combination thereof).

In one aspect, a light chain variable domain encoded by a nucleic acid sequence derived from a mouse as described herein is provided.

In one aspect, an antibody or antigen-binding fragment thereof (e.g., Fab, $F(ab)_2$, scFv) made in a mouse as described herein, or derived from a sequence made in a mouse as described herein, is provided.

BRIEF DESCRIPTION OF THE FIGURES

FIG. 9 shows a nucleotide sequence alignment of the Vκ-Jκ-mIgG junction of twelve independent RT-PCR clones amplified from splenocyte RNA of naïve mice homozygous for thirty hVκ and five Jκ gene segments at the mouse heavy chain locus and a replacement of the endogenous Vκ and Jκ gene segments with human Vκ and Jκ gene segment. Lower case bases indicate non-germline bases resulting from either mutation and/or N addition during recombination. Artificial spaces (periods) are included to properly align the Framework 4 region and show alignment of the mouse heavy chain IgG nucleotide sequence for IgG1, IgG2a/c, and IgG3 primed clones.

DETAILED DESCRIPTION

Figure 1A:
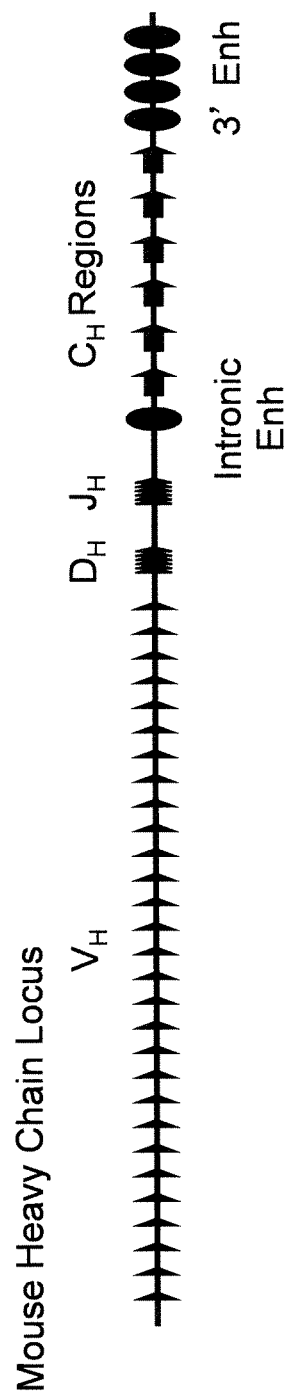
FIG. 1A illustrates a schematic (not to scale) of the mouse heavy chain locus. The mouse heavy chain locus is about 3 Mb in length and contains approximately 200 heavy chain variable ($V_H$) gene segments, 13 heavy chain diversity ($D_H$) gene segments and 4 heavy chain joining ($J_H$) gene segments as well as enhancers (Enh) and heavy chain constant ($C_H$) regions.

The phrase "bispecific binding protein" includes a binding protein capable of selectively binding two or more epitopes. Bispecific binding proteins comprise two different polypeptides that comprise a first light chain variable domain ($V_L1$) fused with a first $C_H$ region and a second light chain variable domain ($V_L2$) fused with a second $C_H$ region. In general, the first and the second $C_H$ regions are identical, or they differ by one or more amino acid substitutions (e.g., as described herein). $V_L1$ and $V_L2$ specifically binding different epitopes-either on two different molecules (e.g., antigens) or on the same molecule (e.g., on the same antigen). If a bispecific binding protein selectively binds two different epitopes (a first epitope and a second epitope), the affinity of $V_L1$ for the first epitope will generally be at least one to two or three or four orders of magnitude lower than the affinity of $V_L1$ for the second epitope, and vice versa with respect to $V_L2$. The epitopes recognized by the bispecific binding protein can be on the same or a different target (e.g., on the same or a different antigen). Bispecific binding proteins can be made, for example, by combining a $V_L1$ and a $V_L2$ that recognize different epitopes of the same antigen. For example, nucleic acid sequences encoding $V_L$ sequences that recognize different epitopes of the same antigen can be fused to nucleic acid sequences encoding different $C_H$ regions, and such sequences can be expressed in a cell that expresses an immunoglobulin light chain, or can be expressed in a cell that does not express an immunoglobulin light chain. A typical bispecific binding protein has two heavy chains each having three light chain CDRs, followed by (N-terminal to C-terminal) a $C_H1$ domain, a hinge, a $C_H2$ domain, and a $C_H3$ domain, and an immunoglobulin light chain that either does not confer antigen-binding specificity but that can associate with each heavy chain, or that can associate with each heavy chain and that can bind one or more of the epitopes bound by $V_L1$ and/or $V_L2$, or that can associate with each heavy chain and enable binding or assist in binding of one or both of the heavy chains to one or both epitopes.

Therefore, two general types of bispecific binding proteins are (1) $V_L1$-$C_H$(dimer), and (2) $V_L1$-$C_H$:light chain+ $V_L2$-$C_H$:light chain, wherein the light chain is the same or different. In either case, the $C_H$ (i.e., the heavy chain constant region) can be differentially modified (e.g., to differentially bind protein A, to increase serum half-life, etc.) as described herein, or can be the same.

The term "cell," when used in connection with expressing a sequence, includes any cell that is suitable for expressing a recombinant nucleic acid sequence. Cells include those of prokaryotes and eukaryotes (single-cell or multiple-cell), bacterial cells (e.g., strains of E. coli, Bacillus spp., Streptomyces spp., etc.), mycobacteria cells, fungal cells, yeast cells (e.g., S. cerevisiae, S. pombe, P. pastoris, P. methanolica, etc.), plant cells, insect cells (e.g., SF-9, SF-21, baculovirus-infected insect cells, Trichoplusia ni, etc.), non-human animal cells, human cells, B cells, or cell fusions such as, for example, hybridomas or quadromas. In some embodiments, the cell is a human, monkey, ape, hamster, rat, or mouse cell. In some embodiments, the cell is eukaryotic and is selected from the following cells: CHO (e.g., CHO K1, DXB-11 CHO, Veggie-CHO), COS (e.g., COS-7), retinal cell, Vero, CV1, kidney (e.g., HEK293, 293 EBNA, MSR 293, MDCK, HaK, BHK), HeLa, HepG2, WI38, MRC 5, Colo205, HB 8065, HL-60, (e.g., BHK21), Jurkat, Daudi, A431 (epidermal), CV-1, U937, 3T3, L cell, C127 cell, SP2/0, NS-0, MMT 060562, Sertoli cell, BRL 3A cell, HT1080 cell, myeloma cell, tumor cell, and a cell line derived from an aforementioned cell. In some embodiments, the cell comprises one or more viral genes, e.g. a retinal cell that expresses a viral gene (e.g., a PER.C6™ cell).

The term "cognate," when used in the sense of "cognate with," e.g., a first $V_L$ domain that is "cognate with" a second $V_L$ domain, is intended to include reference to the relation between two $V_L$ domains from a same binding protein made by a mouse in accordance with the invention. For example, a mouse that is genetically modified in accordance with an embodiment of the invention, e.g., a mouse having a heavy chain locus in which $V_H$, $D_H$, and $J_H$ regions are replaced with $V_L$ and $J_L$ regions, makes antibody-like binding proteins that have two identical polypeptide chains made of the same mouse $C_H$ region (e.g., an IgG isotype) fused with a first human $V_L$ domain, and two identical polypeptide chains made of the same mouse $C_L$ region fused with a second human $V_L$ domain. During clonal selection in the mouse, the first and the second human $V_L$ domains were selected by the clonal selection process to appear together in the context of a single antibody-like binding protein. Thus, first and second $V_L$ domains that appear together, as the result of the clonal selection process, in a single antibody-like molecule are referred to as being "cognate." In contrast, a $V_L$ domain that appears in a first antibody-like molecule and a $V_L$ domain that appears in a second antibody-like molecule are not cognate, unless the first and the second antibody-like molecules have identical heavy chains (i.e., unless the $V_L$ domain fused to the first human heavy chain region and the $V_L$ domain fused to the second human heavy chain region are identical).

The phrase "complementarity determining region," or the term "CDR," includes an amino acid sequence encoded by a nucleic acid sequence of an organism's immunoglobulin genes that normally (i.e., in a wild-type animal) appears between two framework regions in a variable region of a light or a heavy chain of an immunoglobulin molecule (e.g., an antibody or a T cell receptor). A CDR can be encoded by, for example, a germline sequence or a rearranged or unrearranged sequence, and, for example, by a naïve or a mature B cell or a T cell. In some circumstances (e.g., for a CDR3), CDRs can be encoded by two or more sequences (e.g., germline sequences) that are not contiguous (e.g., in an unrearranged nucleic acid sequence) but are contiguous in a B cell nucleic acid sequence, e.g., as the result of splicing or connecting the sequences (e.g., V-D-J recombination to form a heavy chain CDR3).

The phrase "gene segment," or "segment" includes reference to a V (light or heavy) or D or J (light or heavy) immunoglobulin gene segment, which includes unrearranged sequences at immunoglobulin loci (in e.g., humans and mice) that can participate in a rearrangement (mediated by, e.g., endogenous recombinases) to form a rearranged V/J or V/D/J sequence. Unless indicated otherwise, the V, D, and J segments comprise recombination signal sequences (RSS) that allow for V/J recombination or V/D/J recombination according to the 12/23 rule. Unless indicated otherwise, the segments further comprise sequences with which they are associated in nature or functional equivalents thereof (e.g., for V segments promoter(s) and leader(s)).

The phrase "heavy chain," or "immunoglobulin heavy chain" includes an immunoglobulin heavy chain constant region sequence from any organism, and unless otherwise specified includes a heavy chain variable domain ($V_H$). $V_H$ domains include three heavy chain CDRs and four framework (FR) regions, unless otherwise specified. Fragments of heavy chains include CDRs, CDRs and FRs, and combinations thereof. A typical heavy chain consists essentially of, following the variable domain (from N-terminal to C-terminal), a $C_H1$ domain, a hinge, a $C_H2$ domain, a $C_H3$ domain, and optionally a $C_H4$ domain (e.g., in the case of IgM or IgE) and a transmembrane (M) domain (e.g., in the case of membrane-bound immunoglobulin on lymphocytes). A heavy chain constant region is a region of a heavy chain that extends (from N-terminal side to C-terminal side) from outside FR4 to the C-terminal of the heavy chain. Heavy chain constant regions with minor deviations, e.g., truncations of one, two, three or several amino acids from the C-terminal, would be encompassed by the phrase "heavy chain constant region," as well as heavy chain constant regions with sequence modifications, e.g., 1, 2, 3, 4, 5, 6, 7, 8, 9, or 10 amino acid substitutions. Amino acid substitutions can be made at one or more positions selected from, e.g. (with reference to EU numbering of an immunoglobulin constant region, e.g., a human IgG constant region), 228, 233, 234, 235, 236, 237, 238, 239, 241, 248, 249, 250, 252, 254, 255, 256, 258, 265, 267, 268, 269, 270, 272, 276, 278, 280, 283, 285, 286, 289, 290, 292, 293, 294, 295, 296, 297, 298, 301, 303, 305, 307, 308, 309, 311, 312, 315, 318, 320, 322, 324, 326, 327, 328, 329, 330, 331, 332, 333, 334, 335, 337, 338, 339, 340, 342, 344, 356, 358, 359, 360, 361, 362, 373, 375, 376, 378, 380, 382, 383, 384, 386, 388, 389, 398, 414, 416, 419, 428, 430, 433, 434, 435, 437, 438, and 439.

For example, and not by way of limitation, a heavy chain constant region can be modified to exhibit enhanced serum half-life (as compared with the same heavy chain constant region without the recited modification(s)) and have a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at 428 and/or 433 (e.g., L/R/SI/P/Q or K) and/or 434 (e.g., H/F or Y); or a modification at 250 and/or 428; or a modification at 307 or 308 (e.g., 308F, V308F), and 434. In another example, the modification can comprise a 428L (e.g., M428L) and 434S (e.g., N434S) modification; a 428L, 259I (e.g., V259I), and a 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); a 307 and/or 308 modification (e.g., 308F or 308P).

The phrase "light chain" includes an immunoglobulin light chain constant ($C_L$) region sequence from any organism, and unless otherwise specified includes human κ and λ light chains. Light chain variable ($V_L$) domains typically include three light chain CDRs and four framework (FR) regions, unless otherwise specified. Generally, a full-length light chain ($V_L+C_L$) includes, from amino terminus to carboxyl terminus, a $V_L$ domain that includes FR1-CDR1-FR2-CDR2-FR3-CDR3-FR4, and a $C_L$ region. Light chains ($V_L+C_L$) that can be used with this invention include those, e.g., that do not selectively bind either a first or second (in the case of bispecific binding proteins) epitope selectively bound by the binding protein (e.g., the epitope(s) selectively bound by the $V_L$ domain fused with the $C_H$ domain). $V_L$ domains that do not selectively bind the epitope(s) bound by the $V_L$ that is fused with the $C_H$ domain include those that can be identified by screening for the most commonly employed light chains in existing antibody libraries (wet libraries or in silico), wherein the light chains do not substantially interfere with the affinity and/or selectivity of the epitope binding domains of the binding proteins. Suitable light chains include those that can bind (alone or in combination with its cognate $V_L$ fused with the $C_H$ region) an epitope that is specifically bound by the $V_L$ fused to the $C_H$ region.

The phrase "micromolar range" is intended to mean 1-999 micromolar; the phrase "nanomolar range" is intended to mean 1-999 nanomolar; the phrase "picomolar range" is intended to mean 1-999 picomolar.

The term "non-human animals" is intended to include any vertebrate such as cyclostomes, bony fish, cartilaginous fish such as sharks and rays, amphibians, reptiles, mammals, and birds. Suitable non-human animals include mammals. Suitable mammals include non-human primates, goats, sheep, pigs, dogs, cows, and rodents. Suitable non-human animals are selected from the rodent family including rat and mouse. In one embodiment, the non-human animals are mice.

Mice, Nucleotide Sequences, and Binding Proteins

Binding proteins are provided that are encoded by elements of immunoglobulin loci, wherein the binding proteins comprise immunoglobulin heavy chain constant regions fused with immunoglobulin light chain variable domains. Further, multiple strategies are provided to genetically modify an immunoglobulin heavy chain locus in a mouse to encode binding proteins that contain elements encoded by immunoglobulin light chain loci. Such genetically modified mice represent a source for generating unique populations of binding proteins that have an immunoglobulin structure, yet exhibit an enhanced diversity over traditional antibodies.

Binding protein aspects described herein include binding proteins that are encoded by modified immunoglobulin loci, which are modified such that gene segments that normally (i.e., in a wild-type animal) encode immunoglobulin light chain variable domains (or portions thereof) are operably linked to nucleotide sequences that encode heavy chain constant regions. Upon rearrangement of the light chain gene segments, a rearranged nucleotide sequence is obtained that comprises a sequence encoding a light chain variable domain fused with a sequence encoding a heavy chain constant region. This sequence encodes a polypeptide that has an immunoglobulin light chain variable domain fused with a heavy chain constant region. Thus, in one embodiment, the polypeptide consists essentially of, from N-terminal to C-terminal, a $V_L$ domain, a $C_H1$ region, a hinge, a $C_H2$ region, a $C_H3$ region, and optionally a $C_H4$ region.

In modified mice described herein, such binding proteins are made that also comprise a cognate light chain, wherein in one embodiment the cognate light chain pairs with the polypeptide described above to make a binding protein that is antibody-like, but the binding protein comprises a $V_L$ region—not a $V_H$ region—fused to a $C_H$ region.

In various embodiments, the modified mice make binding proteins that comprise a $V_L$ region fused with a $C_H$ region (a hybrid heavy chain), wherein the $V_L$ region of the hybrid heavy chain exhibits an enhanced degree of somatic hypermutation. In these embodiments, the enhancement is over a $V_L$ region that is fused with a $C_L$ region (a light chain). In some embodiments, a $V_L$ region of a hybrid heavy chain exhibits about 1.5-fold, 2-fold, 2.5-fold, 3-fold, 3.5-fold, 4-fold, 4.5-fold, or 5-fold or more somatic hypermutations than a $V_L$ region fused with a $C_L$ region. In some embodiments, the modified mice in response to an antigen exhibit a population of binding proteins that comprise a $V_L$ region of a hybrid heavy chain, wherein the population of binding proteins exhibits an average of about 1.5-fold, 2-fold, 2.5-fold, 3-fold, 3.5-fold, 4-fold, 4.5-fold, 5-fold or more somatic hypermutations in the $V_L$ region of the hybrid heavy chain than is observed in a wild-type mouse in response to the same antigen. In one embodiment, the somatic hypermutations in the $V_L$ region of the hybrid heavy chain comprise one or more or two or more N additions in a CDR3.

In various embodiments, the binding proteins comprise variable domains encoded by immunoglobulin light chain sequences that comprise a larger number of N additions than observed in nature for light chains rearranged from an endogenous light chain locus, e.g., a binding protein comprising a mouse heavy chain constant region fused with a variable domain derived from human light chain V gene segments and human (light or heavy) J gene segments, wherein the human V and human J segments rearrange to form a rearranged gene that comprises 1, 2, 3, 4, 5, 6, 7, 8, 9, or 10 or more N additions.

In various embodiments, the mice of the invention make binding proteins that are on average smaller than wild-type antibodies (i.e., antibodies that have a $V_H$ domain), and possess advantages associated with smaller size. Smaller size is realized at least in part through the absence of an amino acid sequence encoded by a $D_H$ region, normally present in a $V_H$ domain. Smaller size can also be realized in the formation of a CDR3 that is derived, e.g., from a Vκ region and a Jκ region.

In another aspect, a mouse and a method is provided for providing a population of binding proteins having somatically hypermutated $V_L$ domains, e.g., somatically mutated human Vκ domains, and, e.g., human Vκ domains encoded by rearranged K variable genes that comprise 1-10 or more N additions. In one embodiment, in the absence of a $V_H$ region for generating antibody diversity, a mouse of the invention will generate binding proteins, e.g., in response to challenge with an antigen, whose V domains are only or substantially $V_L$ domains. The clonal selection process of the mouse therefore is limited to selecting only or substantially from binding proteins that have $V_L$ domains, rather than $V_H$ domains. Somatic hypermutation of the $V_L$ domains will be as frequent, or substantially more frequent (e.g., 2- to 5-fold higher, or more), than in wild-type mice (which also mutate $V_L$ domains with some frequency). The clonal selection process in a mouse of the invention will generate high affinity binding proteins from the modified immunoglobulin locus, including binding proteins that specifically bind an epitope with an affinity in the nanomolar or picomolar range. Sequences that encode such binding proteins can be used to make therapeutic binding proteins containing human variable regions and human constant regions using an appropriate expression system.

In other embodiments, a mouse according to the invention can be made wherein the mouse heavy chain and/or light chain immunoglobulin loci are disabled, rendered nonfunctional, or knocked out, and fully human or chimeric human-mouse transgenes can be placed in the mouse, wherein at least one of the transgenes contains a modified heavy chain locus (e.g., having light chain gene segments operably linked to one or more heavy chain gene sequences). Such a mouse may also make a binding protein as described herein.

In one aspect, a method is provided for increasing the diversity, including by somatic hypermutation or by N additions in a $V_L$ domain, comprising placing an unrearranged light chain V gene segment and an unrearranged J gene segment in operable linkage with a mouse $C_H$ gene sequence, exposing the animal to an antigen of interest, and isolating from the animal a rearranged and somatically hypermutated V(light)/J gene sequence of the animal, wherein the rearranged V(light)/J gene sequence is fused with a nucleotide sequence encoding an immunoglobulin $C_H$ region.

In one embodiment, the immunoglobulin heavy chain fused with the hypermutated $V_L$ is an IgM; in another embodiment, an IgG; in another embodiment, an IgE; in another embodiment, an IgA.

In one embodiment, the somatically hypermutated and class-switched $V_L$ domain contains about 2- to 5-fold or more of the somatic hypermutations observed for a rearranged and class-switched antibody having a $V_L$ sequence that is operably linked to a $C_L$ sequence. In one embodiment, the observed somatic hypermutations in the somatically hypermutated $V_L$ domain are about the same in number as observed in a $V_H$ domain expressed from a $V_H$ gene fused to a $C_H$ region.

In one aspect, a method for making a high-affinity human $V_L$ domain is provided, comprising exposing a mouse of the invention to an antigen of interest, allowing the mouse to develop an immune response to the antigen of interest, and isolating a somatically mutated, class-switched human $V_L$ domain from the mouse that specifically binds the antigen of interest with high affinity.

In one embodiment, the $K_D$ of a binding protein comprising the somatically mutated, class-switched human $V_L$ domain is in the nanomolar or picomolar range.

In one embodiment, the binding protein consists essentially of a polypeptide dimer, wherein the polypeptide consists essentially of the somatically mutated, class-switched binding protein comprising a human $V_L$ domain fused with a human $C_H$ region.

In one embodiment, the binding protein consists essentially of a polypeptide dimer and two light chains, wherein the polypeptide consists essentially of the somatically mutated, class-switched binding protein having a human $V_L$ domain fused with a human $C_H$ region; and wherein each polypeptide of the dimer is associated with a cognate light chain comprising a cognate light chain $V_L$ domain and a human $C_L$ region.

In one aspect, a method is provided for somatically hypermutating a human $V_L$ gene sequence, comprising placing a human $V_L$ gene segment and a human $J_L$ gene segment in operable linkage with an endogenous mouse $C_H$ gene at an endogenous mouse heavy chain immunoglobulin locus, exposing the mouse to an antigen of interest, and obtaining from the mouse a somatically hypermutated human $V_L$ gene sequence that binds the antigen of interest.

In one embodiment, the method further comprises obtaining from the mouse a $V_L$ gene sequence from a light chain that is cognate to the human somatically hypermutated human $V_L$ gene sequence that binds the antigen of interest.

$V_L$ Binding Proteins with $D_H$ Sequences

In various aspects, mice comprising an unrearranged immunoglobulin light chain V gene segment and an unrearranged (e.g., light or heavy) J gene segment also comprise an unrearranged DH gene segment that is capable of recombining with the J segment to form a rearranged D/J sequence, which in turn is capable of rearranging with the light chain V segment to form a rearranged variable sequence derived from (a) the light chain V segment, (b) the DH segment, and (c) the (e.g., light or heavy) J segment; wherein the rearranged variable sequence is operably linked to a heavy chain constant sequence (e.g., selected from CH1, hinge, CH2, CH3, and a combination thereof; e.g., operably linked to a mouse or human CH1, a hinge, a CH2, and a CH3).

In various aspects, mice comprising unrearranged human light chain V segments and J segments that also comprise a human D segment are useful, e.g., as a source of increased diversity of CDR3 sequences. Normally, CDR3 sequences arise in light chains from V/J recombination, and in heavy chains from V/D/J recombination. Further diversity is provided by nucleotide additions that occur during recombination (e.g., N additions), and also as the result of somatic hypermutation. Binding characteristics conferred by CDR3 sequences are generally limited to those conferred by the light chain CDR3 sequence, the heavy chain CDR3 sequence, and a combination of the light and the heavy chain CDR3 sequence, as the case may be. In mice as described herein, however, an added source of diversity is available due to binding characteristics conferred as the result of a combination of a first light chain CDR3 (on the heavy chain polypeptide) and a second light chain CDR3 (on the light chain polypeptide). Further diversity is possible where the first light chain CDR3 may contain a sequence derived from a D gene segment, as from a mouse as described herein that comprises an unrearranged V segment from a light chain V region operably linked to a D segment and operably linked to a J segment (light or heavy), employing the RSS engineering as taught here.

Another source of diversity is the N and/or P additions that can occur in the V(light)/J or V(light)/D/J recombinations that are possible in mice as described. Thus, mice described herein not only provide a different source of diversity (light chain-light chain) but also a further source of diversity due to the addition of, e.g., 1, 2, 3, 4, 5, 6, 7, 8, 9, or 10 or more N additions in a rearranged V(light)/J or a rearranged V(light)/D/J gene in a mouse as described herein.

In various aspects the use of a D gene segment operably linked to a J gene segment and a light chain V gene segment provides an enhanced diversity. Operable linkage of a DH segment in this instance will require that that D segment is capable of recombining with the J segment with which it is recited. Thus, the D segment will require to have juxtaposed a downstream RSS that is matched to the RSS juxtaposed upstream of the J segment such that the D segment and the J segment may rearrange. Further, the D segment will require an appropriate RSS juxtaposed upstream that is matched to the RSS juxtaposed downstream of the V segment such that the rearranged D/J segment and the V segment may rearrange to form a gene encoding a variable domain.

An RSS, or a recombination signal sequence, comprises a conserved nucleic acid heptamer sequence separated, by 12 base pairs (bp) or 23 base pairs (bp) of unconserved sequence, from a conserved nucleic acid nonamer sequence. RSS's are used by recombinases to achieve joining of immunoglobulin gene segments during the rearrangement process following the 12/23 rule. According to the 12/23 rule, a gene segment juxtaposed with an RSS having a 12 bp (unconserved) spacer rearranges with a gene segment juxtaposed with an RSS having a 23 bp (unconserved) spacer; i.e., rearrangements between gene segments each having an RSS with a 12 bp spacer, or each having an RSS with a 23 bp spacer, are generally not observed.

In the case of the λ light chain locus, variable gene segments (Vλ gene segments) are flanked downstream (with respect to the direction of transcription of the V sequence) with an RSS having a 23-mer spacer, and joining gene segments (Jλ gene segments) are flanked upstream (with respect to the direction of transcription of the J sequence) with an RSS having a 12-mer spacer. Thus, Vλ and Jλ segments are flanked with RSS's that are compatible under the 12/23 rule, and therefore are capable of recombine during rearrangement.

At the κ locus in a wild-type organism, however, each functional Vκ segment is flanked downstream with an RSS having a 12-mer spacer. Jκ segments, therefore, have 23-mer spaces juxtaposed on the upstream side of the Jκ segment. At the heavy chain locus, $V_H$ gene segments are juxtaposed downstream with an RSS having a 23-mer spacer, followed by $D_H$ segment juxtaposed upstream and downstream with a 12-mer spacer, and $J_H$ segments each with a 23-mer segment juxtaposed on the upstream side of the $J_H$ segment. At the heavy chain locus, D/J recombination occurs first, mediated by the downstream $D_H$ RSS with the 12-mer spacer and the upstream $J_H$ RSS with the 23-mer spacer, to yield an intermediate rearranged D-J sequence having an RSS juxtaposed on the upstream side that has an RSS with a 12-mer spacer. The rearranged D-J segment having the RSS with the 12-mer juxtaposed on the upstream side then rearranges with the $V_H$ segment having the RSS with the 23-mer juxtaposed on its downstream side to form a rearranged V/D/J sequence.

In one embodiment, a Vλ segment is employed at the heavy chain locus with a J gene segment that is a Jλ segment, wherein the Vλ segment comprises an RSS juxtaposed on the downstream side of the Vλ sequence, and the RSS comprises a 23-mer spacer, and the J segment is a Jλ segment with an RSS juxtaposed on its upstream side having a 12-mer spacer (e.g., as found in nature).

In one embodiment, a Vλ segment is employed at the heavy chain locus with a J gene segment that is a Jκ or a $J_H$ gene segment, wherein the Vλ sequence has juxtaposed on its downstream side an RSS comprising a 23-mer spacer, and the Jκ or $J_H$ segment has juxtaposed on its upstream side an RSS comprising a 12-mer spacer.

In one embodiment, a Vλ segment is employed at the heavy chain locus with a $D_H$ gene segment and a J gene segment. In one embodiment, the Vλ segment comprises an RSS juxtaposed on the downstream side of the VA sequence with an RSS having a 23-mer spacer; the $D_H$ segment comprises an RSS juxtaposed on the upstream side and on the downstream side of the $D_H$ sequence with an RSS having a 12-mer spacer; and a J segment having an RSS juxtaposed on its upstream side having a 23-mer spacer, wherein the J segment is selected from a Jλ, a Jκ, and a $J_H$.

In one embodiment, a Vκ segment is employed at the heavy chain locus with a J gene segment (with no intervening D segment), wherein the Vκ segment has an RSS juxtaposed on the downstream side of the Vκ segment that comprises a 12-mer spaced RSS, and the J segment has juxtaposed on its upstream side a 23-mer spaced RSS, and the Jκ segment is selected from a Jκ segment, a Jλ segment, and a $J_H$ segment. In one embodiment, the V segment and/or the J segment are human.

In one embodiment, the Vκ segment is employed at the heavy chain locus with a D segment and a J segment, wherein the Vκ segment has an RSS juxtaposed on the downstream side of the Vκ segment that comprises a 12-mer spaced RSS, the D segment has juxtaposed on its upstream and downstream side a 23-mer spaced RSS, and the J segment has juxtaposed on its upstream side a 12-mer spaced RSS. In one embodiment, the J segment is selected from a Jκ segment, a Jλ segment, and a $J_H$ segment. In one embodiment, the V segment and/or the J segment are human.

A Jλ segment with an RSS having a 23-mer spacer juxtaposed at its upstream end, or a Jκ or $J_H$ segment with an RSS having a 12-mer spacer juxtaposed at its upstream end, is made using any suitable method for making nucleic acid sequences that is known in the art. A suitable method for making a J segment having an RSS juxtaposed upstream wherein the RSS has a selected spacer (e.g., either 12-mer or 23-mer) is to chemically synthesize a nucleic acid comprising the heptamer, the nonamer, and the selected spacer and fuse it to a J segment sequence that is either chemically synthesized or cloned from a suitable source (e.g., a human sequence source), and employ the fused J segment sequence and RSS in a targeting vector to target the RSS-J to a suitable site.

A D segment with a 23-mer spaced RSS juxtaposed upstream and downstream can be made by any method known in the art. One method comprises chemically synthesizing the upstream 23-mer RSS and D segment sequence and the downstream 23-mer RSS, and placing the RSS-flanked D segment in a suitable vector. The vector may be directed to replace one or more mouse D segments with a human D segment with 12-mer RSS sequences juxtaposed on the upstream and downstream sides, or directed to be inserted into, e.g., a humanized locus at a position between a human V segment and a human or mouse J segment.

Suitable nonamers and heptamers for RSS construction are known in the art (e.g., see Janeway's Immunobiology, 7th ed., Murphy et al., (2008, Garland Science, Taylor & Francis Group, LLC) at page 148, FIG. 4.5, incorporated by reference). Suitable nonconserved spacer sequences include, e.g., spacer sequences observed in RSS sequences at human or mouse immunoglobulin loci.

Bispecific-Binding Proteins

The binding proteins described herein, and nucleotide sequences encoding them, can be used to make multispecific binding proteins, e.g., bispecific binding proteins. In this aspect, a first polypeptide consisting essentially of a first $V_L$ domain fused with a $C_H$ region can associate with a second polypeptide consisting essentially of a second $V_L$ domain fused with a $C_H$ region. Where the first $V_L$ domain and the second $V_L$ domain specifically bind a different epitope, a bispecific-binding molecule can be made using the two $V_L$ domains. The $C_H$ region can be the same or different. In one embodiment, e.g., one of the $C_H$ regions can be modified so as to eliminate a protein A binding determinant, whereas the other heavy chain constant region is not so modified. This particular arrangement simplifies isolation of the bispecific binding protein from, e.g., a mixture of homodimers (e.g., homodimers of the first or the second polypeptides).

In one aspect, the methods and compositions described herein are used to make bispecific-binding proteins. In this aspect, a first $V_L$ that is fused to a $C_H$ region and a second $V_L$ that is fused to a $C_H$ region are each independently cloned in frame with a human IgG sequence of the same isotype (e.g., a human IgG1, igG2, IgG3, or IgG4). The first $V_L$ specifically binds a first epitope, and the second $V_L$ specifically binds a second epitope. The first and second epitopes may be on different antigens, or on the same antigen.

In one embodiment, the IgG isotype of the $C_H$ region fused to the first $V_L$ and the IgG isotype of the $C_H$ region fused to the second $V_L$ are the same isotype, but differ in that one IgG isotype comprises at least one amino acid substitution. In one embodiment, the at least one amino acid substitution renders the heavy chain bearing the substitution unable or substantially unable to bind protein A as compared with the heavy chain that lacks the substitution.

In one embodiment, the first $C_H$ region comprises a first $C_H3$ domain of a human IgG selected from IgG1, IgG2, and IgG4; and the second $C_H$ region comprises a second $C_H3$ domain of a human IgG selected from IgG1, IgG2, and IgG4, wherein the second $C_H3$ domain comprises a modification that reduces or eliminates binding of the second $C_H3$ domain to protein A.

In one embodiment, the second $C_H3$ domain comprises a 435R modification, numbered according to the EU index of Kabat. In another embodiment, the second $C_H3$ domain further comprises a 436F modification, numbered according to the EU index of Kabat.

In one embodiment, the second $C_H3$ domain is that of a human IgG1 that comprises a modification selected from the group consisting of D356E, L358M, N384S, K392N, V397M, and V422I, numbered according to the EU index of Kabat.

In one embodiment, the second $C_H3$ domain is that of a human IgG2 that comprises a modification selected from the group consisting of N384S, K392N, and V422I, numbered according to the EU index of Kabat.

In one embodiment, the second $C_H3$ domain is that of a human IgG4 comprising a modification selected from the group consisting of Q355R, N384S, K392N, V397M, R409K, E419Q, and V422I, numbered according to the EU index of Kabat.

In one embodiment, the binding protein comprises $C_H$ regions having one or more modifications as recited herein, wherein the constant region of the binding protein is non-immunogenic or substantially nonimmunogenic in a human. In a specific embodiment, the $C_H$ regions comprise amino acid sequences that do not present an immunogenic epitope in a human. In another specific embodiment, the binding protein comprises a $C_H$ region that is not found in a wild-type human heavy chain, and the $C_H$ region does not comprise a sequence that generates a T-cell epitope.

EXAMPLES

The following examples are provided so as to describe how to make and use methods and compositions of the invention, and are not intended to limit the scope of what the inventors regard as their invention. Unless indicated otherwise, temperature is indicated in Celsius, and pressure is at or near atmospheric.

Example I

Introduction of Light Chain Gene Segments into a Heavy Chain Locus

Various targeting constructs were made using VELOCI-GENE® genetic engineering technology (see, e.g., U.S. Pat. No. 6,586,251 and Valenzuela, D. M., Murphy, A. J., Frendewey, D., Gale, N. W., Economides, A. N., Auerbach, W., Poueymirou, W. T., Adams, N. C., Rojas, J., Yasenchak, J., Chernomorsky, R., Boucher, M., Elsasser, A. L., Esau, L., Zheng, J., Griffiths, J. A., Wang, X., Su, H., Xue, Y., Dominguez, M. G., Noguera, I., Torres, R., Macdonald, L. E., Stewart, A. F., DeChiara, T. M., Yancopoulos, G. D. (2003). High-throughput engineering of the mouse genome coupled with high-resolution expression analysis. Nat Biotechnol 21, 652-659) to modify mouse genomic Bacterial Artificial Chromosome (BAC) libraries. Mouse BAC DNA was modified by homologous recombination to inactivate the endogenous mouse heavy chain locus through targeted deletion of $V_H$, $D_H$ and $J_H$ gene segments for the ensuing insertion of unrearranged human germline κ light chain gene sequences (top of FIG. 2).

Briefly, the mouse heavy chain locus was deleted in two successive targeting events using recombinase-mediated recombination. The first targeting event included a targeting at the 5' end of the mouse heavy chain locus using a targeting vector comprising from 5' to 3' a 5' mouse homology arm, a recombinase recognition site, a neomycin cassette and a 3' homology arm. The 5' and 3' homology arms contained sequence 5' of the mouse heavy chain locus. The second targeting event included a targeting at the 3' end of the mouse heavy chain locus in the region of the $J_H$ gene segments using a second targeting vector that contained from 5' to 3' a 5' mouse homology arm, a 5' recombinase recognition site, a second recombinase recognition site, a hygromycin cassette, a third recombinase recognition site, and a 3' mouse homology arm. The 5' and 3' homology arms contained sequence flanking the mouse $J_H$ gene segments and 5' of the intronic enhancer and constant regions. Positive ES cells containing a modified heavy chain locus targeted with both targeting vectors (as described above) were confirmed by karyotyping. DNA was then isolated from the double-targeted ES cells and subjected to treatment with a recombinase thereby mediating the deletion of genomic DNA of the mouse heavy chain locus between the 5' recombinase recognition site in the first targeting vector and the 5' recombinase recognition site in the second targeting vector, leaving a single recombinase recognition site and the hygromycin cassette flanked by two recombinase recognition sites (see top of FIG. 2). Thus a modified mouse heavy chain locus containing intact $C_H$ genes was created for progressively inserting human κ germline gene segments in a precise manner using targeting vectors described below.

Figure 1B:
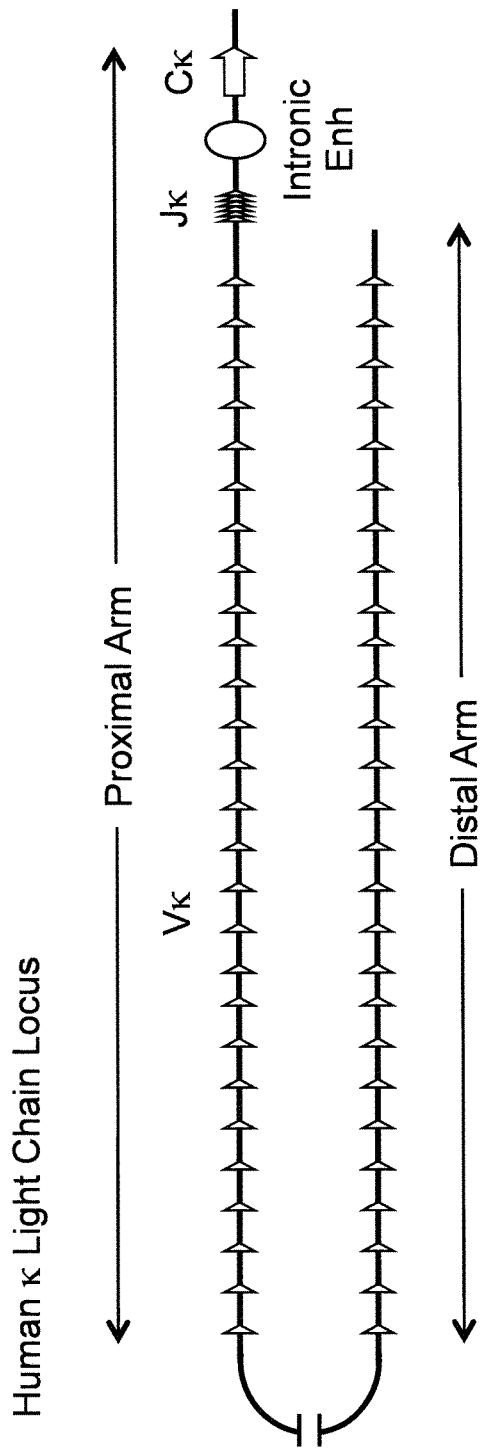
FIG. 1B illustrates a schematic (not to scale) of the human κ light chain locus. The human κ light chain locus is duplicated into distal and proximal contigs of opposite polarity spanning about 440 kb and 600 kb, respectively. Between the two contigs is about 800 kb of DNA that is believed to be free of Vκ gene segments. The human κ light chain locus contains about 76 Vκ gene segments, 5 Jκ gene segments, an intronic enhancer (Enh) and a single constant region (Cκ).
Figure 2:
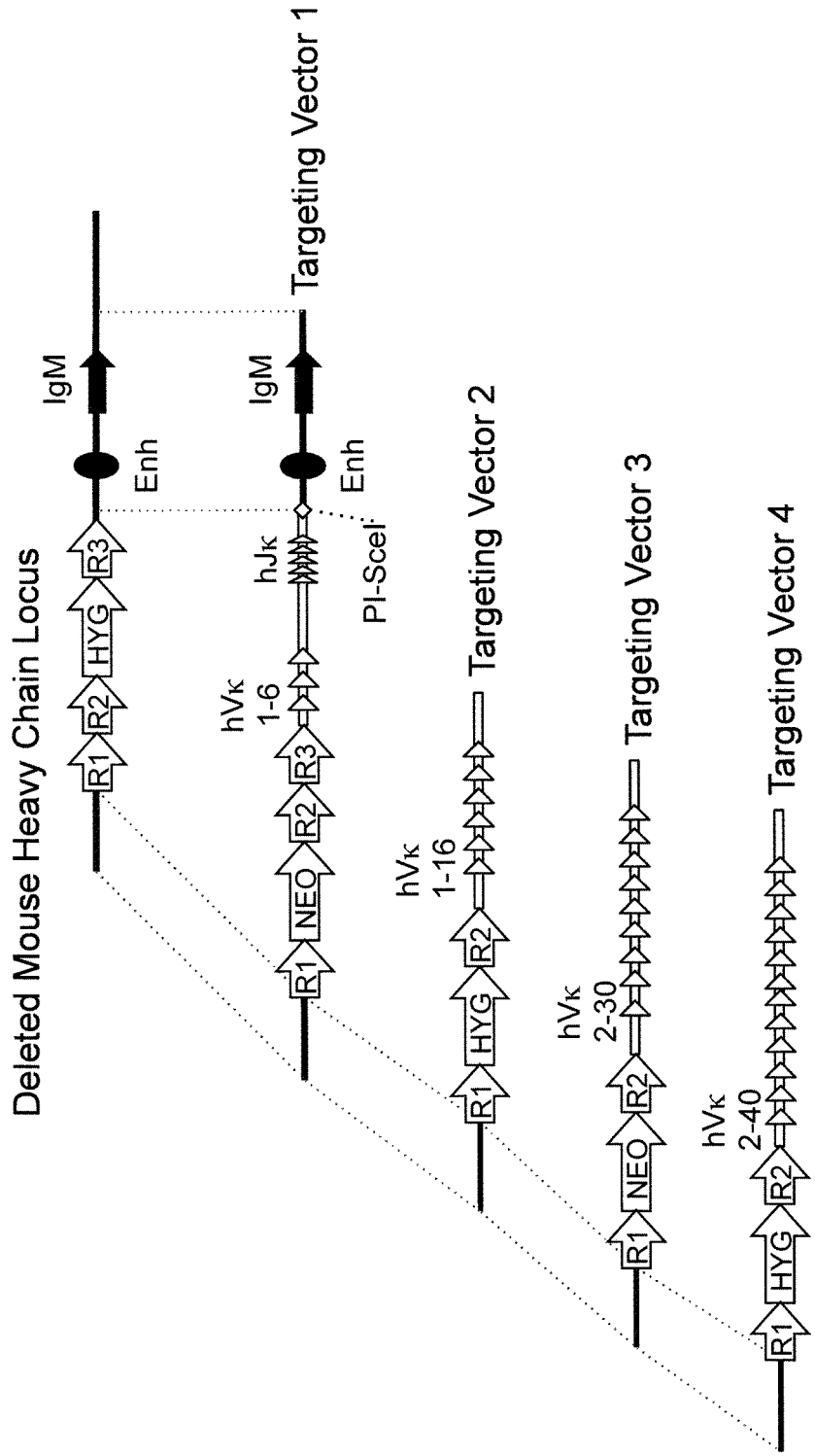
FIG. 2 shows a targeting strategy for progressive insertion of 40 human Vκ and 5 human Jκ gene segments into the mouse heavy chain locus. Hygromycin (HYG) and Neomycin (NEO) selection cassettes are shown with recombinase recognition sites (R1, R2, etc.).

Four separate targeting vectors were engineered to progressively insert 40 human Vκ gene segments and five human Jκ gene segments into the inactivated mouse heavy chain locus (described above) using standard molecular techniques recognized in the art (FIG. 2). The human κ gene segments used for engineering the four targeting constructs are naturally found in proximal contig of the germline human κ light chain locus (FIG. 1B and Table 1).

A ~110,499 bp human genomic fragment containing the first six human Vκ gene segments and five human Jκ gene segments was engineered to contain a PI-SceI site 431 bp downstream (3') of the human Jκ5 gene segment. Another PI-SceI site was engineered at the 5' end of a ~7,852 bp genomic fragment containing the mouse heavy chain intronic enhancer, the IgM switch region (Sp) and the IgM gene of the mouse heavy chain locus. This mouse fragment was used as a 3' homology arm by ligation to the ~110.5 kb human fragment, which created a 3' junction containing, from 5' to 3', ~110.5 kb of genomic sequence of the human κlight chain locus containing the first six consecutive Vκ gene segments and five Jκ gene segments, a PI-SceI site, ~7,852 bp of mouse heavy chain sequence containing the mouse intronic enhancer, Sp and the mouse IgM constant gene. Upstream (5') from the human Vκ1-6 gene segment was an additional 3,710 bp of human κ sequence before the start of the 5' mouse homology arm, which contained 19,752 bp of mouse genomic DNA corresponding to sequence 5' of the mouse heavy chain locus. Between the 5' homology arm and the beginning of the human κ sequence was a neomycin cassette flanked by three recombinase recognition sites (see Targeting Vector 1, FIG. 2). The final targeting vector for the first insertion of human κ sequence from 5' to 3' included a 5' homology arm containing ~20 kb of mouse genomic sequence 5' of the heavy chain locus, a first recombinase recognition site (R1), a neomycin cassette, a second recombinase recognition site (R2), a third recombinase recognition site (R3), ~110.5 kb of human genomic κ sequence containing the first six consecutive human Vκ gene segments and five human Jκ gene segments, a PI-SceI site, and a 3' homology arm containing ~8 kb of mouse genomic sequence including the intronic enhancer, Sμ and the mouse IgM constant gene (see FIG. 2, Targeting Vector 1). Homologous recombination with this targeting vector created a modified mouse heavy chain locus containing six human Vκ gene segments and five human Jκ gene segments operably linked to the endogenous mouse heavy chain constant genes which, upon recombination, leads to the formation of a hybrid heavy chain (i.e., a human Vκ domain and a mouse $C_H$ region).

TABLE 1

| Targeting Vector | Size of Human κ Sequence | Human κ Gene Segments Added | |
|---|---|---|---|
| | | Vκ | Jκ |
| 1 | ~110.5 kb | 4-1, 5-2, 7-3, 2-4, 1-5, 1-6 | 1-5 |
| 2 | ~140 kb | 3-7, 1-8, 1-9, 2-10, 3-11, 1-12, 1-13, 2-14, 3-15, 1-16 | — |
| 3 | ~161 kb | 1-17, 2-18, 2-19, 3-20, 6-21, 1-22, 1-23, 2-24, 3-25, 2-26, 1-27, 2-28, 2-29, 2-30 | — |

TABLE 1-continued

| Targeting Vector | Size of Human κ Sequence | Human κ Gene Segments Added | |
|---|---|---|---|
| | | Vκ | Jκ |
| 4 | ~90 kb | 3-31, 1-32, 1-33, 3-34, 1-35, 2-36, 1-37, 2-38, 1-39, 2-40 | — |

Introduction of Ten Additional Human Vκ Gene Segments into a Hybrid Heavy Chain Locus.

A second targeting vector was engineered for introduction of 10 additional human Vκ gene segments to the modified mouse heavy chain locus described above (see FIG. 2, Targeting Vector 2). A 140,058 bp human genomic fragment containing 12 consecutive human Vκ gene segments from the human κ light chain locus was engineered with a 5' homology arm containing mouse genomic sequence 5' of the mouse heavy chain locus and a 3' homology arm containing human genomic κ sequence. Upstream (5') from the human Vκ1-16 gene segment was an additional 10,170 bp of human κ sequence before the start of the 5' mouse homology arm, which was the same 5' homology arm used for construction of Targeting Vector 1 (see FIG. 2). Between the 5' homology arm and the beginning of the human κ sequence was a hygromycin cassette flanked by recombinase recognition sites. The 3' homology arm included a 31,165 bp overlap of human genomic κ sequence corresponding to the equivalent 5' end of the ~110.5 kb fragment of human genomic κ sequence of Targeting Vector 1 (FIG. 2). The final targeting vector for the insertion of 10 additional human Vκ gene segments from 5' to 3' included a 5' homology arm containing ~20 kb of mouse genomic sequence 5' of the heavy chain locus, a first recombinase recognition site (R1), a hygromycin cassette, a second recombinase recognition site (R2) and ~140 kb of human genomic κ sequence containing 12 consecutive human Vλ gene segments, ~31 kb of which overlaps with the 5' end of the human κ sequence of Targeting Vector 1 and serves as the 3' homology arm for this targeting construct. Homologous recombination with this targeting vector created a modified mouse heavy chain locus containing 16 human Vκ gene segments and five human Jκ gene segments operably linked to the mouse heavy chain constant genes which, upon recombination, leads to the formation of a hybrid heavy chain.

Introduction of Fourteen Additional Human Vκ Gene Segments into a Hybrid Heavy Chain Locus.

A third targeting vector was engineered for introduction of 14 additional human Vκ gene segments to the modified mouse heavy chain locus described above (see FIG. 2, Targeting Vector 3). A 160,579 bp human genomic fragment containing 15 consecutive human Vκ gene segments was engineered with a 5' homology arm containing mouse genomic sequence 5' of the mouse heavy chain locus and a 3' homology arm containing human genomic κ sequence. Upstream (5') from the human Vκ2-30 gene segment was an additional 14,687 bp of human κ sequence before the start of the 5' mouse homology arm, which was the same 5' homology used for the previous two targeting vectors (described above, see also FIG. 2). Between the 5' homology arm and the beginning of the human κ sequence was a neomycin cassette flanked by recombinase recognition sites. The 3' homology arm included a 21,275 bp overlap of human genomic κ sequence corresponding to the equivalent 5' end of the ~140 kb fragment of human genomic κ sequence of Targeting Vector 2 (FIG. 2). The final targeting vector for the insertion of 14 additional human Vκ gene segments from 5' to 3' included a 5' homology arm containing ~20 kb of mouse genomic sequence 5' of the mouse heavy chain locus, a first recombinase recognition site (R1), a neomycin cassette, a second recombinase recognition site (R2) and ~161 kb of human genomic κ sequence containing 15 human Vκ gene segments, ~21 kb of which overlaps with the 5' end of the human κ sequence of Targeting Vector 2 and serves as the 3' homology arm for this targeting construct. Homologous recombination with this targeting vector created a modified mouse heavy chain locus containing 30 human Vκ gene segments and five human Jκ gene segments operably linked to the mouse heavy chain constant genes which, upon recombination, leads to the formation of a chimeric κ heavy chain.

Introduction of Ten Additional Human Vκ Gene Segments into a Hybrid Heavy Chain Locus.

Figure 3:
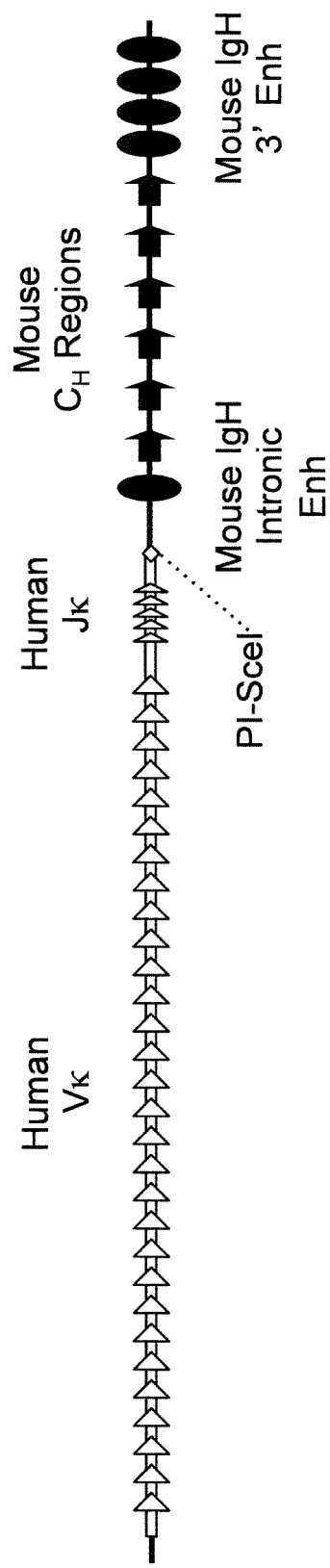
FIG. 3 shows a modified mouse heavy chain locus comprising human Vκ and Jκgene segments operably linked to mouse $C_H$ regions.

A fourth targeting vector was engineered for introduction of 10 additional human Vκ gene segments to the modified mouse heavy chain locus described above (see FIG. 2, Targeting Vector 4). A 90,398 bp human genomic fragment containing 16 consecutive human Vκ gene segments was engineered with a 5' homology arm containing mouse genomic sequence 5' of the mouse heavy chain locus and a 3' homology arm containing human genomic κ sequence. Upstream (5') from the human Vκ2-40 gene segment was an additional 8,484 bp of human κ sequence before the start of the 5' mouse homology arm, which was the same 5' homology as the previous targeting vectors (described above, see also FIG. 2). Between the 5' homology arm and the beginning of the human κ sequence was a hygromycin cassette flanked by recombinase recognition sites. The 3' homology arm included a 61,615 bp overlap of human genomic κ sequence corresponding to the equivalent 5' end of the ~160 kb fragment of human genomic κ sequence of Targeting Vector 3 (FIG. 2). The final targeting vector for the insertion of 10 additional human Vκ gene segments from 5' to 3' included a 5' homology arm containing ~20 kb of mouse genomic sequence 5' of the mouse heavy chain locus, a first recombinase recognition site (R1), a hygromycin cassette, a second recombinase recognition site (R2) and ~90 kb of human genomic κ sequence containing 16 human Vκ gene segments, ~62 kb of which overlaps with the 5' end of the human κ sequence of Targeting Vector 3 and serves as the 3' homology arm for this targeting construct. Homologous recombination with this targeting vector created a modified mouse heavy chain locus containing 40 human Vκ gene segments and five human Jκ gene segments operably linked to the mouse heavy chain constant genes which, upon recombination, leads to the formation of a chimeric κ heavy chain (FIG. 3).

Figure 4A:
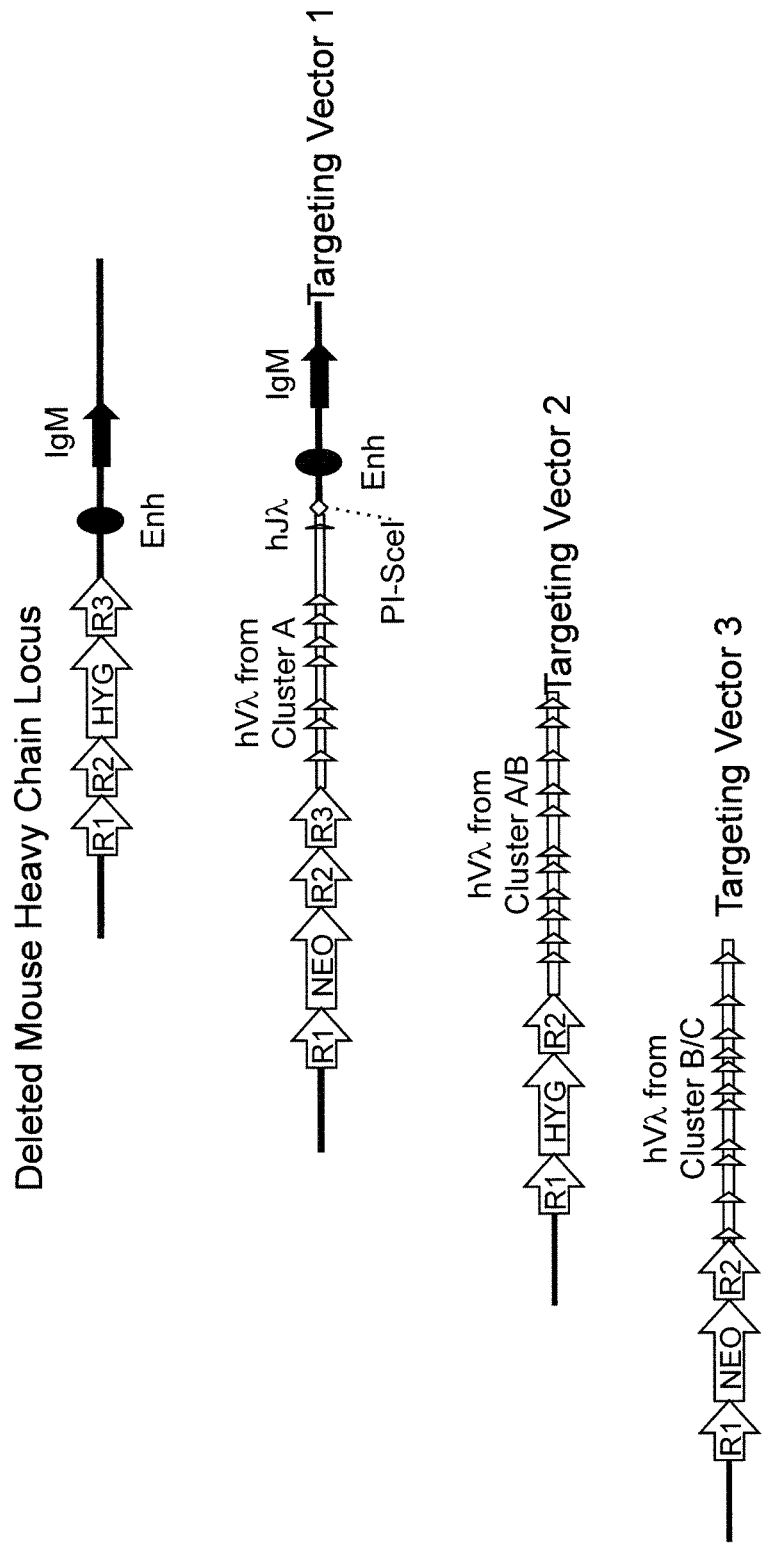
FIG. 4A shows an exemplary targeting strategy for progressive insertion of human Vλ and a single human Jλ gene segment into the mouse heavy chain locus. Hygromycin (HYG) and Neomycin (NEO) selection cassettes are shown with recombinase recognition sites (R1, R2, etc.).
Figure 4B:
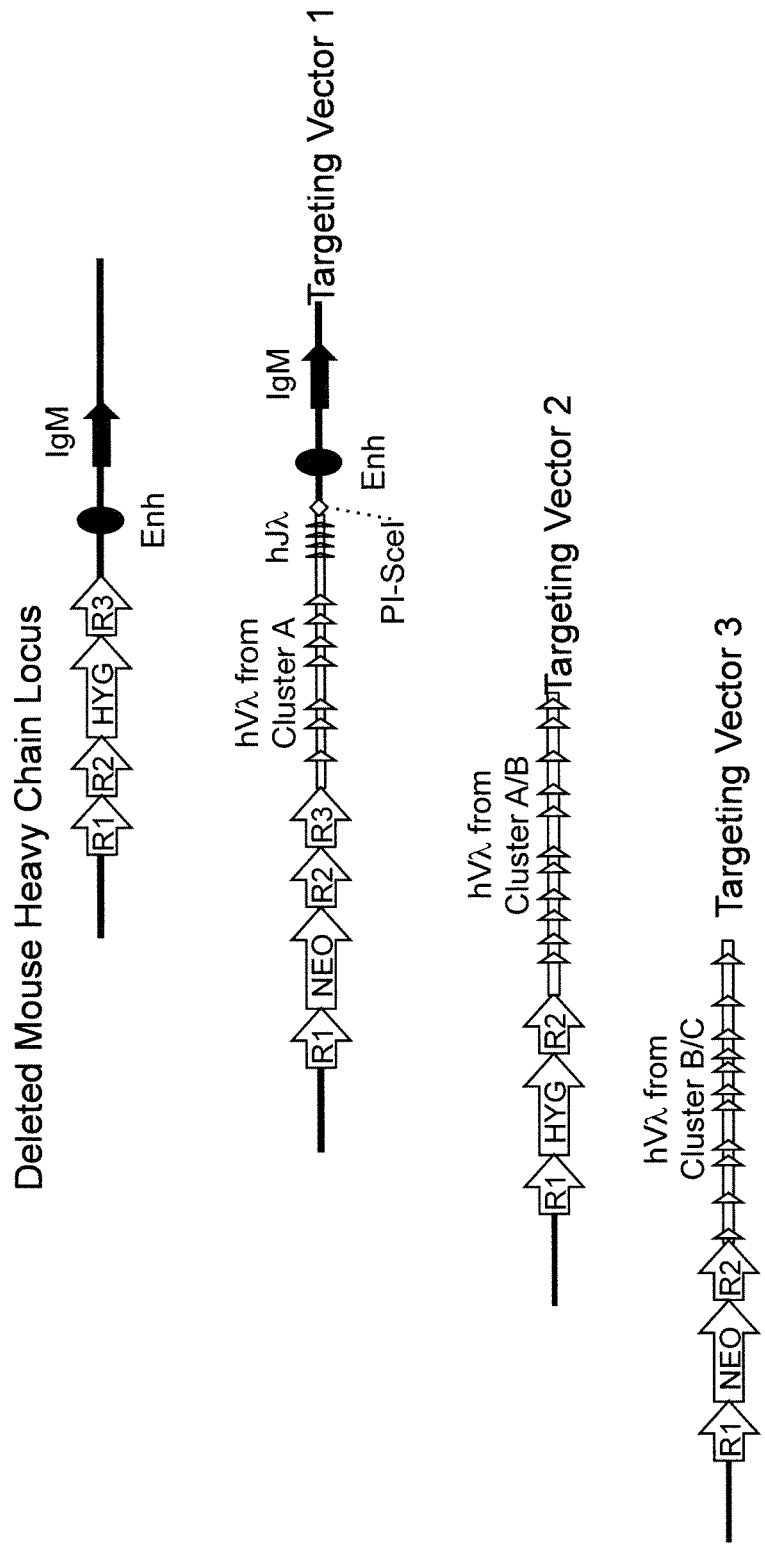
FIG. 4B shows an exemplary targeting strategy for progressive insertion of human Vλ and four human Jλ gene segments into the mouse heavy chain locus. Hygromycin (HYG) and Neomycin (NEO) selection cassettes are shown with recombinase recognition sites (R1, R2, etc.).

Using a similar approach as described above, other combinations of human light chain variable domains in the context of mouse heavy chain constant regions are constructed. Additional light chain variable domains may be derived from human Vλ and Jλ gene segments (FIGS. 4A and 4B).

The human λ light chain locus extends over 1,000 kb and contains over 80 genes that encode variable (V) or joining (J) segments. Among the 70 Vλ gene segments of the human λ light chain locus, anywhere from 30-38 appear to be functional gene segments according to published reports. The 70 Vλ sequences are arranged in three clusters, all of which contain different members of distinct V gene family groups (clusters A, B and C). Within the human λ light chain locus, over half of all observed Vλ domains are encoded by the gene segments 1-40, 1-44, 2-8, 2-14, and 3-21. There are seven Jλ gene segments, only four of which are regarded as generally functional Jλ gene segments—Jλ1, Jλ2, Jλ3, and Jλ7. In some alleles, a fifth Jλ-Cλ gene segment pair is reportedly a pseudo gene (Cλ6). Incorporation of multiple human Jλ gene segments into a hybrid heavy chain locus, as described herein, is constructed by de novo synthesis. In this way, a genomic fragment containing multiple human Jλ gene segments in germline configuration is engineered with multiple human Vλ gene segments and allow for normal V-J recombination in the context of a heavy chain constant region.

Coupling light chain variable domains with heavy chain constant regions represents a potentially rich source of diversity for generating unique $V_L$ binding proteins with human $V_L$ regions in non-human animals. Exploiting this diversity of the human λ light chain locus (or human κ locus as described above) in mice results in the engineering of unique hybrid heavy chains and gives rise to another dimension of binding proteins to the immune repertoire of genetically modified animals and their subsequent use as a next generation platform for the generation of therapeutics.

Figure 5A:
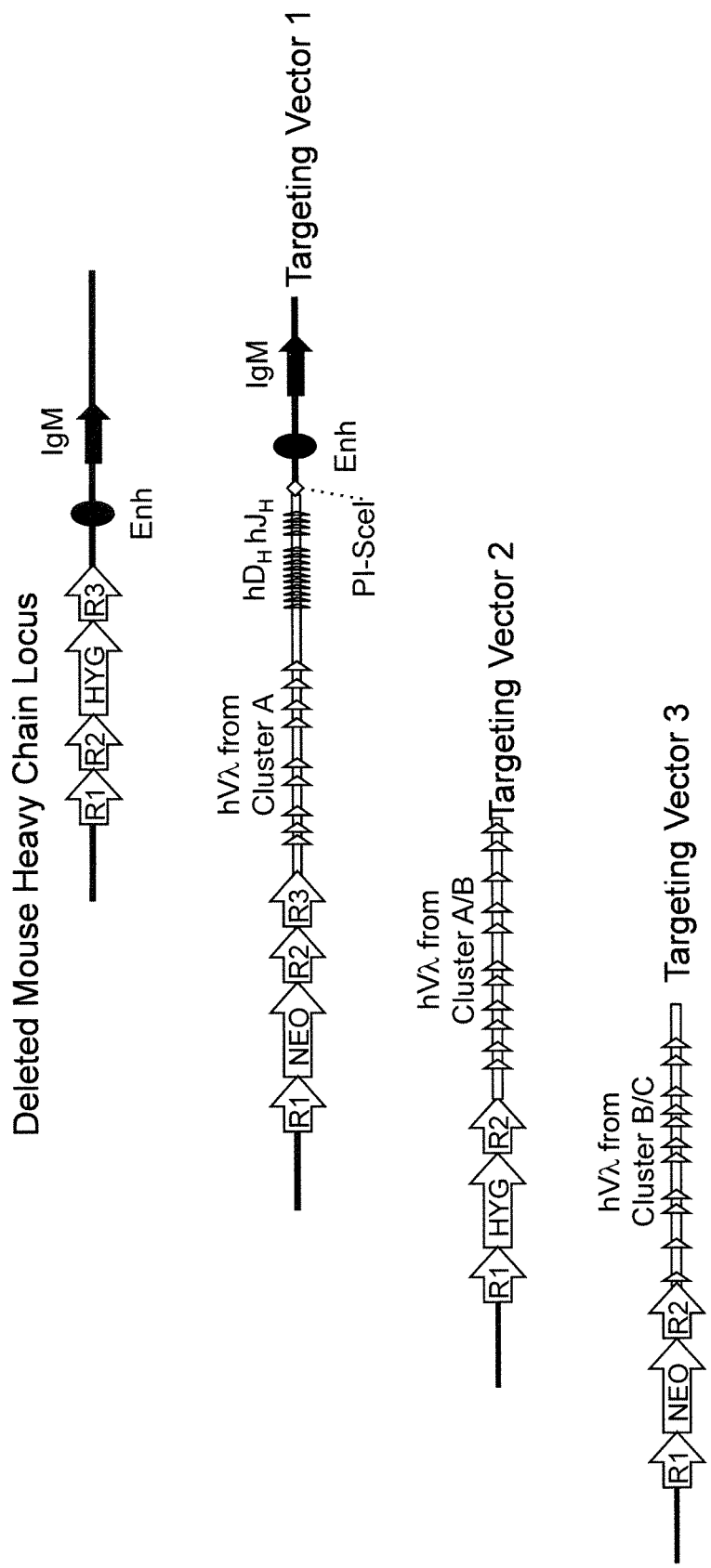
FIG. 5A shows an exemplary targeting strategy for progressive insertion of human Vλ, human $D_H$ and human $J_H$ gene segments into the mouse heavy chain locus. Hygromycin (HYG) and Neomycin (NEO) selection cassettes are shown with recombinase recognition sites (R1, R2, etc.).
Figure 5B:
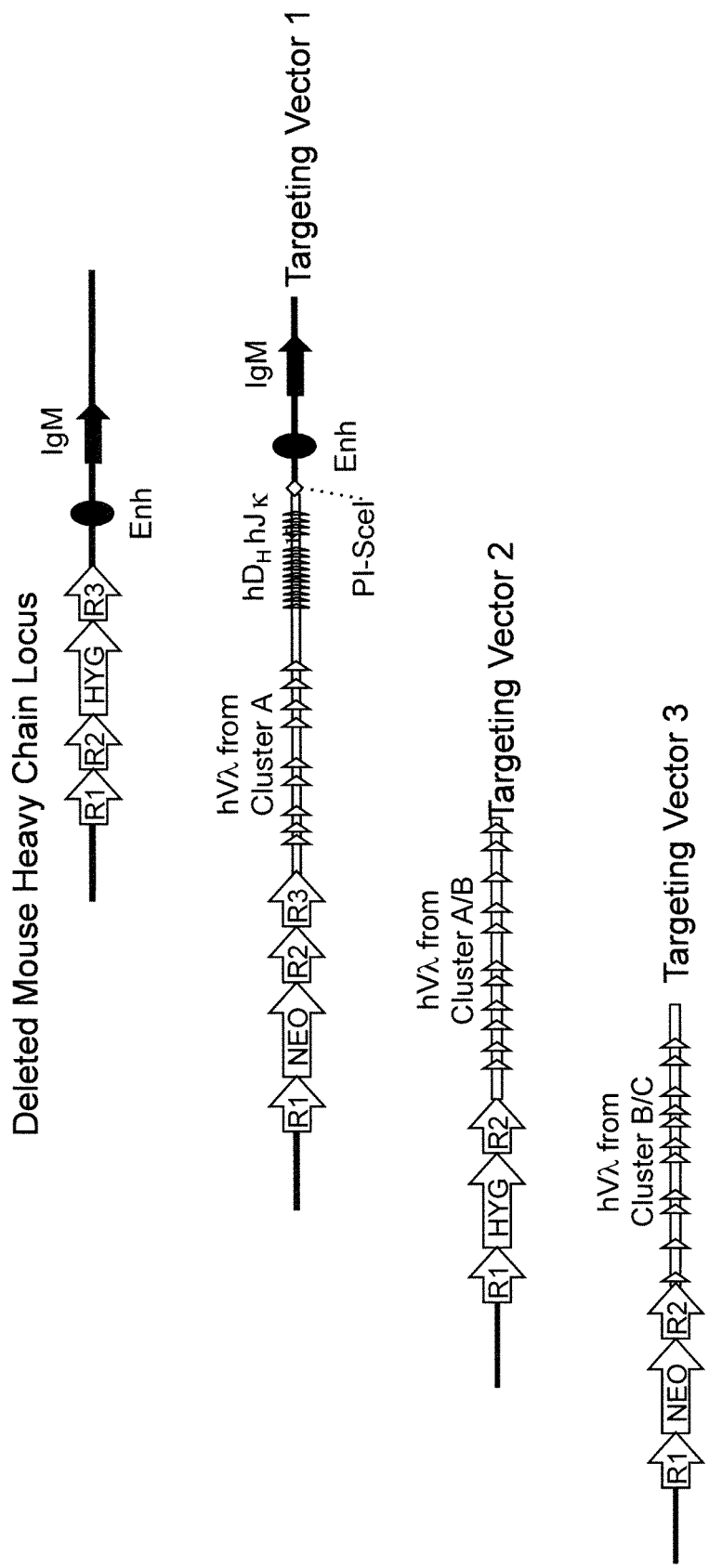
FIG. 5B shows an exemplary targeting strategy for progressive insertion of human Vλ, human $D_H$ and human Jκ gene segments into the mouse heavy chain locus. Hygromycin (HYG) and Neomycin (NEO) selection cassettes are shown with recombinase recognition sites (R1, R2, etc.).

Additionally, human $D_H$ and $J_H$ (or Jκ) gene segments can be incorporated with either human Vκ or Vλ gene segments to construct novel hybrid loci that will give rise, upon recombination, to novel engineered variable domains (FIGS. 5A and 5B). In this latter case, engineering combinations of gene segments that are not normally contained in a single locus would require specific attention to the recombination signal sequences (RSS) that are associated with respective gene segments such that normal recombination can be achieved when they are combined into a single locus. For example, V(D)J recombination is known to be guided by conserved noncoding DNA sequences, known as heptamer and nonamer sequences that are found adjacent to each gene segment at the precise location at which recombination takes place. Between these noncoding DNA sequences are non-conserved spacer regions that either 12 or 23 base pairs (bp) in length. Generally, recombination only occurs at gene segments located on the same chromosome and those gene segments flanked by a 12-bp spacer can be joined to a gene segment flanked by a 23-bp spacer, i.e. the 12/23 rule, although joining two of $D_H$ gene segments (each flanked by 12-bp spacers) has been observed in a small proportion of antibodies. To allow for recombination between gene segments that do not normally have compatible spacers (e.g., Vκ and a $D_H$ or $D_H$ and Jλ), unique, compatible spacers are synthesized in adjacent locations with the desired gene segments for construction of unique hybrid heavy chains that allow for successful recombination to form unique heavy chains containing light chain variable regions.

Thus, using the strategy outlined above for incorporation of human κ light chain gene segments into an endogenous heavy chain locus allows for the use of other combinations of human λ light chain gene segments as well as specific human heavy chain gene segments (e.g., $D_H$ and $J_H$) and combinations thereof.

Example II

Identification of Targeted ES Cells Bearing

Human Light Chain Gene Segments at an Endogenous Heavy Chain Locus

The targeted BAC DNA made in the foregoing Examples was used to electroporate mouse ES cells to created modified ES cells for generating chimeric mice that express $V_L$ binding proteins (i.e., human κ light chain gene segments operably linked to mouse heavy chain constant regions). ES cells containing an insertion of unrearranged human κ light chain gene segments were identified by the quantitative PCR assay, TAQMAN® (Lie and Petropoulos, 1998. Curr. Opin. Biotechnology 9:43-48). Specific primers sets and probes were design for insertion of human κ sequences and associated selection cassettes, loss of mouse heavy chain sequences and retention of mouse sequences flanking the endogenous heavy chain locus.

ES cells bearing the human κ light chain gene segments can be transfected with a construct that expresses a recombinase in order to remove any undesired selection cassette introduced by the insertion of the targeting construct containing human κ gene segments. Optionally, the selection cassette may be removed by breeding to mice that express the recombinase (e.g., U.S. Pat. No. 6,774,279). Optionally, the selection cassette is retained in the mice.

Example III

Generation and Analysis of Mice Expressing $V_L$ Binding Proteins

Targeted ES cells described above were used as donor ES cells and introduced into an 8-cell stage mouse embryo by the VELOCIMOUSE® method (see, e.g., U.S. Pat. No. 7,294,754 and Poueymirou, W. T., Auerbach, W., Frendewey, D., Hickey, J. F., Escaravage, J. M., Esau, L., Dore, A. T., Stevens, S., Adams, N. C., Dominguez, M. G., Gale, N. W., Yancopoulos, G. D., DeChiara, T. M., Valenzuela, D. M. (2007). F0 generation mice fully derived from gene-targeted embryonic stem cells allowing immediate phenotypic analyses. Nat Biotechnol 25, 91-99). VELOCIMICE® (F0 mice fully derived from the donor ES cell) independently bearing human κ gene segments at the mouse heavy chain locus were identified by genotyping using a modification of allele assay (Valenzuela et al., supra) that detected the presence of the unique human κ gene segments at the endogenous heavy chain locus (supra). Pups are genotyped and a pup heterozygous for the hybrid heavy chain gene locus is selected for characterizing expression of $V_L$ binding proteins.

Flow Cytometry.

The introduction of human κ light chain gene segments into the mouse heavy chain locus was carried out in an F1 ES line (F1H4; Valenzuela et al. 2007, supra) derived from 129S6/SvEvTac and C57BL/6NTac heterozygous embryos that further contained an in situ replacement of the mouse κlight chain gene segments with human κ light chain gene segments (U.S. Pat. No. 6,596,541). The human κ light chain germline variable gene segments are targeted to the 129S6 allele, which carries the IgM$^a$ haplotype, whereas the unmodified mouse C576BL/6N allele bears the IgM$^b$ haplotype. These allelic forms of IgM can be distinguished by flow cytometry using antibodies specific to the polymorphisms found in the IgM$^a$ or IgM$^b$ alleles. Heterozygous mice bearing human κ light chain gene segments at the endogenous heavy chain locus as described in Example I were evaluated for expression of human $V_L$ binding proteins using flow cytometry.

Briefly, blood was drawn from groups of mice (n=6 per group) and grinded using glass slides. C57BL/6 and Balb/c mice were used as control groups. Following lysis of red blood cells (RBCs) with ACK lysis buffer (Lonza Walkersville), cells were resuspended in BD Pharmingen FACS staining buffer and blocked with anti-mouse CD16/32 (BD Pharmingen). Lymphocytes were stained with anti-mouse IgM$^b$-FITC (BD Pharmingen), anti-mouse IgM$^a$-PE (BD Pharmingen), anti-mouse CD19 (Clone 1D3; BD Biosciences), and anti-mouse CD3 (17A2; BIOLEGEND®) followed by fixation with BD CYTOFIX™ all according to the manufacturer's instructions. Final cell pellets were resuspended in staining buffer and analyzed using a BD FACSCALIBUR™ and BD CELLQUEST PRO™ software. Table 2 sets forth the average percent values for B cells (CD19$^+$), T cells (CD3$^+$), hybrid heavy chain (CD19$^+$IgM$^{a+}$), and wild type heavy chain (CD19$^+$IgM$^{b+}$) expression observed in groups of animals bearing each genetic modification.

In a similar experiment, B cell contents of the spleen, blood and bone marrow compartments from mice homozygous for six human Vκ and five human Jκ gene segments operably linked to the mouse heavy chain constant region (described in Example I, FIG. 2) were analyzed for progression through B cell development using flow cytometry of various cell surface markers.

Briefly, two groups (n=3 each, 8 weeks old females) of wild type and mice homozygous for six human Vκ and five human Jκ gene segments operably linked to the mouse heavy chain constant region were sacrificed and blood, spleens and bone marrow were harvested. Blood was collected into microtainer tubes with EDTA (BD Biosciences). Bone marrow was collected from femurs by flushing with complete RPMI medium (RPMI medium supplemented with fetal calf serum, sodium pyruvate, Hepes, 2-mercaptoethanol, non-essential amino acids, and gentamycin). RBCs from spleen and bone marrow preparations were lysed with ACK lysis buffer (Lonza Walkersville), followed by washing with complete RPMI medium.

Cells (1×10$^6$) were incubated with anti-mouse CD16/CD32 (2.4G2, BD) on ice for ten minutes, followed by labeling with the following antibody cocktail for thirty minutes on ice: anti-mouse FITC-CD43 (1B11, BIOLEGEND®), PE-ckit (2B8, BIOLEGEND®), PeCy7-IgM (II/41, EBIOSCIENCE®), PerCP-Cy5.5-IgD (11-26c.2a, BIOLEGEND®), APC-eFluor 780-B220 (RA3-6B2, EBIOSCIENCE®), APC-CD19 (MB19-1, EBIOSCIENCE®). Bone marrow: immature B cells (B220$^{int}$IgM$^+$), mature B cells (B220$^{hi}$IgM$^+$), pro B cells (CD19$^+$ckit$^+$CD43$^+$), pre B cells (CD19$^+$ckit$^-$CD43$^-$), pre-B cells (CD19$^+$CD43$^{int}$IgM$^{+/-}$), immature B cells (CD19$^+$CD43$^-$IgM$^{+/-}$). Blood and spleen: B cells (CD19$^+$), mature B cells (CD19$^+$IgM$^{int}$IgD$^{hi}$), transitional/immature B cells (CD19$^+$IgM$^{hi}$IgD$^{int}$).

Figure 6A:
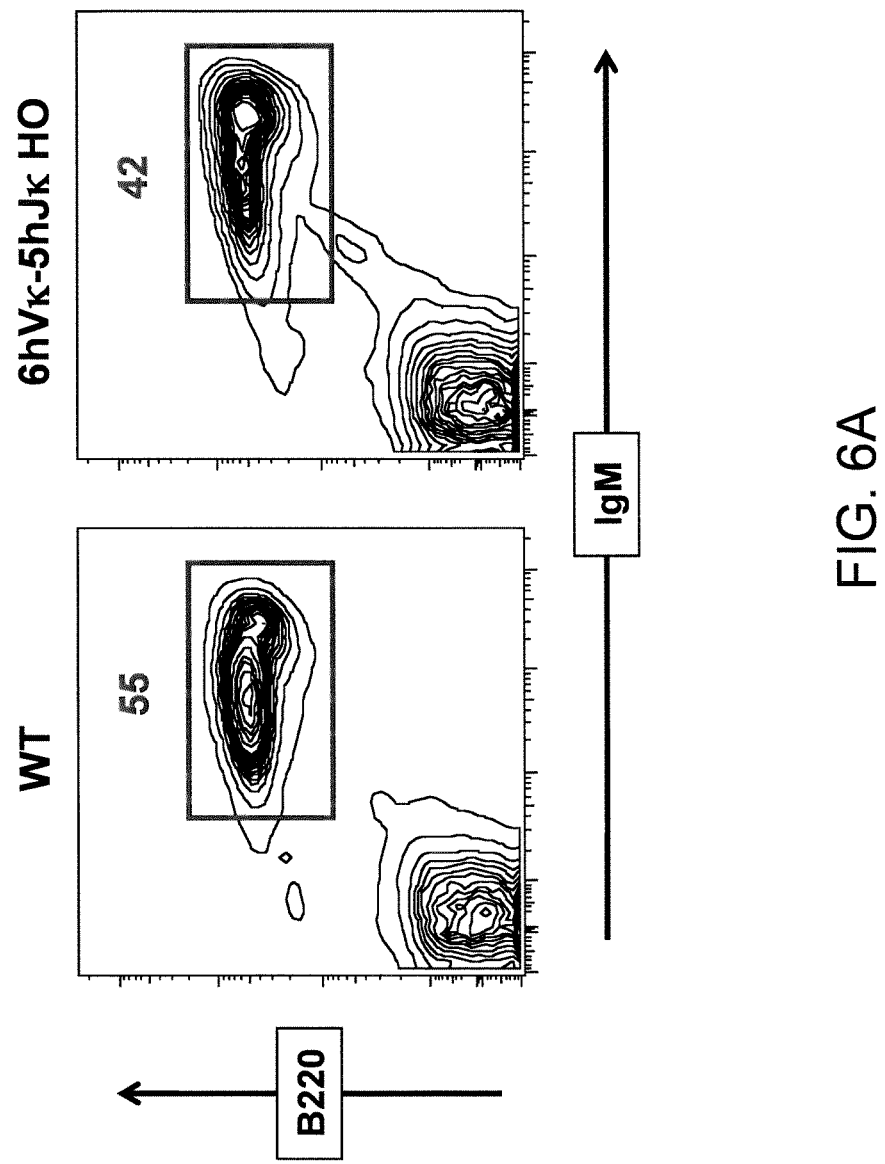
FIG. 6A shows contour plots of splenocytes stained for surface expression of B220 and IgM from a representative wild type (WT) and a representative mouse homozygous for six human Vκ and five human Jκ gene segments positioned at the endogenous heavy chain locus (6hVκ-5hJκ HO).
Figure 6B:
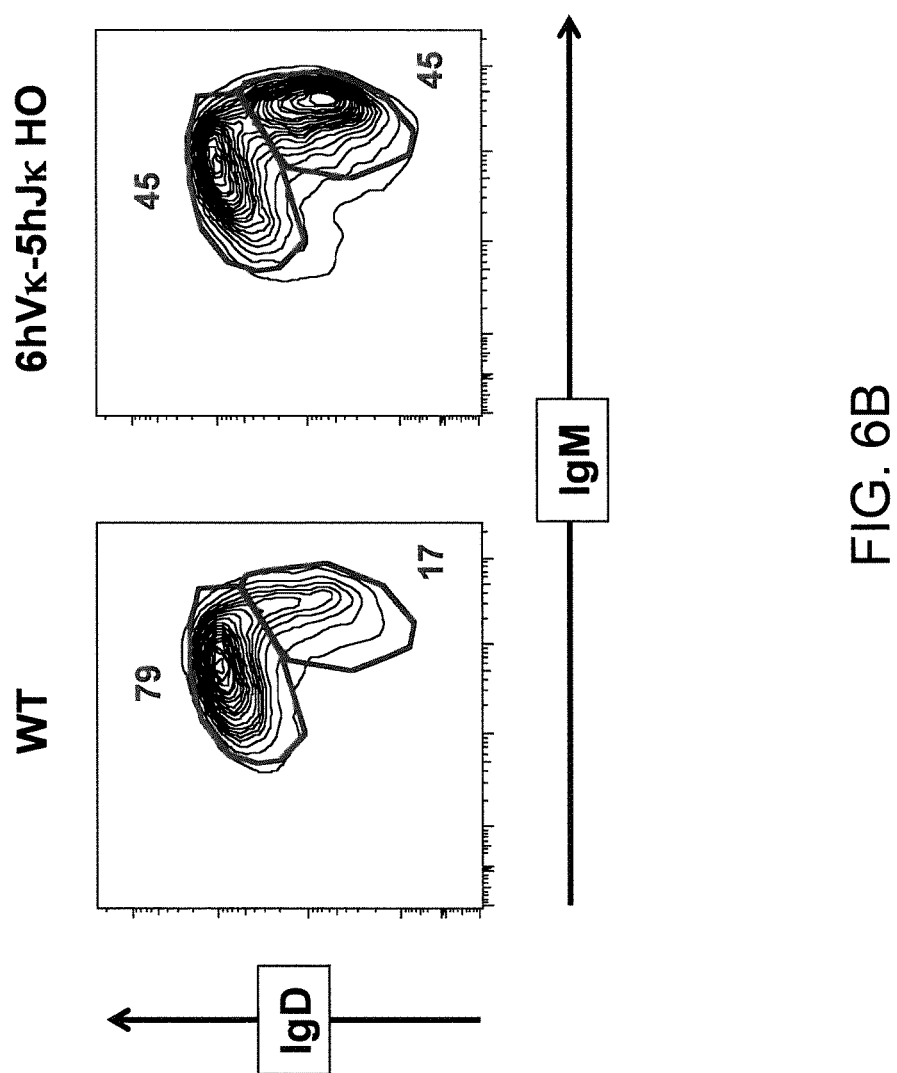
FIG. 6B shows contour plots of splenocytes gated on CD19$^+$ B cells and stained for immunoglobulin D (IgD) and immunoglobulin M (IgM) from a representative wild type (WT) and a representative mouse homozygous for six human Vκ and five human Jκ gene segments positioned at the endogenous heavy chain locus (6hVκ-5hJκ HO).
Figure 6C:
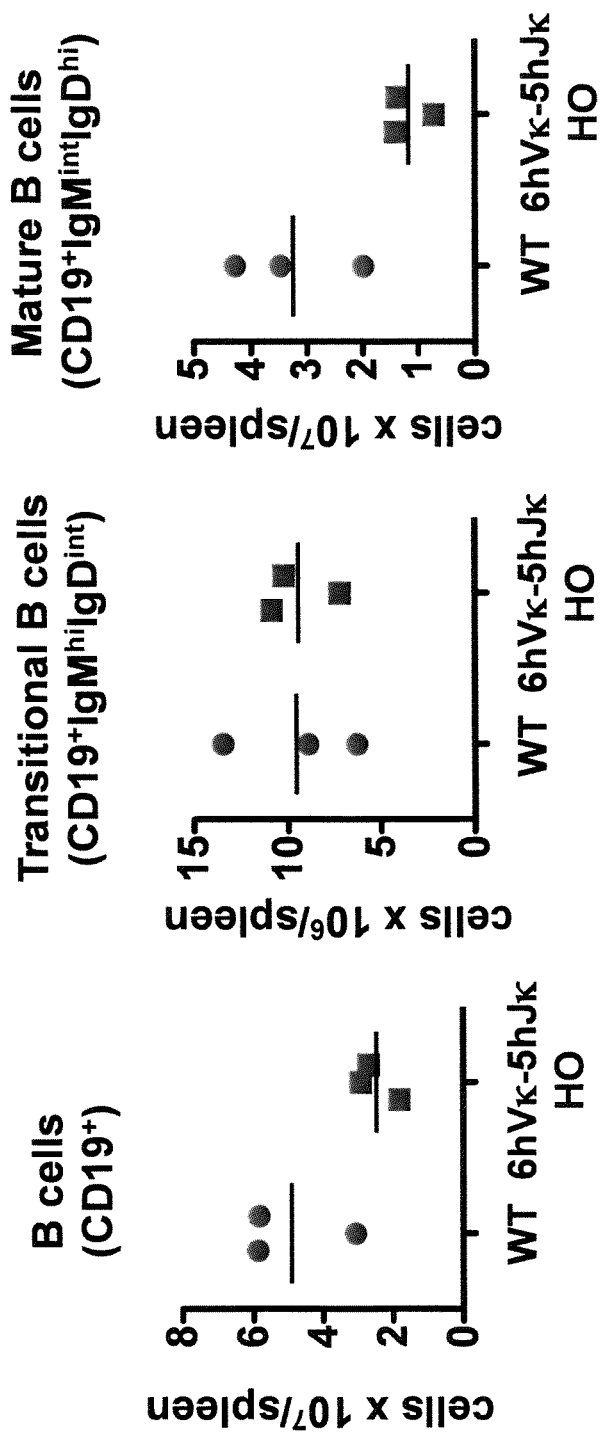
FIG. 6C shows the total number of CD19$^+$ B cells, transitional B cells (CD19$^+$IgM$^{hi}$IgD$^{int}$) and mature B cells (CD19$^+$IgM$^{int}$IgD$^{hi}$) in harvested spleens from wild type (WT) and mice homozygous for six human Vκ and five human Jκ gene segments positioned at the endogenous heavy chain locus (6hVκ-5hJκ HO).
Figure 7A:
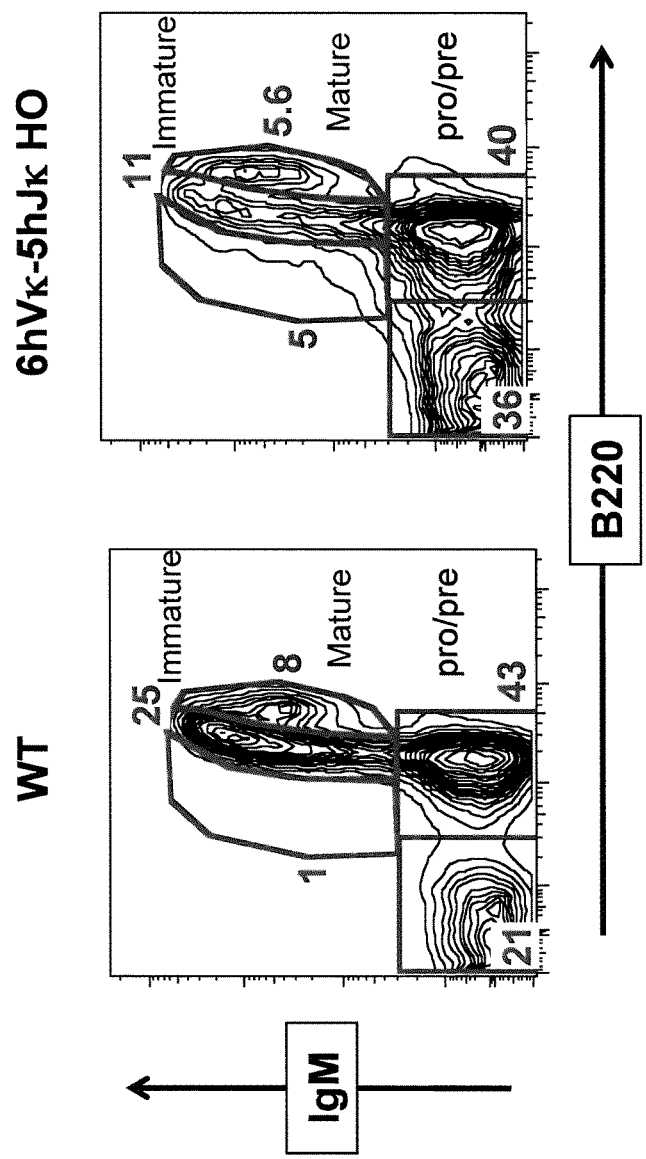
FIG. 7A shows contour plots of bone marrow gated on singlets stained for immunoglobulin M (IgM) and B220 from a wild type mouse (WT) and a mouse homozygous for six human Vκ and five human Jκ gene segments positioned at the endogenous heavy chain locus (6hVκ-5hJκ HO). Immature, mature and pro/pre B cells are noted on each of the dot plots.
Figure 7B:
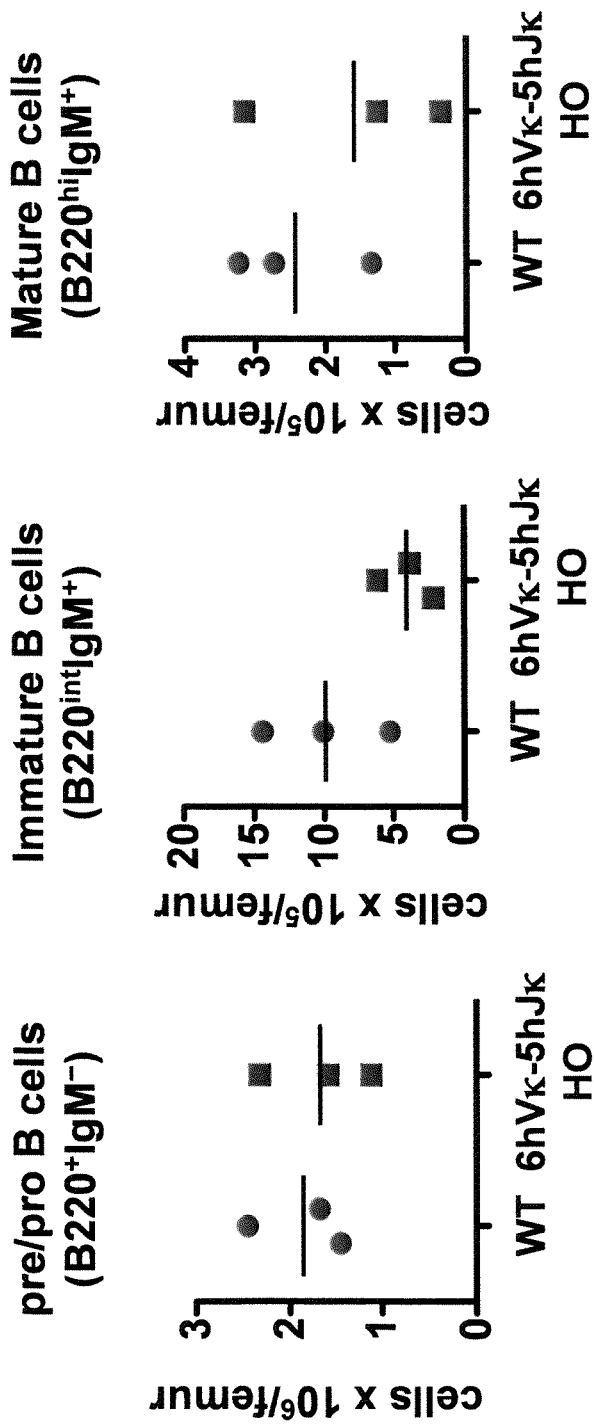
FIG. 7B shows the total number of pre/pro (B220$^+$IgM$^-$), immature (B220$^{int}$IgM$^+$) and mature (B220$^{hi}$IgM$^+$) B cells in bone marrow isolated from the femurs of wild type mice (WT) and mice homozygous for six human Vκ and five human Jκ gene segments positioned at the endogenous heavy chain locus (6hVκ-5hJκ HO).
Figure 7C:
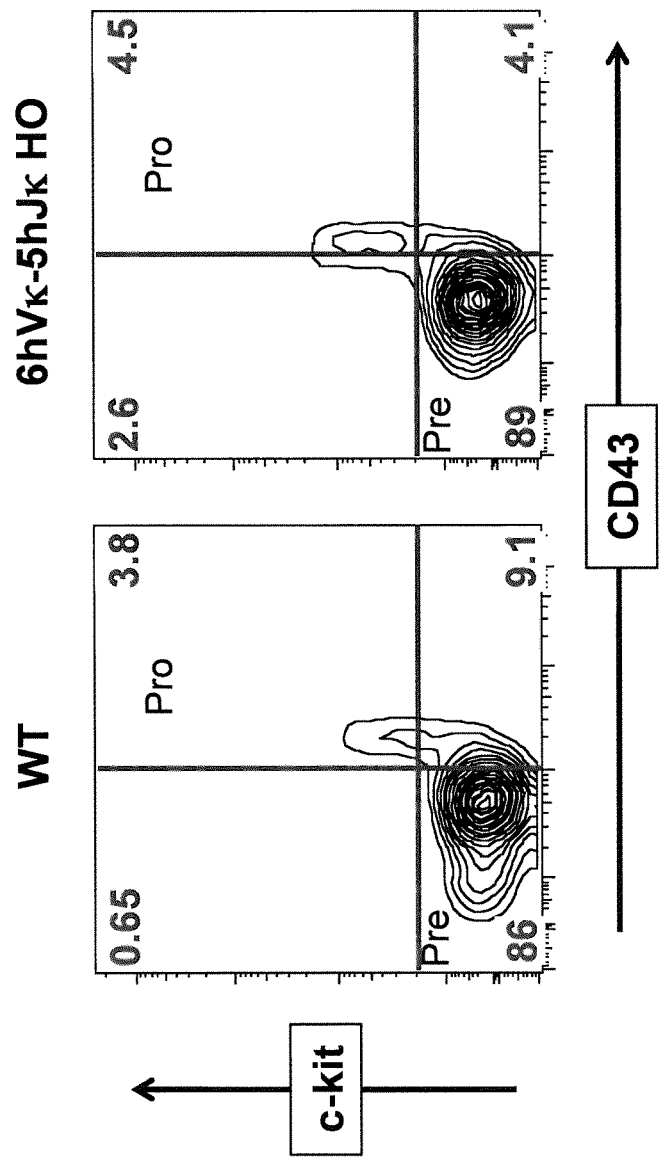
FIG. 7C shows contour plots of bone marrow gated on CD19 and stained for ckit$^+$ and CD43$^+$ from a wild type mouse (WT) and a mouse homozygous for six human Vκ and five human Jκ gene segments positioned at the endogenous heavy chain locus (6hVκ-5hJκ HO). Pro and pre B cells are noted on each of the dot plots.
Figure 7D:
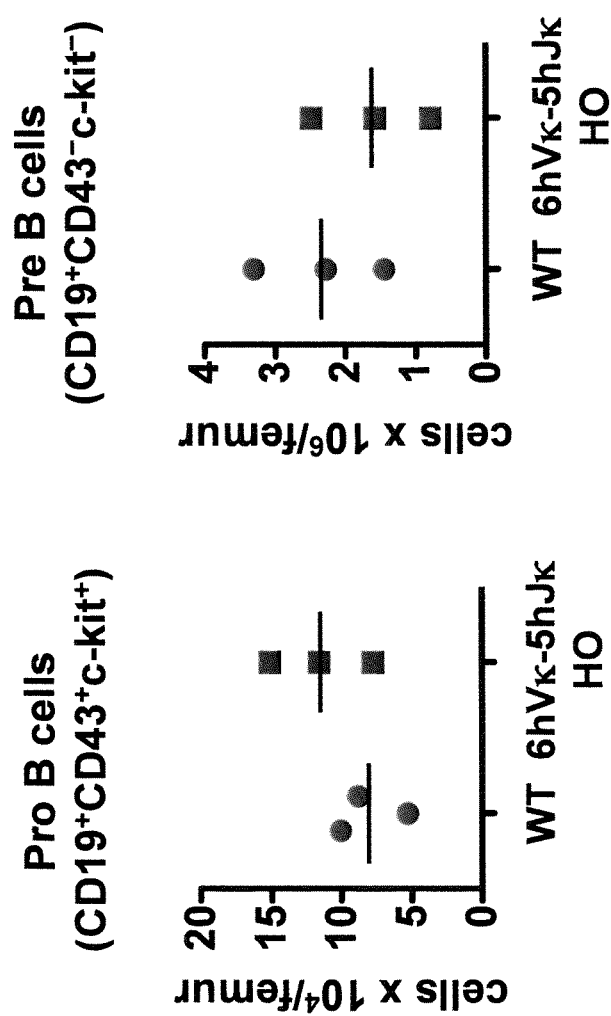
FIG. 7D shows the number of pro B (CD19$^+$CD43$^+$ckit$^+$) and pre B (CD19$^+$CD43$^-$ckit$^-$) cells in bone marrow harvested from the femurs of wild type mice (WT) and mice homozygous for six human Vκ and five human Jκ gene segments positioned at the endogenous heavy chain locus (6hVκ-5hJκ HO).
Figure 7E:
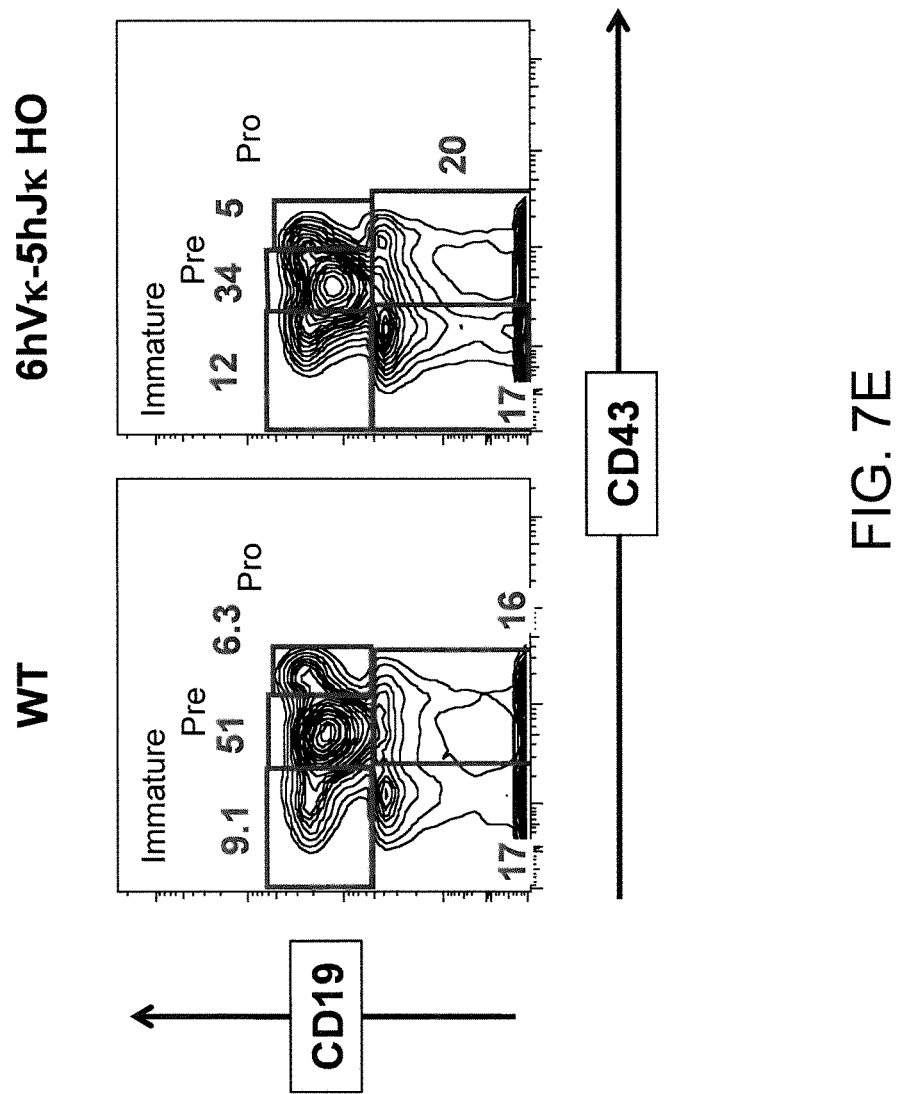
FIG. 7E shows contour plots of bone marrow gated on singlets stained for CD19 and CD43 from a wild type mouse (WT) and a mouse homozygous for six human Vκ and five human Jκ gene segments positioned at the endogenous heavy chain locus (6hVκ-5hJκ HO). Immature, pre and pro B cells are noted on each of the dot plots.
Figure 7F:
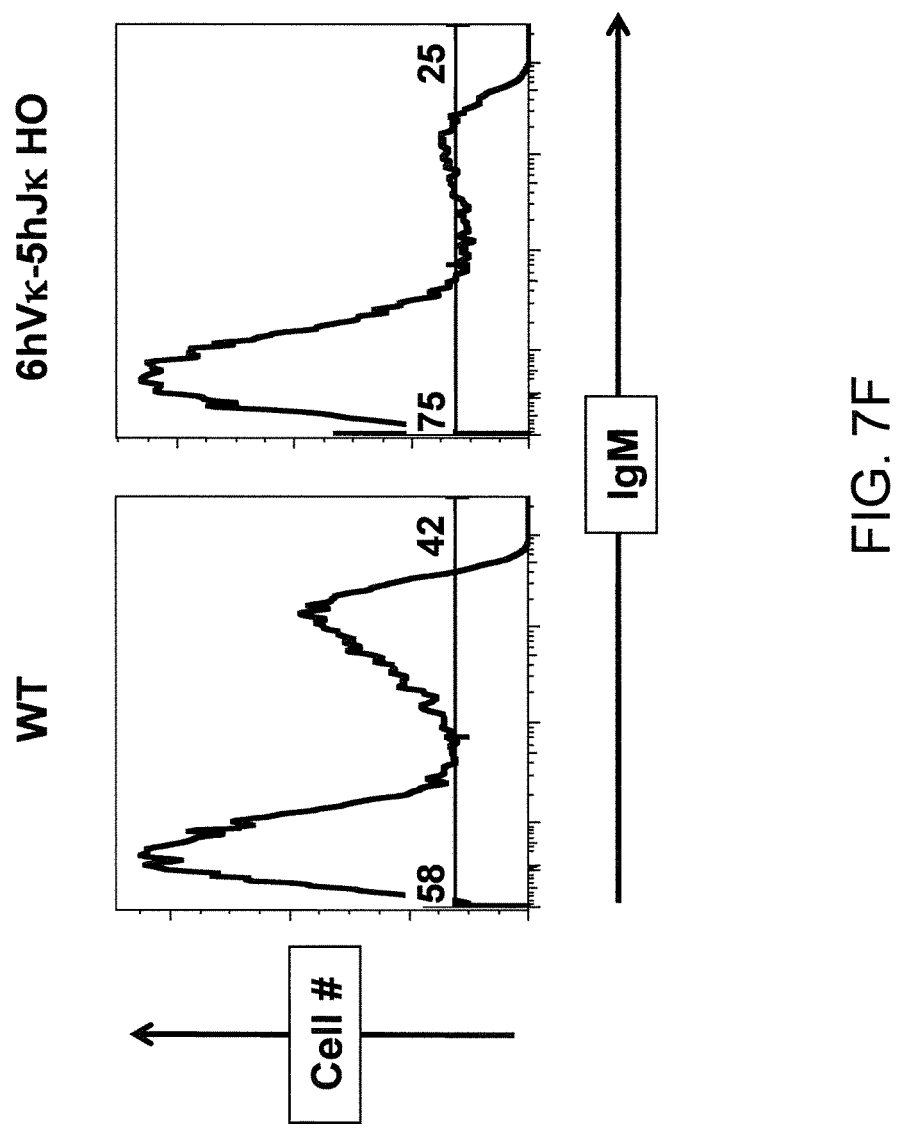
FIG. 7F shows histograms of bone marrow gated on pre B cells (CD19$^+$CD43$^{int}$) and expressing immunoglobulin M (IgM) from a wild type mouse (WT) and a mouse homozygous for six human Vκ and five human Jκ gene segments positioned at the endogenous heavy chain locus (6hVκ-5hJκ HO).
Figure 7G:
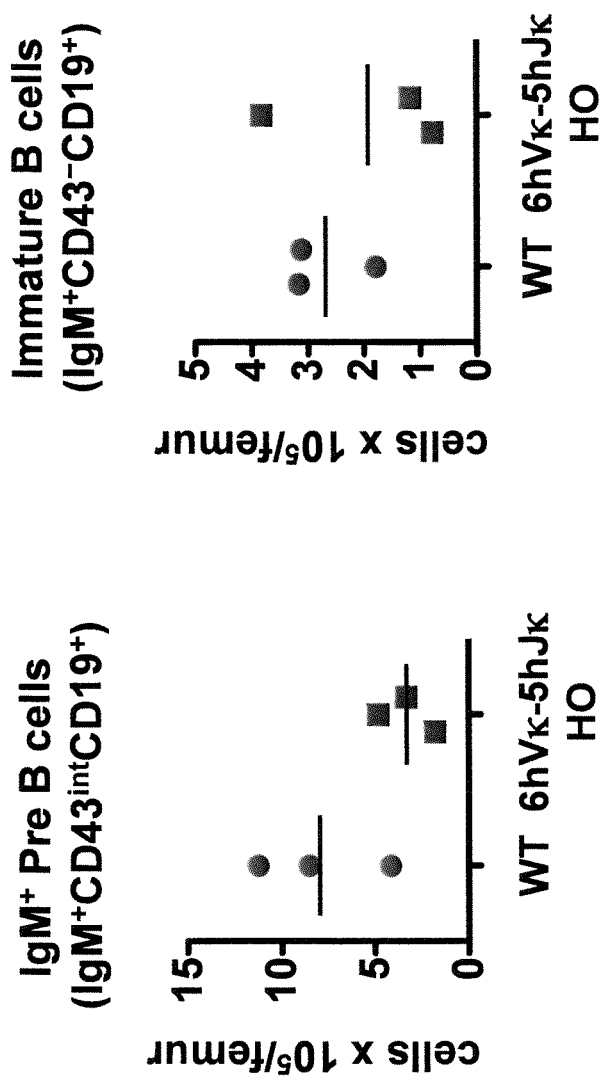
FIG. 7G shows the number of IgM$^+$ pre B cells (CD19$^+$IgM+CD43$^{int}$) and immature B cells (CD19$^+$IgMCD43$^-$) in bone marrow harvest from the femurs of wild type (WT) and mice homozygous for six human Vκ and five human Jκ gene segments positioned at the endogenous heavy chain locus (6hVκ-5hJκ HO).

Following staining, cells were washed and fixed in 2% formaldehyde. Data acquisition was performed on a LSRII flow cytometer and analyzed with FLOWJO™ software (Tree Star, Inc.). FIGS. 6A, 6B and 6C show the results for the splenic compartment. FIG. 7A-7G show the results for the bone marrow compartment. The results obtained for the blood compartment from each group of mice demonstrated similar results as compared to the results from the splenic compartment from each group (data not shown).

In a similar experiment, B cell contents of the spleen, blood and bone marrow compartments from mice homozygous for thirty human Vκ and five human Jκ gene segments operably linked to the mouse heavy chain constant region (described in Example I, FIG. 2) were analyzed for progression through B cell development using flow cytometry of various cell surface markers.

Briefly, two groups (N=3 each, 6 week old females) of mice containing a wild-type heavy chain locus and a replacement of the endogenous Vκ and Jκ gene segments with human Vκ and Jκ gene segments (WT) and mice homozygous for thirty hVκ and five Jκ gene segments and a replacement of the endogenous Vκ and Jκ gene segments with human Vκ and Jκ gene segments (30hVκ-5hJκ HO) were sacrificed and spleens and bone marrow were harvested. Bone marrow and splenocytes were prepared for staining with various cell surface markers (as described above).

Cells (1×10$^6$) were incubated with anti-mouse CD16/CD32 (2.4G2, BD Biosciences) on ice for ten minutes, followed by labeling with bone marrow or splenocyte panels for thirty minutes on ice. Bone marrow panel: anti-mouse FITC-CD43 (1B11, BIOLEGEND®), PE-ckit (2B8, BIOLEGEND®), PeCy7-IgM (II/41, EBIOSCIENCE®), APC-CD19 (MB19-1, EBIOSCIENCE®). Bone marrow and spleen panel: anti-mouse FITC-Igκ (187.1 BD Biosciences), PE-Igλ (RML-42, BIOLEGEND®), PeCy7-IgM (II/41, EBIOSCIENCE®), PerCP-Cy5.5-IgD (11-26c.2a, BIOLEGEND®), Pacific Blue-CD3 (17A2, BIOLEGEND®), APC-B220 (RA3-6B2, EBIOSCIENCE®), APC-H7-CD19 (ID3, BD). Bone marrow: immature B cells (B220$^{int}$IgM$^+$), mature B cells (B220$^{hi}$IgM$^+$), pro B cells (CD19$^+$ckit$^+$CD43$^+$), pre B cells (CD19+ckit−CD43−), immature Igκ$^+$ B cells (B220$^{int}$IgM$^+$Igλ$^-$), immature Igλ$^+$ B cells (B220$^{int}$IgM$^+$Igκ$^-$Igλ$^+$), mature Igκ B cells (B220$^{hi}$IgM$^+$Igκ$^+$Igλ$^-$), mature Igλ$^+$ B cells (B220$^{hi}$IgM$^+$Igκ$^-$Igλ$^+$). Spleen: B cells (CD19$^+$), mature B cells (CD19$^+$IgD$^{hi}$IgM$^{int}$), transitional/immature B cells (CD19$^+$IgD$^{int}$IgM$^{hi}$). Bone marrow and spleen: Igκ$^+$ B cells (CD19$^+$Igκ$^+$Igλ$^-$), Igλ$^+$ B cells (CD19$^+$Igκ$^-$Igλ$^+$).

Figure 8A:
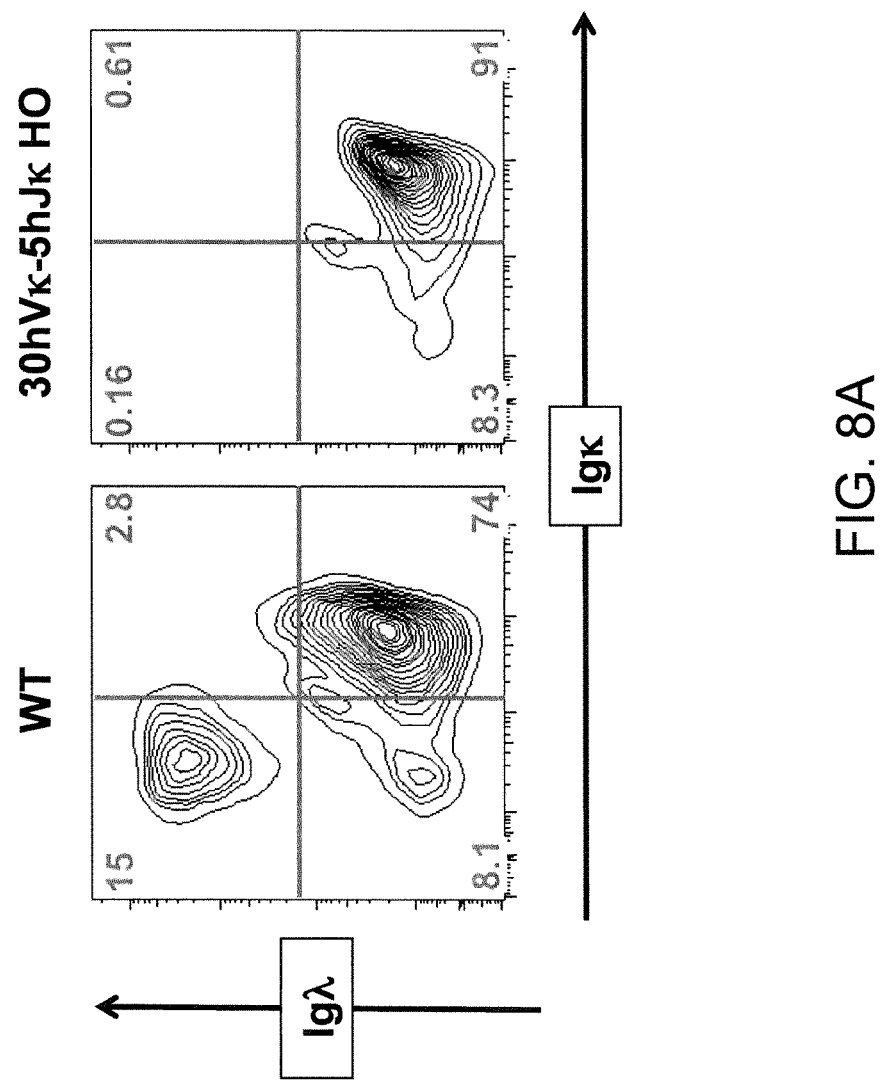
FIG. 8A shows contour plots of splenocytes gated on CD19$^+$ and stained for Igλ$^+$ and IgK$^+$ expression from a mouse containing a wild type heavy chain locus and a replacement of the endogenous Vκ and Jκ gene segments with human Vκ and Jκ gene segments (WT) and a mouse homozygous for thirty hVκ and five Jκ gene segments at the endogenous heavy chain locus and a replacement of the endogenous Vκ and Jκ gene segments with human Vκ and Jκgene segments (30hVκ-5hJκ HO).
Figure 8B:
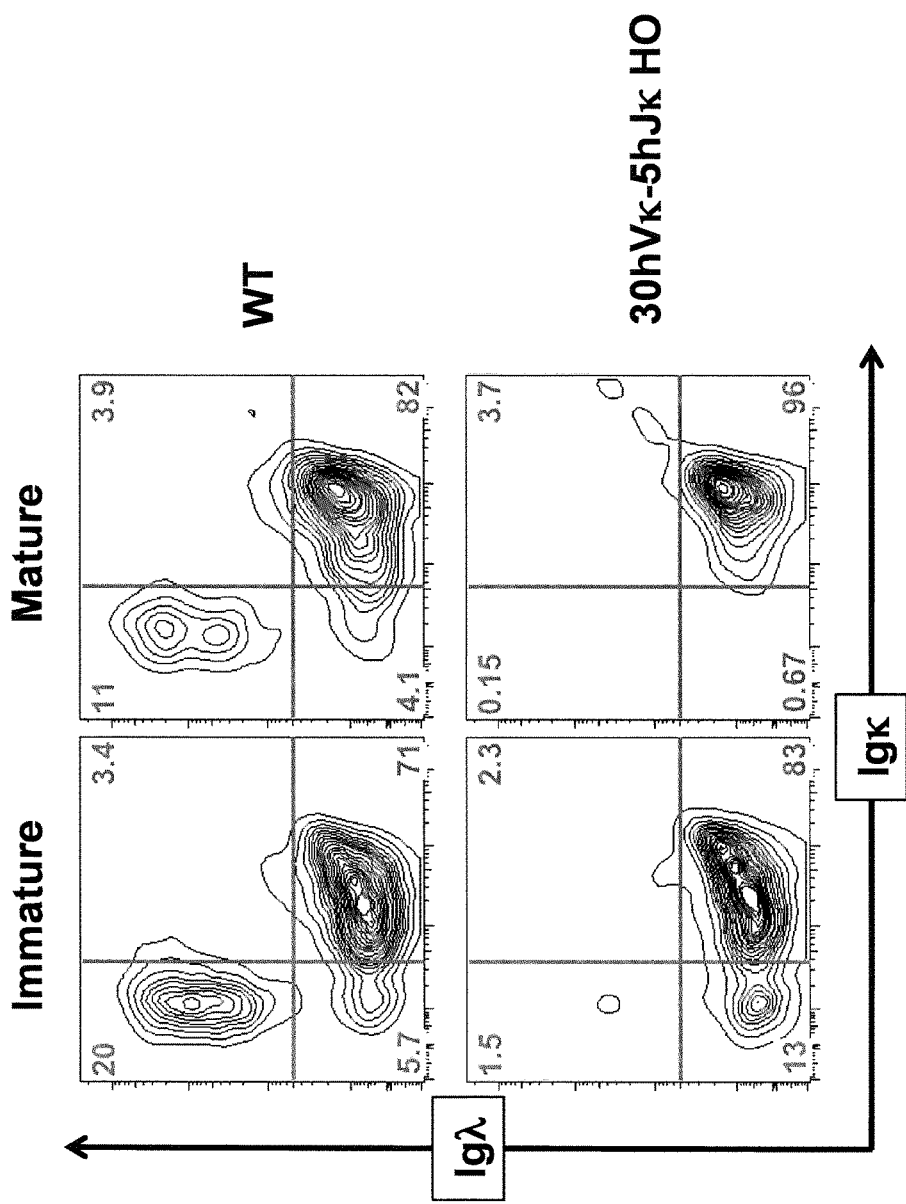
FIG. 8B shows contour plots of bone marrow gated on immature (B220$^{int}$IgM$^+$) and mature (B220$^{hi}$IgM$^+$) B cells stained for Igλ and Igκ expression isolated from the femurs of a mouse containing a wild type heavy chain locus and a replacement of the endogenous Vκ and Jκ gene segments with human Vκ and Jκ gene segments (WT) and a mouse homozygous for thirty hVκ and five Jκ gene segments at the endogenous heavy chain locus and a replacement of the endogenous Vκ and Jκ gene segments with human Vκ and Jκ gene segments (30hVκ-5hJκ HO).

Following staining, cells were washed and fixed in 2% formaldehyde. Data acquisition was performed on a LSRII flow cytometer and analyzed with FLOWJO™ software (Tree Star, Inc.). The results demonstrated similar staining patterns and cell populations for all three compartments as compared to mice homozygous for six human Vκ and five human Jκ gene segments (described above). However, these mice demonstrated a loss in endogenous λ light chain expression in both the splenic and bone marrow compartments (FIGS. 8A and 8B, respectively), despite the endogenous λ light chain locus being intact in these mice. This may reflect an inability of rearranged human κ light chain domains, in the context of heavy chain constant regions, to pair or associate with murine κ light chain domains, leading to deletion of Igλ$^+$ cells.

Isotype Expression.

Total and surface (i.e., membrane bound) immunoglobulin M (IgM) and immunoglobulin G1 (IgG1) was determined for mice homozygous for human heavy and κ light chain variable gene loci (VELCOIMMUNE® Humanized Mice, see U.S. Pat. No. 7,105,348) and mice homozygous for six human Vκ and 5 human Jκ gene segments engineered into the endogenous heavy chain locus (6hVκ-5hJκ HO) by a quantitative PCR assay using TAQMAN® probes (as described above in Example II).

Briefly, CD19$^+$ B cells were purified from the spleens of groups of mice (n=3 to 4 mice per group) using mouse CD19 Microbeads (Miltenyi Biotec) according to manufacturer's instructions. Total RNA was purified using the RNEASY™ Mini kit (Qiagen). Genomic RNA was removed using an RNase-free DNase on-column treatment (Qiagen). About 200 ng mRNA was reverse-transcribed into cDNA using the First Stand cDNA Synthesis kit (Invitrogen) and then amplified with the TAQMAN® Universal PCR Master Mix (Applied Biosystems) using the ABI 7900 Sequence Detection System (Applied Biosystems). Unique primer/probe combinations were employed to specifically determine expression of total, surface (i.e., transmembrane) and secreted forms of IgM and IgG1 isotypes (Table 3). Relative expression was normalized to the mouse κ constant region (mCκ).

TABLE 2

| Mouse Genotype | % CD3 | % CD19 | % IgM$^a$ | % IgM$^b$ |
|---|---|---|---|---|
| C57BL/6 | 22 | 63 | 0 | 100 |
| Balb/c | 11 | 60 | 100 | 0 |
| 6hVκ-5hJκ HET | 43 | 30 | 7 | 85 |
| 16hVκ-5hJκ HET | 33 | 41 | 7 | 81 |

TABLE 3

| Isotype | Sequence (5'-3') | SEQ ID NOs: |
|---|---|---|
| Surface IgM | sense: GAGAGGACCG TGGACAAGTC | 1 |
| | antisense: TGACGGTGGT GCTGTAGAAG | 2 |
| | probe: ATGCTGAGGA GGAAGGCTTT GAGAACCT | 3 |
| Total IgM | sense: GCTCGTGAGC AACTGAACCT | 4 |
| | antisense: GCCACTGCAC ACTGATGTC | 5 |
| | probe: AGTCAGCCAC AGTCACCTGC CTG | 6 |
| Surface IgG1 | sense: GCCTGCACAA CCACCATAC | 7 |
| | antisense: GAGCAGGAAG AGGCTGATGA AG | 8 |
| | probe: AGAAGAGCCT CTCCCACTCT CCTGG | 9 |
| Total IgG1 | sense: CAGCCAGCGG AGAACTACAA G | 10 |
| | antisense: GCCTCCCAGT TGCTCTTCTG | 11 |
| | probe: AACACTCAGC CCATCATGGA CACA | 12 |
| Cκ | sense: TGAGCAGCAC CCTCACGTT | 13 |
| | antisense: GTGGCCTCAC AGGTATAGCT GTT | 14 |
| | probe: ACCAAGGACG AGTATGAA | 15 |

The results from the quantitative TAQMAN® PCR assay demonstrated a decrease in total IgM and total IgG1. However, the ratio of secreted versus surface forms of IgM and IgG1 appeared normal as compared to VELCOIMMUNE® humanized mice (data not shown).

Human κGene Segment Usage and Vκ-Jκ Junction Analysis.

Naïve mice homozygous for thirty hVκ and five Jκ gene segments and a replacement of the endogenous Vκ and Jκ gene segments with human Vκ and Jκ gene segments (30hVκ-5hJκ HO) were analyzed for unique human Vκ-Jκ rearrangements on mouse heavy chain (IgG) by reverse transcription polymerase chain reaction (RT-PCR) using RNA isolated from splenocytes.

Briefly, spleens were harvested and perfused with 10 mL RPMI-1640 (Sigma) with 5% HI-FBS in sterile disposable bags. Each bag containing a single spleen was then placed into a STOMACHER™ (Seward) and homogenized at a medium setting for 30 seconds. Homogenized spleens were filtered using a 0.7 μm cell strainer and then pelleted with a centrifuge (1000 rpm for 10 minutes) and RBCs were lysed in BD PHARM LYSE™ (BD Biosciences) for three minutes. Splenocytes were diluted with RPMI-1640 and centrifuged again, followed by resuspension in 1 mL of PBS (Irvine Scientific). RNA was isolated from pelleted splenocytes using standard techniques known in the art.

RT-PCR was performed on splenocyte RNA using primers specific for human hVκgene segments and the mouse IgG. The mouse IgG primer was designed such that it was capable of amplifying RNA derived from all mouse IgG isotypes. PCR products were gel-purified and cloned into pCR2.1-TOPO TA vector (Invitrogen) and sequenced with primers M13 Forward (GTAAAACGAC GGCCAG; SEQ ID NO:16) and M13 Reverse (CAGGAAACAG CTATGAC; SEQ ID NO:17) located within the vector at locations flanking the cloning site. Human Vκ and Jκ gene segment usage among twelve selected clones are shown in Table 4. FIG. 9 sets forth the nucleotide sequence of the hVκ-hJκ-mIgG junction for the twelve selected RT-PCR clones.

As shown in this Example, mice homozygous for six human Vκ and five human Jκ gene segments or homozygous for thirty human Vκ and five human Jκ gene segments operably linked to the mouse heavy chain constant region demonstrated expression human light chain variable regions from a modified heavy chain locus containing light chain variable gene segments in their germline configuration. Progression through the various stages of B cell development was observed in these mice, indicating multiple productive recombination events involving light chain variable gene segments from an endogenous heavy chain locus and expression of such hybrid heavy chains (i.e., human light chain variable region linked to a heavy chain constant region) as part of the antibody repertoire.

TABLE 4

| Clone | Hybrid Heavy Chain | | | SEQ ID NO: |
|---|---|---|---|---|
| | Vκ | Jκ | $C_H$ | |
| 1E | 1-5 | 4 | IgG2A/C | 18 |
| 1G | 1-9 | 4 | IgG2A/C | 19 |
| 1A | 1-16 | 5 | IgG3 | 20 |
| 2E | 1-12 | 2 | IgG1 | 21 |
| 1C | 1-27 | 4 | IgG2A/C | 22 |
| 2H | 2-28 | 1 | IgG1 | 23 |
| 3D | 3-11 | 4 | IgG1 | 24 |
| 3A | 3-20 | 4 | IgG2A/C | 25 |
| 4B | 4-1 | 5 | IgG2A/C | 26 |
| 4C | 4-1 | 2 | IgG3 | 27 |
| 5A | 5-2 | 2 | IgG2A/C | 28 |
| 5D | 5-2 | 1 | IgG1 | 29 |

Example IV

Propagation of Mice Expressing $V_L$ Binding Proteins

To create a new generation of $V_L$ binding proteins, mice bearing the unrearranged human κ gene segments can be bred to another mouse containing a deletion of the other endogenous heavy chain allele. In this manner, the progeny obtained would express only hybrid heavy chains as described in Example I. Breeding is performed by standard techniques recognized in the art and, alternatively, by commercial companies, e.g., The Jackson Laboratory. Mouse strains bearing a hybrid heavy chain locus are screened for presence of the unique hybrid heavy chains and absence of traditional mouse heavy chains.

Alternatively, mice bearing the unrearranged human κ gene segments at the mouse heavy chain locus can be optimized by breeding to other mice containing one or more deletions in the mouse light chain loci (κ and λ). In this manner, the progeny obtained would express unique human κ heavy chain only antibodies as described in Example I. Breeding is similarly performed by standard techniques recognized in the art and, alternatively, by commercial companies, e.g., The Jackson Laboratory. Mouse strains bearing a hybrid heavy chain locus and one or more deletions of the mouse light chain loci are screened for presence of the unique hybrid heavy chains containing human κ light chain domains and mouse heavy chain constant domains and absence of endogenous mouse light chains.

Mice bearing an unrearranged hybrid heavy chain locus are also bred with mice that contain a replacement of the endogenous mouse κ light chain variable gene locus with the human κ light chain variable gene locus (see U.S. Pat. No. 6,596,541, Regeneron Pharmaceuticals, The VELOCIMMUNE® Humanized Mouse Technology). The VELOCIMMUNE® Humanized Mouse includes, in part, having a genome comprising human κ light chain variable regions operably linked to endogenous mouse κ light chain variable constant region loci such that the mouse produces antibodies comprising a human κ light chain variable domain and a mouse heavy chain constant domain in response to antigenic stimulation. The DNA encoding the variable regions of the light chains of the antibodies can be isolated and operably linked to DNA encoding the human light chain constant regions. The DNA can then be expressed in a cell capable of expressing the fully human light chain of the antibody. Upon a suitable breeding schedule, mice bearing a replacement of the endogenous mouse κ light chain with the human κ light chain locus and an unrearranged hybrid heavy chain locus is obtained. Unique $V_L$ binding proteins containing somatically mutated human Vκ domains can be isolated upon immunization with an antigen of interest.

Example V

Generation of $V_L$ Binding Proteins

After breeding mice that contain the unrearranged hybrid heavy chain locus to various desired strains containing modifications and deletions of other endogenous Ig loci (as described in Example IV), selected mice can be immunized with an antigen of interest.

Generally, a VELOCIMMUNE® humanized mouse containing at least one hybrid heavy chain locus is challenged with an antigen, and cells (such as B-cells) are recovered from the animal (e.g., from spleen or lymph nodes). The cells may be fused with a myeloma cell line to prepare immortal hybridoma cell lines, and such hybridoma cell lines are screened and selected to identify hybridoma cell lines that produce antibodies containing hybrid heavy chains specific to the antigen used for immunization. DNA encoding the human Vκ regions of the hybrid heavy chains may be isolated and linked to desirable constant regions, e.g., heavy chain and/or light chain. Due to the presence of human Vκ gene segments fused to the mouse heavy chain constant regions, a unique antibody-like repertoire is produced and the diversity of the immunoglobulin repertoire is dramatically increased as a result of the unique antibody format created. This confers an added level of diversity to the antigen specific repertoire upon immunization. The resulting cloned antibody sequences may be subsequently produced in a cell, such as a CHO cell. Alternatively, DNA encoding the antigen-specific $V_L$ binding proteins or the variable domains may be isolated directly from antigen-specific lymphocytes (e.g., B cells).

Initially, high affinity $V_L$ binding proteins are isolated having a human Vκ region and a mouse constant region. As described above, the $V_L$ binding proteins are characterized and selected for desirable characteristics, including affinity, selectivity, epitope, etc. The mouse constant regions are replaced with a desired human constant region to generate unique fully human $V_L$ binding proteins containing somatically mutated human Vκ domains from an unrearranged hybrid heavy chain locus of the invention. Suitable human constant regions include, for example wild type or modified IgG1 or IgG4 or, alternatively Cκ or Cλ.

Separate cohorts of mice containing a replacement of the endogenous mouse heavy chain locus with six human Vκ and five human Jκ gene segments (as described in Example 1) and a replacement of the endogenous Vκ and Jκ gene segments with human Vκ and Jκ gene segments were immunized with a human cell-surface receptor protein (Antigen X). Antigen X is administered directly onto the hind footpad of mice with six consecutive injections every 3-4 days. Two to three micrograms of Antigen X are mixed with 10 μg of CpG oligonucleotide (Cat # tlrl-modn-ODN1826 oligonucleotide; InVivogen, San Diego, Calif.) and 25 μg of Adju-Phos (Aluminum phosphate gel adjuvant, Cat# H-71639-250; Brenntag Biosector, Frederikssund, Denmark) prior to injection. A total of six injections are given prior to the final antigen recall, which is given 3-5 days prior to sacrifice. Bleeds after the 4th and 6th injection are collected and the antibody immune response is monitored by a standard antigen-specific immunoassay.

When a desired immune response is achieved splenocytes are harvested and fused with mouse myeloma cells to preserve their viability and form hybridoma cell lines. The hybridoma cell lines are screened and selected to identify cell lines that produce Antigen X-specific $V_L$ binding proteins. Using this technique several anti-Antigen X-specific $V_L$ binding proteins (i.e., binding proteins possessing human Vκ domains in the context of mouse heavy and light chain constant domains) are obtained.

Alternatively, anti-Antigen X $V_L$ binding proteins are isolated directly from antigen-positive B cells without fusion to myeloma cells, as described in U.S. 2007/0280945A1, herein specifically incorporated by reference in its entirety. Using this method, several fully human anti-Antigen X $V_L$ binding proteins (i.e., antibodies possessing human Vκ domains and human constant domains) were obtained.

Human κ Gene Segment Usage.

To analyze the structure of the anti-Antigen X $V_L$ binding proteins produced, nucleic acids encoding the human Vκ domains (from both the heavy and light chains of the $V_L$ binding protein) were cloned and sequenced using methods adapted from those described in US 2007/0280945A1 (supra). From the nucleic acid sequences and predicted amino acid sequences of the antibodies, gene usage was identified for the hybrid heavy chain variable region of selected $V_L$ binding proteins obtained from immunized mice (described above). Table 5 sets for the gene usage of human Vκ and Jκ gene segments from selected anti-Antigen X $V_L$ binding proteins, which demonstrates that mice according to the invention generate antigen-specific $V_L$ binding proteins from a variety of human Vκ and Jκ gene segments, due to a variety of rearrangements at the endogenous heavy chain and κ light chain loci both containing unrearranged human Vκ and Jκ gene segments. Human Vκ gene segments rearranged with a variety of human Jκ segments to yield unique antigen-specific $V_L$ binding proteins.

TABLE 5

| | Hybrid Heavy Chain | | Light Chain | |
|---|---|---|---|---|
| Antibody | Vκ | Jκ | Vκ | Jκ |
| A | 4-1 | 3 | 3-20 | 1 |
| B | 4-1 | 3 | 3-20 | 1 |
| C | 4-1 | 3 | 3-20 | 1 |
| D | 4-1 | 3 | 3-20 | 1 |

TABLE 5-continued

| | Hybrid Heavy Chain | | Light Chain | |
|---|---|---|---|---|
| Antibody | Vκ | Jκ | Vκ | Jκ |
| E | 4-1 | 3 | 3-20 | 1 |
| F | 4-1 | 3 | 3-20 | 1 |
| G | 4-1 | 3 | 3-20 | 1 |
| H | 4-1 | 3 | 3-20 | 1 |
| I | 4-1 | 3 | 3-20 | 1 |
| J | 1-5 | 3 | 1-33 | 3 |
| K | 4-1 | 3 | 3-20 | 1 |
| L | 4-1 | 3 | 1-9 | 3 |
| M | 4-1 | 1 | 1-33 | 4 |
| N | 4-1 | 1 | 1-33 | 3 |
| O | 1-5 | 1 | 1-9 | 2 |
| P | 1-5 | 3 | 1-16 | 4 |
| Q | 4-1 | 3 | 3-20 | 1 |
| R | 4-1 | 3 | 3-20 | 1 |
| S | 1-5 | 1 | 1-9 | 2 |
| T | 1-5 | 1 | 1-9 | 2 |
| U | 5-2 | 2 | 1-9 | 3 |
| V | 1-5 | 2 | 1-9 | 2 |
| W | 4-1 | 1 | 1-33 | 4 |

Enzyme-Linked Immunosorbent Assay (ELISA).

Human $V_L$ binding proteins raised against Antigen X were tested for their ability to block binding of Antigen X's natural ligand (Ligand Y) in an ELISA assay.

Briefly, Ligand Y was coated onto 96-well plates at a concentration of 2 μg/mL diluted in PBS and incubated overnight followed by washing four times in PBS with 0.05% Tween-20. The plate was then blocked with PBS (Irvine Scientific, Santa Ana, Calif.) containing 0.5% (w/v) BSA (Sigma-Aldrich Corp., St. Louis, Mo.) for one hour at room temperature. In a separate plate, supernatants containing anti-Antigen X $V_L$ binding proteins were diluted 1:10 in buffer. A mock supernatant with the same components of the $V_L$ binding proteins was used as a negative control. The extracellular domain (ECD) of Antigen X was conjugated to the Fc portion of mouse IgG2a (Antigen X-mFc). Antigen X-mFc was added to a final concentration of 0.150 nM and incubated for one hour at room temperature. The $V_L$ binding protein/Antigen X-mFc mixture was then added to the plate containing Ligand Y and incubated for one hour at room temperature. Detection of Antigen X-mFc bound to Ligand Y was determined with Horse-Radish Peroxidase (HRP) conjugated to anti-Penta-His antibody (Qiagen, Valencia, Calif.) and developed by standard colorimetric response using tetramethylbenzidine (TMB) substrate (BD Biosciences, San Jose, Calif.) neutralized by sulfuric acid. Absorbance was read at OD450 for 0.1 sec. Background absorbance of a sample without Antigen X was subtracted from all samples. Percent blocking was calculated for >250 (three 96 well plates) Antigen X-specific $V_L$ binding proteins by division of the background-subtracted MFI of each sample by the adjusted negative control value, multiplying by 100 and subtracting the resulting value from 100.

The results showed that several $V_L$ binding proteins isolated from mice immunized with Antigen X specifically bound the extracellular domain of Antigen X fused to the Fc portion of mouse IgG2a (data not shown).

Affinity Determination.

Equilibrium dissociation constants ($K_D$) for selected Antigen X-specific $V_L$ binding protein supernatants were determined by SPR (Surface Plasmon Resonance) using a BIACORE™ T100 instrument (GE Healthcare). All data were obtained using HBS-EP (10 mM HEPES, 150 mM NaCl, 0.3 mM EDTA, 0.05% Surfactant P20, pH 7.4) as both the running and sample buffers, at 25° C.

Briefly, $V_L$ binding proteins were captured from crude supernatant samples on a CM5 sensor chip surface previously derivatized with a high density of anti-human Fc antibodies using standard amine coupling chemistry. During the capture step, supernatants were injected across the anti-human Fc surface at a flow rate of 3 µL/min, for a total of 3 minutes. The capture step was followed by an injection of either running buffer or analyte at a concentration of 100 nM for 2 minutes at a flow rate of 35 µL/min. Dissociation of antigen from the captured $V_L$ binding protein was monitored for 6 minutes. The captured $V_L$ binding protein was removed by a brief injection of 10 mM glycine, pH 1.5. All sensorgrams were double referenced by subtracting sensorgrams from buffer injections from the analyte sensorgrams, thereby removing artifacts caused by dissociation of the $V_L$ binding protein from the capture surface. Binding data for each $V_L$ binding protein was fit to a 1:1 binding model with mass transport using BIAcore T100 Evaluation software v2.1.

The binding affinities of thirty-four selected $V_L$ binding proteins varied, with all exhibiting a $K_D$ in the nanomolar range (1.5 to 130 nM). Further, about 70% of the selected $V_L$ binding proteins (23 of 34) demonstrated single digit nanomolar affinity. $T^{1/2}$ measurements for these selected $V_L$ binding proteins demonstrated a range of about 0.2 to 66 minutes. Of the thirty-four $V_L$ binding proteins, six showed greater than 3 nM affinity for Antigen X (1.53, 2.23, 2.58, 2.59, 2.79, and 2.84). The affinity data is consistent with the $V_L$ binding proteins resulting from the combinatorial association of rearranged human light chain variable domains linked to heavy and light chain constant regions (described in Table 4) being high-affinity, clonally selected, and somatically mutated. The $V_L$ binding proteins generated by the mice described herein comprise a collection of diverse, high-affinity unique binding proteins that exhibit specificity for one or more epitopes on Antigen X.

In another experiment, selected human $V_L$ binding proteins raised against Antigen X were tested for their ability to block binding of Antigen X's natural ligand (Ligand Y) to Antigen X in a LUMINEX® bead-based assay (data not shown). The results demonstrated that in addition to specifically binding the extracellular domain of Antigen X with affinities in the nanomolar range (described above), selected $V_L$ binding proteins were also capable of binding Antigen X from cynomolgus monkey (*Macaca fascicularis*).

We claim:

1. A mouse whose germline genome comprises an endogenous immunoglobulin (Ig) heavy chain locus modified to comprise a human genomic germline kappa (κ) sequence comprising
   (i) unrearranged functional human Ig light chain variable κ (hVκ) gene segments, and
   (ii) all five unrearranged functional human Ig light chain joining κ (hJκ1-hJκ5) gene segments,
   wherein the human genomic germline κ sequence
   (A) replaces at the endogenous Ig heavy chain locus an endogenous genomic sequence comprising endogenous immunoglobulin heavy chain V gene segments, all endogenous immunoglobulin heavy chain D gene segments, and all endogenous immunoglobulin heavy chain J gene segments, and
   (B) rearranges in a B cell during B cell development to form a rearranged Ig hVκ/hJκ gene sequence operably linked to the endogenous Ig $C_H$ nucleic acid sequence at the endogenous Ig heavy chain locus, and
   wherein the mouse comprises a CD19+ B cell comprising the rearranged Ig hVκ/hJκ gene sequence operably linked to the endogenous Ig $C_H$ nucleic acid sequence.

2. The mouse of claim 1, wherein the mouse is homozygous or heterozygous for the modified endogenous Ig heavy chain locus.

3. A mouse embryonic stem cell comprising an endogenous immunoglobulin (Ig) heavy chain locus modified to comprise a human genomic germline kappa (κ) sequence comprising
   (i) unrearranged functional human Ig light chain variable κ (hVκ) gene segments, and
   (ii) all five unrearranged functional human Ig light chain joining κ (hJκ1-hJκ5) gene segments,
   wherein the human genomic germline κ sequence
   (A) replaces at the endogenous Ig heavy chain locus an endogenous genomic sequence comprising endogenous immunoglobulin heavy chain V gene segments, all endogenous immunoglobulin heavy chain D gene segments, and all endogenous immunoglobulin heavy chain J gene segments, and
   (B) rearranges in a B cell during B cell development to form a rearranged Ig Vκ/Jκ gene sequence operably linked to the endogenous Ig $C_H$ nucleic acid sequence at the endogenous Ig heavy chain locus.

4. A cell isolated from the mouse of claim 1, wherein the cell is a CD19+ B cell comprising a rearranged Ig hVκ/hJκ nucleotide sequence operably linked to the endogenous Ig $C_H$ nucleic acid sequence at the endogenous mouse Ig heavy chain locus.

5. A hybridoma comprising a myeloma cell line fused with the CD19+ B cell of claim 4.

6. A method for making a genetically modified mouse comprising:
   (a) replacing in a mouse embryonic stem (ES) cell, at an endogenous immunoglobulin (Ig) heavy chain locus, an endogenous genomic sequence comprising endogenous immunoglobulin heavy chain V gene segments, all endogenous immunoglobulin heavy chain D gene segments, and all endogenous immunoglobulin heavy chain J gene segments with a human genomic germline kappa (κ) sequence comprising
      (i) unrearranged functional human Ig light chain variable κ (hVκ) gene segments, and
      (ii) all five unrearranged functional human Ig light chain joining κ (hJκ1-hJκ5) gene segments,
   (b) introducing the mouse ES cell into a host mouse embryo to form a chimeric mouse embryo, and
   (c) introducing the chimeric mouse embryo into a host mouse to develop into a genetically modified mouse.

* * * * *

SEQUENCE LISTING

```
<160> NUMBER OF SEQ ID NOS: 29

<210> SEQ ID NO 1
<211> LENGTH: 20
<212> TYPE: DNA
<213> ORGANISM: Artificial Sequence
<220> FEATURE:
<223> OTHER INFORMATION: synthetic

<400> SEQUENCE: 1
gagaggaccg tggacaagtc                                              20

<210> SEQ ID NO 2
<211> LENGTH: 20
<212> TYPE: DNA
<213> ORGANISM: Artificial Sequence
<220> FEATURE:
<223> OTHER INFORMATION: synthetic

<400> SEQUENCE: 2
tgacggtggt gctgtagaag                                              20

<210> SEQ ID NO 3
<211> LENGTH: 28
<212> TYPE: DNA
<213> ORGANISM: Artificial Sequence
<220> FEATURE:
<223> OTHER INFORMATION: synthetic

<400> SEQUENCE: 3
atgctgagga ggaaggcttt gagaacct                                     28

<210> SEQ ID NO 4
<211> LENGTH: 20
<212> TYPE: DNA
<213> ORGANISM: Artificial Sequence
<220> FEATURE:
<223> OTHER INFORMATION: synthetic

<400> SEQUENCE: 4
```

-continued gctcgtgagc aactgaacct                                          20

<210> SEQ ID NO 5
<211> LENGTH: 19
<212> TYPE: DNA
<213> ORGANISM: Artificial Sequence
<220> FEATURE:
<223> OTHER INFORMATION: synthetic

<400> SEQUENCE: 5
gccactgcac actgatgtc                                           19

<210> SEQ ID NO 6
<211> LENGTH: 23
<212> TYPE: DNA
<213> ORGANISM: Artificial Sequence
<220> FEATURE:
<223> OTHER INFORMATION: synthetic

<400> SEQUENCE: 6
agtcagccac agtcacctgc ctg                                      23

<210> SEQ ID NO 7
<211> LENGTH: 19
<212> TYPE: DNA
<213> ORGANISM: Artificial Sequence
<220> FEATURE:
<223> OTHER INFORMATION: synthetic

<400> SEQUENCE: 7
gcctgcacaa ccaccatac                                           19

<210> SEQ ID NO 8
<211> LENGTH: 22
<212> TYPE: DNA
<213> ORGANISM: Artificial Sequence
<220> FEATURE:
<223> OTHER INFORMATION: synthetic

<400> SEQUENCE: 8
gagcaggaag aggctgatga ag                                       22

<210> SEQ ID NO 9
<211> LENGTH: 25
<212> TYPE: DNA
<213> ORGANISM: Artificial Sequence
<220> FEATURE:
<223> OTHER INFORMATION: synthetic

<400> SEQUENCE: 9
agaagagcct ctcccactct cctgg                                    25

<210> SEQ ID NO 10
<211> LENGTH: 21
<212> TYPE: DNA
<213> ORGANISM: Artificial Sequence
<220> FEATURE:
<223> OTHER INFORMATION: synthetic

<400> SEQUENCE: 10
cagccagcgg agaactacaa g                                        21

<210> SEQ ID NO 11
<211> LENGTH: 20
<212> TYPE: DNA
<213> ORGANISM: Artificial Sequence

```
<220> FEATURE:
<223> OTHER INFORMATION: synthetic

<400> SEQUENCE: 11
gcctcccagt tgctcttctg                                              20

<210> SEQ ID NO 12
<211> LENGTH: 24
<212> TYPE: DNA
<213> ORGANISM: Artificial Sequence
<220> FEATURE:
<223> OTHER INFORMATION: synthetic

<400> SEQUENCE: 12
aacactcagc ccatcatgga caca                                         24

<210> SEQ ID NO 13
<211> LENGTH: 19
<212> TYPE: DNA
<213> ORGANISM: Artificial Sequence
<220> FEATURE:
<223> OTHER INFORMATION: synthetic

<400> SEQUENCE: 13
tgagcagcac cctcacgtt                                               19

<210> SEQ ID NO 14
<211> LENGTH: 23
<212> TYPE: DNA
<213> ORGANISM: Artificial Sequence
<220> FEATURE:
<223> OTHER INFORMATION: synthetic

<400> SEQUENCE: 14
gtggcctcac aggtatagct gtt                                          23

<210> SEQ ID NO 15
<211> LENGTH: 18
<212> TYPE: DNA
<213> ORGANISM: Artificial Sequence
<220> FEATURE:
<223> OTHER INFORMATION: synthetic

<400> SEQUENCE: 15
accaaggacg agtatgaa                                                18

<210> SEQ ID NO 16
<211> LENGTH: 16
<212> TYPE: DNA
<213> ORGANISM: Artificial Sequence
<220> FEATURE:
<223> OTHER INFORMATION: synthetic

<400> SEQUENCE: 16
gtaaaacgac ggccag                                                  16

<210> SEQ ID NO 17
<211> LENGTH: 17
<212> TYPE: DNA
<213> ORGANISM: Artificial Sequence
<220> FEATURE:
<223> OTHER INFORMATION: synthetic

<400> SEQUENCE: 17
caggaaacag ctatgac                                                 17
```

<210> SEQ ID NO 18
<211> LENGTH: 145
<212> TYPE: DNA
<213> ORGANISM: Artificial Sequence
<220> FEATURE:
<223> OTHER INFORMATION: synthetic

<400> SEQUENCE: 18

```
tctgggacag aattcactct caccatcagc agcctgcagc ctgatgattt tgcaacttat      60
tactgccaac agtataatac cctcactttc ggcggaggga ccaaggtgga gatcaaaccc     120
aaaacaacag ccccatcggt ctatc                                           145
```

<210> SEQ ID NO 19
<211> LENGTH: 151
<212> TYPE: DNA
<213> ORGANISM: Artificial Sequence
<220> FEATURE:
<223> OTHER INFORMATION: synthetic

<400> SEQUENCE: 19

```
tctgggacag aatccactct cacaatcagc agcctgcagc ctgaagattt tgcaacttat      60
tactgtcaac agcttaatag ttaccctttc actttcggcg agggaccaa ggtggagatc      120 aaacccaaaa caacagcccc atcggtctat c                                    151
```

<210> SEQ ID NO 20
<211> LENGTH: 151
<212> TYPE: DNA
<213> ORGANISM: Artificial Sequence
<220> FEATURE:
<223> OTHER INFORMATION: synthetic

<400> SEQUENCE: 20

```
tctgggacag atttcactct caccatcagc agcctgcagc ctgaagattt tgcaacttat      60
tactgccaac agtataatag ttaccctccc accttcggcc aagggacacg actggagatt     120
aaacctacaa caacagcccc atctgtctat c                                    151
```

<210> SEQ ID NO 21
<211> LENGTH: 153
<212> TYPE: DNA
<213> ORGANISM: Artificial Sequence
<220> FEATURE:
<223> OTHER INFORMATION: synthetic

<400> SEQUENCE: 21

```
tctgggacag atttcactct caccatcagc agcctgcagc ctgaagattt tgcaacttac      60
tattgtcaac aggctaacag tttcccgtac actttttggcc aggggaccaa gctggagatc    120
aaacccaaaa cgacaccccc atctgtctat cca                                  153
```

<210> SEQ ID NO 22
<211> LENGTH: 151
<212> TYPE: DNA
<213> ORGANISM: Artificial Sequence
<220> FEATURE:
<223> OTHER INFORMATION: synthetic

<400> SEQUENCE: 22

```
tctgggacag atttcactct caccatcagc agcctgcagc ctgaagatgt tgcaacttat      60
tactgtcaaa agtataacag tgcccctcac actttcggcg agggaccaa ggtggagatc      120 aaacccaaaa caacagcccc atcggtctat c                                    151
```

<210> SEQ ID NO 23
<211> LENGTH: 153
<212> TYPE: DNA
<213> ORGANISM: Artificial Sequence
<220> FEATURE:
<223> OTHER INFORMATION: synthetic

<400> SEQUENCE: 23
tcaggcacag attttacact gaaaatcagc agagtggagg ctgaggatgt tggggtttat    60
tactgcatgc aagctctaca aatttcgtgg acgttcggcc aagggaccaa ggtggaaatc   120
aaacccaaaa cgacaccccc atctgtctat cca                                153

<210> SEQ ID NO 24
<211> LENGTH: 150
<212> TYPE: DNA
<213> ORGANISM: Artificial Sequence
<220> FEATURE:
<223> OTHER INFORMATION: synthetic

<400> SEQUENCE: 24
tctgggacag acttcactct caccatcagc agcctagagc ctgaagattt tgcagtttat    60
tactgtcagc agcgtagccc ccgtttcact ttcggcggag ggaccaaggt ggagatcaaa   120
cccaaaacga caccccatc tgtctatcca                                     150

<210> SEQ ID NO 25
<211> LENGTH: 148
<212> TYPE: DNA
<213> ORGANISM: Artificial Sequence
<220> FEATURE:
<223> OTHER INFORMATION: synthetic

<400> SEQUENCE: 25
tctgggacag acttcactct caccatcagc agactggagc ctgaagattt tgccgtgtat    60
tactgtcagc agtatggtag ctcactcact ttcggcggag ggaccaaggt ggagatcaaa   120
cccaaaacaa cagccccatc ggtctatc                                      148

<210> SEQ ID NO 26
<211> LENGTH: 151
<212> TYPE: DNA
<213> ORGANISM: Artificial Sequence
<220> FEATURE:
<223> OTHER INFORMATION: synthetic

<400> SEQUENCE: 26
tctgggacag atttcactct caccatcagc agcctgcagg ctgaagatgt ggcagtttat    60
tactgtcagc aatattatag tactccgatc accttcggcc aagggacacg actggagatt   120
aaacccaaaa caacagcccc atcggtctat c                                  151

<210> SEQ ID NO 27
<211> LENGTH: 151
<212> TYPE: DNA
<213> ORGANISM: Artificial Sequence
<220> FEATURE:
<223> OTHER INFORMATION: synthetic

<400> SEQUENCE: 27
tctgggacag atttcactct caccatcagc agcctgcagg ctgaagatgt ggcagtttat    60
tactgtcagc aatattatag tactgggccc acttttggcc aggggaccaa gctggagatc   120

```
aaacctacaa caacagcccc atctgtctat c                              151

<210> SEQ ID NO 28
<211> LENGTH: 151
<212> TYPE: DNA
<213> ORGANISM: Artificial Sequence
<220> FEATURE:
<223> OTHER INFORMATION: synthetic

<400> SEQUENCE: 28
tatggaacag attttacccct cacaattaat aacattgaat gtgaggatgc tgcatattac    60
ttctgtctac aacatgataa tttcccgtac acttttggcc aggggaccaa gctggagatc   120
aaacccaaaa caacagcccc atcggtctat c                                  151

<210> SEQ ID NO 29
<211> LENGTH: 147
<212> TYPE: DNA
<213> ORGANISM: Artificial Sequence
<220> FEATURE:
<223> OTHER INFORMATION: synthetic

<400> SEQUENCE: 29
tatggaacag attttacccct cacaattaat aacatagaat ctgaggatgc tgcatattac    60
ttctgtctac aacatgataa ttggacgttc ggccaaggga ccaaggtgga atcaaaccc    120 aaaacgacac ccccatctgt ctatcca                                       147
```